United States Patent
Pinsky et al.

(10) Patent No.: US 10,093,994 B2
(45) Date of Patent: Oct. 9, 2018

(54) METHODS AND REAGENTS FOR DETECTION, QUANTITATION, AND SEROTYPING OF DENGUE VIRUSES

(71) Applicant: The Board of Trustees of the Leland Stanford Junior University, Standford, CA (US)

(72) Inventors: Benjamin Pinsky, San Jose, CA (US); Jesse Waggoner, Palo Alto, CA (US)

(73) Assignee: The Board of Trustees of the Leland Stanford Junior University, Stanford, CA (US)

(*) Notice: Subject to any disclaimer, the term of this patent is extended or adjusted under 35 U.S.C. 154(b) by 0 days.

(21) Appl. No.: 15/639,930

(22) Filed: Jun. 30, 2017

(65) Prior Publication Data
US 2017/0306425 A1    Oct. 26, 2017

Related U.S. Application Data

(62) Division of application No. 14/430,715, filed as application No. PCT/US2013/063238 on Oct. 3, 2013, now Pat. No. 9,725,774.

(60) Provisional application No. 61/709,687, filed on Oct. 4, 2012.

(51) Int. Cl.
| | | |
|---|---|---|
| C12Q 1/68 | (2018.01) | |
| C12P 19/34 | (2006.01) | |
| C12Q 1/70 | (2006.01) | |
| B01L 3/00 | (2006.01) | |
| C07H 21/04 | (2006.01) | |

(52) U.S. Cl.
CPC .................... C12Q 1/701 (2013.01)

(58) Field of Classification Search
CPC ...... C12Q 1/686; C12Q 1/689; C12Q 1/6872; B01L 7/52
See application file for complete search history.

(56) References Cited

U.S. PATENT DOCUMENTS

| | | |
|---|---|---|
| 2008/0311157 A1 | 12/2008 | Vazquez et al. |
| 2010/0211327 A1 | 8/2010 | Hahner et al. |

FOREIGN PATENT DOCUMENTS

| | | |
|---|---|---|
| WO | WO2008051266 | 5/2008 |
| WO | WO2011026139 | 3/2011 |
| WO | WO2012153153 | 11/2012 |
| WO | WO2013064834 | 5/2013 |

OTHER PUBLICATIONS

Mackay, "Real-time PCR in the microbiology laboratory", Clin. Microbiol. Infect., Mar. 2004, 10(3): 190-212.
Gijavanekar, et al. "PCR detection of nearly any dengue virus strain using a highly sensitive primer 'cocktail'", FEBS J., Apr. 18, 2011, vol. 278, No. 10, pp. 1676-1687.
GenBank, Accession: 00863566, VRL Aug. 2, 2011.
Fredman, Are Oligonucleotide Primers and Probes Prima Facie Obvious Over Larger Prior Art Nucleic Acids, 2003, Santa Clara Computer & High Technology Law Journal, 19(1):285-313.
Yong, et al. "Rapid detection and serotyping of dengue virus by multiplex RT-PCR and real-time SYBR green RT-PCR", Singapore Met J., Jul. 31, 2007, vol. 48, No. 7, pp. 662-668.
Waggoner, et al. "Single-reaction, multiplex, real-time RT-PCR for the detection, quantitation, and serotyping of dengue viruses" PLoS Negl. Trop. Dis., Apr. 18, 2013, vol. 7, No. 4, pp. e2116:1-e2116:9.
Waggoner, et al. "Comparison of the FDA-approved CDC DENV-1-4 real-time reverse transcription-PCR with a laboratory-developed assay for dengue virus detection and serotyping", J. Clin. Microbiol., Jul. 31, 2013, vol. 51, No. 10, pp. 3418-3420.
Waggoner, et al. "Development of an internally controlled real-time reverse transcriptase PCR assay for pan-dengue virus detection and comparison of four molecular dengue virus detection assays", J. Clin. Microbiol., May 1, 2013, vol. 51, No. 7, pp. 2172-2181.

*Primary Examiner* — Barry A Chestnut
(74) *Attorney, Agent, or Firm* — James S. Keddie; Bozicevic, Field & Francis LLP

(57) ABSTRACT

Methods and oligonucleotide reagents for diagnosing dengue virus infection are described. In particular, the invention relates to methods for detection, quantitation, and serotyping dengue virus, including serotypes 1-4. The dengue virus can be specifically detected by these methods even in samples containing other viruses, such as West Nile virus, Japanese encephalitis virus, tick-born encephalitis virus, HIV, or HCV.

11 Claims, 4 Drawing Sheets
Specification includes a Sequence Listing.

```
                           SEQUENCE LISTING

<160> NUMBER OF SEQ ID NOS: 21

<210> SEQ ID NO 1
<211> LENGTH: 10735
<212> TYPE: DNA
<213> ORGANISM: Dengue virus type 1
<300> PUBLICATION INFORMATION:
<308> DATABASE ACCESSION NUMBER: NCBI/NC_001477
<309> DATABASE ENTRY DATE: 2011-11-17
<313> RELEVANT RESIDUES IN SEQ ID NO: (1)..(10735)

<400> SEQUENCE: 1
agttgttagt ctacgtggac cgacaagaac agtttcgaat cggaagcttg cttaacgtag        60
ttctaacagt tttttattag agagcagatc tctgatgaac aaccaacgga aaaagacggg       120
tcgaccgtct ttcaatatgc tgaaacgcgc gagaaaccgc gtgtcaactg tttcacagtt       180
ggcgaagaga ttctcaaaag gattgctttc aggccaagga cccatgaaat tggtgatggc       240
ttttatagca ttcctaagat ttctagccat acctccaaca gcaggaattt tggctagatg       300
gggctcattc aagaagaatg gagcgatcaa agtgttacgg ggtttcaaga agaaatctc       360 aaacatgttg aacataatga caggaggaa aagatctgtg accatgctcc tcatgctgct       420
gcccacagcc ctggcgttcc atctgaccac ccgaggggga gagccgcaca tgatagttag       480
caagcaggaa agaggaaaat cacttttgtt taagacctct gcaggtgtca acatgtgcac       540
ccttattgca atggatttgg gagagttatg tgaggacaca atgacctaca atgcccccg        600 gatcactgag acggaaccag atgacgttga ctgttggtgc aatgccacgg agacatgggt       660
gacctatgga acatgttctc aaactggtga acaccgacga gacaaacgtt ccgtcgcact       720
ggcaccacac gtagggcttg gtctagaaac aagaaccgaa acgtggatgt cctctgaagg       780
cgcttggaaa caaatacaaa aagtggagac ctgggctctg agacacccag gattcacggt       840
gatagccctt tttctagcac atgccatagg aacatccatc acccagaaag ggatcatttt       900
tattttgctg atgctggtaa ctccatccat ggccatgcgg tgcgtgggaa taggcaacag       960
agacttcgtg gaaggactgt caggagctac gtgggtggat gtggtactgg agcatggaag      1020
ttgcgtcact accatggcaa aagacaaacc aacactggac attgaactct tgaagacgga      1080
ggtcacaaac cctgccgtcc tgcgcaaact gtgcattgaa gctaaaatat caaacaccac      1140
caccgattcg agatgtccaa cacaaggaga agccacgctg gtggaagaac aggacacgaa      1200
ctttgtgtgt cgacgaacgt tcgtggacag aggctggggc aatggttgtg ggctattcgg      1260
aaaaggtagc ttaataacgt gtgctaagtt taagtgtgtg acaaaactgg aaggaaagat      1320
agtccaatat gaaaacttaa atattcagt gatagtcacc gtacacactg gagaccagca      1380
ccaagttgga aatgagacca gaacatgg aacaactgca accataacac ctcaagctcc      1440
cacgtcggaa atacagctga cagactacgg agctctaaca ttggattgtt cacctagaac      1500
agggctagac tttaatgaga tggtgttgtt gacaatgaaa aaaaatcat ggctcgtcca      1560 caaacaatgg tttctagact taccactgcc ttggacctcg ggggcttcaa catcccaaga      1620
gacttggaat agacaagact tgctggtcac atttaagaca gctcatgcaa aaaagcagga      1680
agtagtcgta ctaggatcac aagaaggagc aatgcacact gcgttgactg gagcgacaga      1740
```

```
aatccaaacg tctggaacga caacaatttt tgcaggacac ctgaaatgca gattaaaaat    1800
ggataaactg atttaaaaag ggatgtcata tgtaatgtgc acagggtcat tcaagttaga    1860
gaaggaagtg gctgagaccc agcatggaac tgttctagtg caggttaaat acgaaggaac    1920
agatgcacca tgcaagatcc ccttctcgtc ccaagatgag aagggagtaa cccagaatgg    1980
gagattgata cagccaacc ccatagtcac tgacaaagaa aaaccagtca acattgaagc     2040
ggagccacct tttggtgaga gctacattgt ggtaggagca ggtgaaaaag ctttgaaact    2100
aagctggttc aagaagggaa gcagtatagg gaaaatgttt gaagcaactg cccgtggagc    2160
acgaaggatg gccatcctgg gagacactgc atgggacttc ggttctatag gaggggtgtt    2220
cacgtctgtg ggaaaactga tacaccagat ttttgggact gcgtatggag ttttgttcag    2280
cggtgtttct tggaccatga agataggaat agggattctg ctgacatggc taggattaaa    2340
ctcaaggagc acgtcccttt caatgacgtg tatcgcagtt ggcatggtca cactgtacct    2400
aggagtcatg gttcaggcgg actcgggatg tgtaatcaac tggaaaggca gagaactcaa    2460
atgtggaagc ggcattttg tcaccaatga agtccacacc tggacagagc aatataaatt     2520
ccaggccgac tccctaaga gactatcagc ggccattggg aaggcatggg aggagggtgt     2580
gtgtggaatt cgatcagcca ctcgtctcga gaacatcatg tggaagcaaa tatcaaatga    2640
attaaaccac atcttacttg aaaatgacat gaaatttaca gtggtcgtag agacgttag     2700 tggaatcttg gcccaaggaa agaaaatgat taggccacaa cccatggaac acaaatactc    2760
gtggaaaagc tggggaaaag ccaaaatcat aggagcagat gtacagaata ccaccttcat    2820
catcgacggc ccaaacaccc cagaatgccc tgataaccaa agagcatgga acatttggga    2880
agttgaagac tatggatttg aattttcac gacaaacata tggttgaaat tgcgtgactc     2940
ctacactcaa gtgtgtgacc accggctaat gtcagctgcc atcaaggata gcaaagcagt    3000
ccatgctgac atggggtact ggatagaaag tgaaaagaac gagacttgga agttggcaag    3060
agcctccttc atagaagtta agacatgcat ctggccaaaa tcccacactc tatggagcaa    3120
tggagtcctg gaaagtgaga tgataatccc aaagatatat ggaggaccaa tatctcagca    3180
caactacaga ccaggatatt tcacacaaac agcagggccg tggcacttgg gcaagttaga    3240
actagatttt gatttatgtg aaggtaccac tgttgttgtg gatgaacatt gtggaaatcg    3300
aggaccatct cttagaacca caacagtcac aggaaagaca atccatgaat ggtgctgtag    3360
atcttgcacg ttaccccccc tacgtttcaa aggagaagac gggtgctggt acggcatgga    3420
aatcagacca gtcaaggaga aggaagagaa cctagttaag tcaatggtct ctgcagggtc    3480
aggagaagtg gacagttttt cactaggact gctatgcata tcaataatga tcgaagaggt    3540
aatgagatcc agatggagca gaaaaatgct gatgactgga acattggctg tgttcctcct    3600
tctcacaatg ggacaattga catggaatga tctgatcagg ctatgtatca tggttggagc    3660
caacgcttca gacaagatgg ggatgggaac aacgtaccta gctttgatgg ccactttcag    3720
aatgagacca atgttcgcag tcgggctact gtttcgcaga ttaacatcta gagaagttct    3780
tcttcttaca gttggattga gtctggtggc atctgtagaa ctaccaaatt ccttagagga    3840 gctagggat ggacttgcaa tgggcatcat gatgttgaaa ttactgactg atttcagtc     3900 acatcagcta tgggctacct tgctgtcttt aacatttgtc aaaacaactt tttcattgca    3960
ctatgcatgg aagacaatgg ctatgatact gtcaattgta tctctcttcc ctttatgcct    4020
gtccacgact tctcaaaaaa caacatggct tccggtgttg ctgggatctc ttggatgcaa    4080
```

```
accactaacc atgtttctta taacagaaaa caaaatctgg ggaaggaaaa gctggcctct    4140
caatgaagga attatggctg ttggaatagt tagcattctt ctaagttcac ttctcaagaa    4200
tgatgtgcca ctagctggcc cactaatagc tggaggcatg ctaatagcat gttatgtcat    4260
atctggaagc tcggccgatt tatcactgga gaaagcggct gaggtctcct gggaagaaga    4320
agcagaacac tctggtgcct cacacaacat actagtggag gtccaagatg atggaaccat    4380
gaagataaag gatgaagaga gagatgacac actcaccatt ctcctcaaag caactctgct    4440
agcaatctca ggggtatacc caatgtcaat accggcgacc ctctttgtgt ggtattttg    4500 gcagaaaaag aaacagagat caggagtgct atgggacaca cccagccctc cagaagtgga    4560
aagagcagtc cttgatgatg catttatag aattctccaa agaggattgt tgggcaggtc    4620
tcaagtagga gtaggagttt ttcaagaagg cgtgttccac acaatgtggc acgtcaccag    4680
gggagctgtc ctcatgtacc aagggaagag actggaacca agttgggcca gtgtcaaaaa    4740
agacttgatc tcatatggag gaggttggag gtttcaagga tcctggaacg cgggagaaga    4800
agtgcaggtg attgctgttg aaccggggaa gaaccccaaa aatgtacaga cagcgccggg    4860
taccttcaag acccctgaag gcgaagttgg agccatagct ctagactta aacccggcac    4920 atctggatct cctatcgtga acagagaggg aaaaatagta ggtctttatg gaaatggagt    4980
ggtgacaaca agtggtacct acgtcagtgc catagctcaa gctaaagcat cacaagaagg    5040
gcctctacca gagattgagg acgaggtgtt taggaaaaga aacttaacaa taatggacct    5100
acatccagga tcgggaaaaa caagaagata ccttccagcc atagtccgtg aggccataaa    5160
aagaaagctg cgcacgctag tcttagctcc cacaagagtt gtcgcttctg aaatggcaga    5220
ggcgctcaag ggaatgccaa taggtatca gacaacagca gtgaagagtg aacacacggg    5280
aaaggagata gttgacctta tgtgtcacgc cactttcact atgcgtctcc tgtctcctgt    5340
gagagttccc aattataata tgattatcat ggatgaagca cattttaccg atccagccag    5400
catagcagcc agagggtata tctcaacccg agtgggtatg ggtgaagcag ctgcgatttt    5460
catgacagcc actcccccgc gatcggtgga ggcctttcca cagagcaatg cagttatcca    5520
agatgaggaa agagacattc ctgaaagatc atggaactca ggctatgact ggatcactga    5580
tttcccaggt aaaacagtct ggtttgttcc aagcatcaaa tcaggaaatg acattgccaa    5640
ctgtttaaga aagaatggga aacgggtggt ccaattgagc agaaaaactt ttgacactga    5700
gtaccagaaa acaaaaaata cgactgggga ctatgttgtc acaacagaca tatccgaaat    5760
gggagcaaac ttccgagccg acagggtaat agaccgagg cggtgcctga aaccggtaat    5820
actaaaagat ggcccagagc gtgtcattct agccggaccg atgccagtga ctgtggctag    5880
cgccgcccag aggagaggaa gaattggaag gaaccaaaat aaggaaggcg atcagtatat    5940
ttacatggga cagcctctaa acaatgatga ggaccacgcc cattggacag aagcaaaaat    6000
gctccttgac aacataaaca caccagaagg gattatccca gccctctttg agccggagag    6060
agaaaagagt gcagcaatag acgggaata cagactacgg ggtgaagcga ggaaaacgtt    6120
cgtggagctc atgagaagag gagatctacc tgtctggcta tcctacaaag ttgcctcaga    6180
aggcttccag tactccgaca aaggtgtg ctttgatggg gaaaggaaca accaggtgtt    6240
ggaggagaac atggacgtgg agatctggac aaaagaagga gaaagaaaga aactacgacc    6300
ccgctggctg gatgccagaa catactctga cccactggct ctgcgcgaat tcaaagagtt    6360
cgcagcagga agaagaagcg tctcaggtga cctaatatta gaaataggga aacttccaca    6420
acatttaacg caaagggccc agaacgcctt ggacaatctg gttatgttgc acaactctga    6480
```

```
acaaggagga aaagcctata gacacgccat ggaagaacta ccagacacca tagaaacgtt    6540
aatgctccta gctttgatag ctgtgctgac tggtggagtg acgttgttct tcctatcagg    6600
aaggggtcta ggaaaaacat ccattggcct actctgcgtg attgcctcaa gtgcactgtt    6660
atggatggcc agtgtggaac cccattggat agcggcctct atcatactgg agttctttct    6720
gatggtgttg cttattccag agccggacag acagcgcact ccacaagaca accagctagc    6780
atacgtggtg ataggtctgt tattcatgat attgacagtg gcagccaatg agatgggatt    6840
actggaaacc acaagaagg  acctggggat tggtcatgca gctgctgaaa accaccatca    6900
tgctgcaatg ctggacgtag acctacatcc agcttcagcc tggactctct atgcagtggc    6960
cacaacaatt atcactccca tgatgagaca cacaattgaa aacacaacgg caaatatttc    7020
cctgacagct attgcaaacc aggcagctat attgatggga cttgacaagg gatggccaat    7080
atcaaagatg gacataggag ttccacttct cgccttgggg tgctattctc aggtgaaccc    7140
gctgacgctg acagcggcgg tattgatgct agtggctcat tatgccataa ttggacccgg    7200
actgcaagca aaagctacta gagaagctca aaaaaggaca gcagccggaa taatgaaaaa    7260
cccaactgtc gacgggatcg ttgcaataga tttggaccct gtggtttacg atgcaaaatt    7320
tgaaaaacag ctaggccaaa taatgttgtt gatactttgc acatcacaga tcctcctgat    7380
gcggaccaca tgggccttgt gtgaatccat cacactagcc actggacctc tgactacgct    7440
ttgggaggga tctccaggaa aattctggaa caccacgata gcggtgtcca tggcaaacat    7500
ttttagggga agttatctag caggagcagg tctggccttt tcattaatga aatctctagg    7560
aggaggtagg agaggcacgg gagcccaagg ggaaacactg ggagaaaaat ggaaaagaca    7620
gctaaaccaa ttgagcaagt cagaattcaa cacttacaaa aggagtggga ttatagaggt    7680
ggatagatct gaagccaaag aggggttaaa aagaggagaa acgactaaac acgcagtgtc    7740
gagaggaacg gccaaactga ggtggtttgt ggagaggaac cttgtgaaac cagaagggaa    7800
agtcatagac ctcggttgtg aagaggtgg  ctggtcatat tattgcgctg ggctgaagaa    7860
agtcacagaa gtgaaaggat acacgaaagg aggacctgga catgaggaac caatcccaat    7920
ggcaacctat ggatggaacc tagtaaagct atactccggg aaagatgtat tctttacacc    7980
acctgagaaa tgtgacaccc tcttgtgtga tattggtgag tcctctccga acccaactat    8040
agaagaagga agaacgttac gtgttctaaa gatggtggaa ccatggctca gaggaaacca    8100
attttgcata aaaattctaa atccctatat gccgagtgtg gtagaaactt tggagcaaat    8160
gcaaagaaaa catggaggaa tgctagtgcg aaatccactc tcaagaaact ccactcatga    8220
aatgtactgg gtttcatgtg aacaggaaa  cattgtgtca gcagtaaaca tgacatctag    8280
aatgctgcta aatcgattca atggctca   caggaagcca acatatgaaa gagacgtgga    8340
cttaggcgct ggaacaagac atgtggcagt agaaccagag gtggccaacc tagatatcat    8400
tggccagagg atagagaata taaaaatga  acacaaatca acatggcatt atgatgagga    8460
caatccatac aaaacatggg cctatcatgg atcatatgag gtcaagccat caggatcagc    8520
ctcatccatg gtcaatggtg tggtgagact gctaaccaaa ccatgggatg tcattcccat    8580
ggtcacacaa atagccatga ctgacaccac acccttgga  caacagaggg tgtttaaaga    8640
gaaagttgac acgcgtacac caaaagcgaa acgaggcaca gcacaaatta tggaggtgac    8700
agccaggtgg ttatggggtt ttctctctag aaacaaaaaa cccagaatct gcacaagaga    8760
ggagttcaca agaaaagtca ggtcaaacgc agctattgga gcagtgttcg ttgatgaaaa    8820
```

| | |
|---|---|
| tcaatggaac tcagcaaaag aggcagtgga agatgaacgg ttctgggacc ttgtgcacag | 8880 |
| agagagggag cttcataaac aaggaaaatg tgccacgtgt gtctacaaca tgatgggaaa | 8940 |
| gagagagaaa aaattaggag agttcggaaa ggcaaaagga agtcgcgcaa tatggtacat | 9000 |
| gtggttggga gcgcgctttt tagagtttga agcccttggt ttcatgaatg aagatcactg | 9060 |
| gttcagcaga gagaattcac tcagtggagt ggaaggagaa ggactccaca aacttggata | 9120 |
| catactcaga gacatatcaa agattccagg gggaaatatg tatgcagatg acacagccgg | 9180 |
| atgggacaca agaataacag aggatgatct tcagaatgag gccaaaatca ctgacatcat | 9240 |
| ggaacctgaa catgccctat tggccacgtc aatctttaag ctaacctacc aaacaaggt | 9300 |
| agtaagggtg cagagaccag cgaaaaatgg aaccgtgatg gatgtcatat ccagacgtga | 9360 |
| ccagagagga agtggacagg ttggaaccta tggcttaaac accttcacca acatggaggc | 9420 |
| ccaactaata agacaaatgg agtctgaggg aatcttttca cccagcgaat ggaaaccccc | 9480 |
| aaatctagcc gaaagagtcc tcgactggtt gaaaaaacat ggcaccgaga ggctgaaaag | 9540 |
| aatggcaatc agtggagatg actgtgtggt gaaaccaatc gatgacagat ttgcaacagc | 9600 |
| cttaacagct ttgaatgaca tgggaaaggt aagaaaagac ataccgcaat gggaaccttc | 9660 |
| aaaaggatgg aatgattggc aacaagtgcc tttctgttca caccatttcc accagctgat | 9720 |
| tatgaaggat gggagggaga tagtggtgcc atgccgcaac caagatgaac ttgtaggtag | 9780 |
| ggccagagta tcacaaggcg ccggatggag cttgagagaa actgcatgcc taggcaagtc | 9840 |
| atatgcacaa atgtggcagc tgatgtactt ccacaggaga gacttgagat tagcggctaa | 9900 |
| tgctatctgt tcagccgttc cagttgattg ggtcccaacc agccgcacca cctggtcgat | 9960 |
| ccatgcccac catcaatgga tgacaacaga agacatgttg tcagtgtgga ataggggtttg | 10020 |
| gatagagaaa aacccatgga tggaggacaa gactcatgtg tccagttggg aagacgttcc | 10080 |
| atacctagga aaagggaag atcaatggtg tggttcccta ataggcttaa cagcacgagc | 10140 |
| cacctgggcc accaacatac aagtggccat aaaccaagtg agaaggctca ttgggaatga | 10200 |
| gaattatcta gacttcatga catcaatgaa gagattcaaa aacgagagtg atcccgaagg | 10260 |
| ggcactctgg taagccaact cattcacaaa ataaaggaaa ataaaaaatc aaacaaggca | 10320 |
| agaagtcagg ccggattaag ccatagcacg gtaagagcta tgctgcctgt gagccccgtc | 10380 |
| caaggacgta aaatgaagtc aggccgaaag ccacggttcg agcaagccgt gctgcctgta | 10440 |
| gctccatcgt ggggatgtaa aaacccggga ggctgcaaac catggaagct gtacgcatgg | 10500 |
| ggtagcagac tagtggttag aggagacccc tcccaagaca caacgcagca gcggggccca | 10560 |
| acaccagggg aagctgtacc ctggtggtaa ggactagagg ttagaggaga ccccccgcac | 10620 |
| aacaacaaac agcatattga cgctgggaga ccagagatcc tgctgtctct ctacagcatc | 10680 |
| attccaggca cagaacgcca aaaatggaa tggtgctgtt gaatcaacag gttct | 10735 |

<210> SEQ ID NO 2
<211> LENGTH: 10723
<212> TYPE: DNA
<213> ORGANISM: Dengue virus type 2
<300> PUBLICATION INFORMATION:
<308> DATABASE ACCESSION NUMBER: NCBI/NC_001474
<309> DATABASE ENTRY DATE: 2011-11-17
<313> RELEVANT RESIDUES IN SEQ ID NO: (1)..(10723)

<400> SEQUENCE: 2

| | |
|---|---|
| agttgttagt ctacgtggac cgacaaagac agattctttg agggagctaa gctcaacgta | 60 |
| gttctaacag ttttttaatt agagagcaga tctctgatga ataaccaacg gaaaaaggcg | 120 |

```
aaaaacacgc ctttcaatat gctgaaacgc gagagaaacc gcgtgtcgac tgtgcaacag    180
ctgacaaaga gattctcact tggaatgctg cagggacgag gaccattaaa actgttcatg    240
gccctggtgg cgttccttcg tttcctaaca atcccaccaa cagcagggat attgaagaga    300
tggggaacaa ttaaaaaatc aaaagctatt aatgttttga gagggttcag gaaagagatt    360
ggaaggatgc tgaacatctt gaataggaga cgcagatctg caggcatgat cattatgctg    420
attccaacag tgatggcgtt ccatttaacc acacgtaacg gagaaccaca catgatcgtc    480
agcagacaag agaaagggaa aagtcttctg tttaaaacag aggatggcgt gaacatgtgt    540
accctcatgg ccatggacct tggtgaattg tgtgaagaca caatcacgta caagtgtccc    600
cttctcaggc agaatgagcc agaagacata gactgttggt gcaactctac gtccacgtgg    660
gtaacttatg ggacgtgtac caccatggga gaacatagaa gagaaaaaag atcagtggca    720
ctcgttccac atgtgggaat gggactggag acacgaactg aaacatggat gtcatcagaa    780
ggggcctgga acatgtcca gagaattgaa acttggatct tgagacatcc aggcttcacc    840
atgatggcag caatcctggc atacaccata ggaacgacac atttccaaag agccctgatt    900
ttcatcttac tgacagctgt cactccttca atgacaatgc gttgcatagg aatgtcaaat    960
agagactttg tggaaggggt ttcaggagga agctgggttg acatagtctt agaacatgga    1020
agctgtgtga cgacgatggc aaaaaacaaa ccaacattgg attttgaact gataaaaaca    1080
gaagccaaac agcctgccac cctaaggaag tactgtatag aggcaaagct aaccaacaca    1140
acaacagaat ctcgctgccc aacacaaggg gaacccagcc taaatgaaga gcaggacaaa    1200
aggttcgtct gcaaacactc catggtagac agaggatggg gaaatggatg tggactattt    1260
ggaaagggag gcattgtgac ctgtgctatg ttcagatgca aaaagaacat ggaaggaaaa    1320
gttgtgcaac cagaaaactt ggaatacacc attgtgataa cacctcactc aggggaagag    1380
catgcagtcg gaaatgacac aggaaaacat ggcaaggaaa tcaaaataac accacagagt    1440
tccatcacag aagcagaatt gacaggttat ggcactgtca caatggagtg ctctccaaga    1500
acgggcctcg acttcaatga gatggtgttg ctgcagatgg aaaataaagc ttggctggtg    1560
cacaggcaat ggttcctaga cctgccgtta ccatggttgc ccggagcgga cacacaaggg    1620
tcaaattgga tacagaaaga gacattggtc actttcaaaa atccccatgc gaagaaacag    1680
gatgttgttg ttttaggatc ccaagaaggg gccatgcaca cagcacttac aggggccaca    1740
gaaatccaaa tgtcatcagg aaacttactc ttcacaggac atctcaagtg caggctgaga    1800
atggacaagc tacagctcaa aggaatgtca tactctatgt gcacaggaaa gtttaaagtt    1860
gtgaaggaaa tagcagaaac acaacatgga acaatagtta tcagagtgca atatgaaggg    1920
gacggctctc catgcaagat cccttttgag ataatggatt tggaaaaaag acatgtctta    1980
ggtcgcctga ttacagtcaa cccaattgtg acagaaaaag atagcccagt caacatagaa    2040
gcagaacctc cattcggaga cagctacatc atcataggag tagagccggg acaactgaag    2100
ctcaactggt ttaagaaagg aagttctatc ggccaaatgt ttgagacaac aatgaggggg    2160
gcgaagagaa tggccatttt aggtgacaca gcctggatt ttggatcctt gggaggagtg    2220
tttacatcta taggaaaggc tctccaccaa gtctttggag caatctatgg agctgccttc    2280
agtggggttt catggactat gaaaatcctc ataggagtca ttatcacatg gataggaatg    2340
aattcacgca gcacctcact gtctgtgaca ctagtattgg tgggaattgt gacactgtat    2400
ttgggagtca tggtgcaggc cgatagtggt tgcgttgtga gctggaaaaa caaagaactg    2460
```

```
aaatgtggca gtgggatttt catcacagac aacgtgcaca catggacaga acaatacaag    2520
ttccaaccag aatcccttc aaaactagct tcagctatcc agaaagccca tgaagagggc     2580
atttgtggaa tccgctcagt aacaagactg gagaatctga tgtggaaaca aataacacca    2640
gaattgaatc acattctatc agaaaatgag gtgaagttaa ctattatgac aggagacatc    2700
aaaggaatca tgcaggcagg aaaacgatct ctgcggcctc agcccactga gctgaagtat    2760
tcatggaaaa catggggcaa agcaaaaatg ctctctacag agtctcataa ccagaccttt    2820
ctcattgatg gccccgaaac agcagaatgc cccaacacaa atagagcttg gaattcgttg    2880
gaagttgaag actatggctt tggagtattc accaccaata tatggctaaa attgaaagaa    2940
aaacaggatg tattctgcga ctcaaaactc atgtcagcgg ccataaaaga caacagagcc    3000
gtccatgccg atatgggtta ttggatagaa agtgcactca atgacacatg gaagatagag    3060
aaagcctctt tcattgaagt taaaaactgc cactggccaa aatcacacac cctctggagc    3120
aatggagtgc tagaaagtga gatgataatt ccaagaatc tcgctggacc agtgtctcaa    3180
cacaactata gaccaggcta ccatacacaa ataacggac catggcatct aggtaagctt    3240
gagatggact ttgatttctg tgatggaaca acagtggtag tgactgagga ctgcggaaat    3300
agaggaccct ctttgagaac aaccactgcc tctggaaaac tcataacaga atggtgctgc    3360
cgatcttgca cattaccacc gctaagatac agaggtgagg atgggtgctg gtacgggatg    3420
gaaatcagac cattgaagga aaagaagag aatttggtca actccttggt cacagctgga    3480
catgggcagg tcgacaactt ttcactagga gtcttgggaa tggcattgtt cctggaggaa    3540
atgcttagga cccgagtagg aacgaaacat gcaatactac tagttgcagt ttcttttgtg    3600
acattgatca cagggaacat gtcctttaga gacctgggaa gagtgatggt tatggtaggc    3660
gccactatga cggatgacat aggtatgggc gtgacttatc ttgccctact agcagccttc    3720
aaagtcagac caactttgc agctggacta ctcttgagaa agctgacctc caaggaattg    3780
atgatgacta ctataggaat tgtactcctc tcccagagca ccataccaga gaccattctt    3840
gagttgactg atgcgttagc cttaggcatg atggtcctca aaatggtgag aaatatggaa    3900
aagtatcaat tggcagtgac tatcatggct atcttgtgcg tcccaaacgc agtgatatta    3960
caaaacgcat ggaaagtgag ttgcacaata ttggcagtgg tgtccgtttc cccactgctc    4020
ttaacatcct cacagcaaaa aacagattgg ataccattag cattgacgat caaaggtctc    4080
aatccaacag ctatttttct aacaaccctc tcaagaacca gcaagaaaag gagctggcca    4140
ttaaatgagg ctatcatggc agtcgggatg gtgagcattt tagccagttc tctcctaaaa    4200
aatgatattc ccatgacagg accattagtg gctggagggc tcctcactgt gtgctacgtg    4260
ctcactggac gatcggccga tttggaactg gagagagcag ccgatgtcaa atgggaagac    4320
caggcagaga tatcaggaag cagtccaatc ctgtcaataa caatatcaga agatggtagc    4380
atgtcgataa aaatgaaga ggaagaacaa acactgacca tactcattag aacaggattg    4440
ctggtgatct caggacttt tcctgtatca ataccaatca cggcagcagc atggtacctg    4500
tgggaagtga agaaacaacg ggccggagta ttgtgggatg ttccttcacc cccacccatg    4560
ggaaaggctg aactgaaga tggagcctat agaattaagc aaaaagggat tcttggatat    4620
tcccagatcg gagccggagt ttacaaagaa ggaacattcc atacaatgtg gcatgtcaca    4680
cgtggcgctg ttctaatgca taaggaaag aggattgaac catcatgggc ggacgtcaag    4740
aaagacctaa tatcatatgg aggaggctgg aagttagaag gagaatggaa ggaaggagaa    4800
gaagtccagg tattggcact ggagcctgga aaaaatccaa gagccgtcca aacgaaacct    4860
```

```
ggtcttttca aaaccaacgc cggaacaata ggtgctgtat ctctggactt ttctcctgga      4920
acgtcaggat ctccaattat cgacaaaaaa ggaaaagttg tgggtcttta tggtaatggt      4980
gttgttacaa ggagtggagc atatgtgagt gctatagccc agactgaaaa aagcattgaa      5040
gacaacccag agatcgaaga tgacattttc gaaagagaa gactgaccat catggacctc       5100 caccccaggag cgggaaagac gaagagatac cttccggcca tagtcagaga agctataaaa     5160
cggggtttga gaacattaat cttggccccc actagagttg tggcagctga aatggaggaa      5220
gcccttagag gacttccaat aagataccag accccagcca tcagagctga gcacaccggg      5280
cgggagattg tggacctaat gtgtcatgcc acatttacca tgaggctgct atcaccagtt      5340
agagtgccaa actacaacct gattatcatg gacgaagccc atttcacaga cccagcaagt      5400
atagcagcta gaggatacat ctcaactcga gtggagatgg gtgaggcagc tgggattttt      5460
atgacagcca ctccccgggg aagcagagac ccatttcctc agagcaatgc accaatcata      5520
gatgaagaaa gagaaatccc tgaacgttcg tggaattccg acatgaatg ggtcacggat       5580 tttaaaggga agactgtttg gttcgttcca agtataaaag caggaaatga tatagcagct      5640
tgcctgagga aaaatggaaa gaaagtgata caactcagta ggaagacctt tgattctgag      5700
tatgtcaaga ctagaaccaa tgattgggac ttcgtggtta caactgacat ttcagaaatg      5760
ggtgccaatt tcaaggctga gagggttata gacccccagac gctgcatgaa accagtcata    5820
ctaacagatg gtgaagagcg ggtgattctg gcaggaccta tgccagtgac ccactctagt     5880
gcagcacaaa aagagggggag aataggaaga aatccaaaaa atgagaatga ccagtacata     5940
tacatggggg aacctctgga aaatgatgaa gactgtgcac actggaaaga agctaaaatg     6000
ctcctagata acatcaacac gccagaagga atcattccta gcatgttcga accagagcgt      6060
gaaaaggtgg atgccattga tggcgaatac cgcttgagag gagaagcaag gaaaaccttt      6120
gtagacttaa tgagaagagg agacctacca gtctggttgg cctacagagt ggcagctgaa      6180
ggcatcaact acgcagacag aaggtggtgt tttgatggag tcaagaacaa ccaaatccta      6240
gaagaaaacg tggaagttga atctggaca aaagaagggg aaaggaagaa attgaaaccc       6300
agatggttgg atgctaggat ctattctgac ccactggcgc taaaagaatt taaggaattt      6360
gcagccggaa gaaagtctct gaccctgaac ctaatcacag aaatgggtag gctcccaacc      6420
ttcatgactc agaaggcaag agacgcactg gacaacttag cagtgctgca cacggctgag      6480
gcaggtggaa gggcgtacaa ccatgctctc agtgaactgc cggagaccct ggagacattg      6540
cttttactga cacttctggc tacagtcacg ggagggatct ttttattctt gatgagcgga      6600 agggcatag ggaagatgac cctgggaatg tgctgcataa tcacggctag catcctccta       6660
tggtacgcac aaatacagcc acactggata gcagcttcaa taatactgga gttttttctc      6720
atagttttgc ttattccaga acctgaaaaa cagagaacac cccaagacaa ccaactgacc      6780
tacgttgtca tagccatcct cacagtggtg gccgcaacca tggcaaacga gatgggtttc      6840
ctagaaaaaa cgaagaaaga tctcggattg ggaagcattg caacccagca acccgagagc      6900
aacatcctgg acatagatct acgtcctgca tcagcatgga cgctgtatgc cgtggccaca      6960
acatttgtta caccaatgtt gagacatagc attgaaaatt cctcagtgaa tgtgtcccta     7020
acagctatag ccaaccaagc cacagtgtta atgggtctcg ggaaggatg gccattgtca      7080 aagatggaca tcggagttcc ccttctcgcc attggatgct actcacaagt caaccccata     7140
actctcacag cagctctttt cttattggta gcacattatg ccatcatagg gccaggactc    7200
```

```
caagcaaaag caaccagaga agctcagaaa agagcagcgg cgggcatcat gaaaaaccca    7260
actgtcgatg gaataacagt gattgaccta gatccaatac cttatgatcc aaagtttgaa    7320
aagcagttgg gacaagtaat gctcctagtc ctctgcgtga ctcaagtatt gatgatgagg    7380
actacatggg ctctgtgtga ggctttaacc ttagctaccg ggcccatctc cacattgtgg    7440
gaaggaaatc cagggaggtt ttggaacact accattgcgg tgtcaatggc taacattttt    7500
agagggagtt acttggccgg agctggactt ctcttttcta ttatgaagaa cacaaccaac    7560
acaagaaggg gaactggcaa cataggagag acgcttggag agaaatggaa aagccgattg    7620
aacgcattgg gaaaaagtga attccagatc tacaagaaaa gtggaatcca ggaagtggat    7680
agaaccttag caaaagaagg cattaaaaga ggagaaacgg accatcacgc tgtgtcgcga    7740
ggctcagcaa aactgagatg gttcgttgag agaaacatgg tcacaccaga agggaaagta    7800
gtggacctcg gttgtggcag aggaggctgg tcatactatt gtggaggact aaagaatgta    7860
agagaagtca aaggcctaac aaaaggagga ccaggacacg aagaacccat ccccatgtca    7920
acatatgggt ggaatctagt gcgtcttcaa agtggagttg acgttttctt catcccgcca    7980
gaaaagtgtg acacattatt gtgtgacata ggggagtcat caccaaatcc cacagtggaa    8040
gcaggacgaa cactcagagt ccttaactta gtagaaaatt ggttgaacaa caacactcaa    8100
ttttgcataa aggttctcaa cccatatatg ccctcagtca tagaaaaaat ggaagcacta    8160
caaaggaaat atggaggagc cttagtgagg aatccactct cacgaaactc cacacatgag    8220
atgtactggg tatccaatgc ttccgggaac atagtgtcat cagtgaacat gatttcaagg    8280
atgttgatca acagatttac aatgagatac aagaaagcca cttacgagcc ggatgttgac    8340
ctcggaagcg gaacccgtaa catcgggatt gaaagtgaga taccaaacct agatataatt    8400
gggaaaagaa tagaaaaaat aaagcaagag catgaaacat catggcacta tgaccaagac    8460
caccccataca aaacgtgggc ataccatggt agctatgaaa caaaacagac tggatcagca    8520
tcatccatgg tcaacggagt ggtcaggctg ctgacaaaac cttgggacgt cgtccccatg    8580
gtgacacaga tggcaatgac agacacgact ccatttggac aacagcgcgt ttttaaagag    8640
aaagtggaca cgagaaccca agaaccgaaa gaaggcacga agaaactaat gaaaataaca    8700
gcagagtggc tttggaaaga attagggaag aaaaagacac ccaggatgtg caccagagaa    8760
gaattcacaa gaaaggtgag aagcaatgca gccttggggg ccatattcac tgatgagaac    8820
aagtggaagt cggcacgtga ggctgttgaa gatagtaggt tttgggagct ggttgacaag    8880
gaaaggaatc tccatcttga aggaaagtgt gaaacatgtg tgtacaacat gatgggaaaa    8940
agagagaaga agctagggga attcggcaag gcaaaaggca gcagagccat atggtacatg    9000
tggcttggag cacgcttctt agagtttgaa gccctaggat tcttaaatga agatcactgg    9060
ttctccagag agaactccct gagtggagtg aaggagaag ggctgcacaa gctaggttac    9120
attctaagag acgtgagcaa gaaagaggga ggagcaatgt atgccgatga caccgcagga    9180
tgggatacaa gaatcacact agaagaccta aaaaatgaag aaatggtaac aaaccacatg    9240
gaaggagaac acaagaaact agccgaggcc attttcaaac taacgtacca aaacaaggtg    9300
gtgcgtgtgc aaagaccaac accaagaggc acagtaatgg acatcatatc gagaagagac    9360
caaagaggta gtggacaagt tggcacctat ggactcaata ctttcaccaa tatggaagcc    9420
caactaatca gacagatgga gggagaagga gtctttaaaa gcattcagca cctaacaatc    9480
acagaagaaa tcgctgtgca aaactggtta gcaagagtgg ggcgcgaaag gttatcaaga    9540
atggccatca gtgagatga ttgtgttgtg aaacctttag atgacaggtt cgcaagcgct    9600
```

| | | | | |
|---|---|---|---|---|
| ttaacagctc | taaatgacat | gggaaagatt | aggaaagaca | tacaacaatg ggaaccttca | 9660 |
| agaggatgga | atgattggac | acaagtgccc | ttctgttcac | accatttcca tgagttaatc | 9720 |
| atgaaagacg | tcgcgtact | cgttgttcca | tgtagaaacc | aagatgaact gattggcaga | 9780 |
| gcccgaatct | cccaaggagc | agggtggtct | ttgcgggaga | cggcctgttt ggggaagtct | 9840 |
| tacgcccaaa | tgtggagctt | gatgtacttc | cacagacgcg | acctcaggct ggcggcaaat | 9900 |
| gctatttgct | cggcagtacc | atcacattgg | gttccaacaa | gtcgaacaac ctggtccata | 9960 |
| catgctaaac | atgaatggat | gacaacggaa | gacatgctga | cagtctggaa cagggtgtgg | 10020 |
| attcaagaaa | acccatggat | ggaagacaaa | actccagtgg | aatcatggga ggaaatccca | 10080 |
| tacttgggga | aaagagaaga | ccaatggtgc | ggctcattga | ttgggttaac aagcagggcc | 10140 |
| acctgggcaa | agaacatcca | agcagcaata | aatcaagtta | gatcccttat aggcaatgaa | 10200 |
| gaatacacag | attacatgcc | atccatgaaa | agattcagaa | gagaagagga agaagcagga | 10260 |
| gttctgtggt | agaaagcaaa | actaacatga | acaaggcta | gaagtcaggt cggattaagc | 10320 |
| catagtacgg | aaaaaactat | gctacctgtg | agccccgtcc | aaggacgtta aaagaagtca | 10380 |
| ggccatcata | aatgccatag | cttgagtaaa | ctatgcagcc | tgtagctcca cctgagaagg | 10440 |
| tgtaaaaaat | ccgggaggcc | acaaaccatg | gaagctgtac | gcatggcgta gtggactagc | 10500 |
| ggttagagga | gacccctccc | ttacaaatcg | cagcaacaat | gggggcccaa ggcgagatga | 10560 |
| agctgtagtc | tcgctggaag | gactagaggt | tagaggagac | ccccccgaaa caaaaaacag | 10620 |
| catattgacg | ctgggaaaga | ccagagatcc | tgctgtctcc | tcagcatcat tccaggcaca | 10680 |
| gaacgccaga | aaatggaatg | gtgctgttga | atcaacaggt | tct | 10723 |

<210> SEQ ID NO 3
<211> LENGTH: 10707
<212> TYPE: DNA
<213> ORGANISM: Dengue virus type 3
<300> PUBLICATION INFORMATION:
<308> DATABASE ACCESSION NUMBER: NCBI/NC_001475
<309> DATABASE ENTRY DATE: 2011-11-17
<313> RELEVANT RESIDUES IN SEQ ID NO: (1)..(10707)

<400> SEQUENCE: 3

| | | | | |
|---|---|---|---|---|
| agttgttagt | ctacgtggac | cgacaagaac | agtttcgact | cggaagcttg cttaacgtag | 60 |
| tgctgacagt | tttttattag | agagcagatc | tctgatgaac | aaccaacgga agaagacggg | 120 |
| aaaaccgtct | atcaatatgc | tgaaacgcgt | gagaaaccgt | gtgtcaactg gatcacagtt | 180 |
| ggcgaagaga | ttctcaaaag | gactgctgaa | cggccaggga | ccaatgaaat tggttatggc | 240 |
| gttcatagct | ttcctcagat | ttctagccat | tccaccaaca | gcaggagtct tggctagatg | 300 |
| gggaaccttc | aagaagtcgg | gggccattaa | ggtcctgaaa | ggcttcaaga aggagatctc | 360 |
| aaacatgctg | agcataatca | accaacggaa | aaagacatcg | ctctgtctca tgatgatatt | 420 |
| gccagcagca | cttgctttcc | acttgacttc | acgagatgga | gagccgcgca tgattgtggg | 480 |
| gaagaatgaa | agaggtaaat | ccctactttt | taagacagcc | tctggaatca acatgtgcac | 540 |
| actcatagcc | atggatttgg | gagagatgtg | tgatgacacg | gtcacttaca aatgccccca | 600 |
| cattaccgaa | gtggaacctg | aagacattga | ctgctggtgc | aaccttacat caacatgggt | 660 |
| gacttatgga | acgtgcaatc | aagctggaga | gcatagacgc | gacaagagat cagtggcgtt | 720 |
| agctccccat | gtcggcatgg | gactggacac | acgcacccaa | acctgatgt cggctgaagg | 780 |
| agcttggaga | caagtcgaga | aggtagagac | atgggcccctt | aggcacccag ggttcaccat | 840 |

```
actagcccta tttctcgccc attacatagg cacttccctg acccagaagg tggttatttt    900
catattatta atgctggtca ccccatccat gacaatgaga tgtgtgggag taggaaacag    960
agattttgtg gaagggctat caggagctac gtgggttgac gtggtgctcg agcacggggg   1020
gtgtgtgact accatggcta agaacaagcc cacgctggat atagagcttc agaagaccga   1080
ggccacccaa ctggcgaccc taaggaagct atgcattgag gggaaaatta ccaacataac   1140
aactgactca agatgtccta cccaagggga agcggttttg cctgaggagc aggaccagaa   1200
ctacgtgtgt aagcatacat acgtagacag aggttggggg aacggttgtg gtttgtttgg   1260
caaaggaagc ttggtaacat gtgcgaaatt tcaatgcctg gaaccaatag agggaaaagt   1320
ggtgcaatat gagaacctca atacaccgt catcattaca gtgcacacag agaccaaca    1380
ccaggtggga aatgaaacgc aaggagtcac ggctgagata cacctcagg catcaaccac    1440
tgaagccatc ttgcctgaat atggaaccct tgggctagaa tgctcaccac ggacaggttt   1500
ggatttcaat gaaatgatct tactaacaat gaagaacaaa gcatggatgg tacatagaca   1560
atggttcttt gacctacctc taccatgggc atcaggagct acaacagaaa caccaacctg   1620
gaacaggaag gagcttcttg tgacattcaa aaacgcacat gcgaaaaaac aagaagtagt   1680
tgtccttgga tcgcaagagg gagcaatgca taccgcactg acaggagcta cagaaatcca   1740
aaactcagga ggcacaagca ttttcgcggg gcacttaaaa tgtagactta agatggacaa   1800
attggaactc aaggggatga gctatgcaat gtgcacgaat acctttgtgt tgaagaaaga   1860
agtctcagaa acgcagcacg gacaatact cattaaggtt gagtacaaag gggaagatgc    1920
accttgcaag attccctttt ccacagagga tggacaaggg aaagctcata atggcagact   1980
gatcacagcc aaccctgtgg tgactaagaa ggaggagcct gtcaatattg aggctgaacc   2040
tccttttggg gaaagcaata tagtaattgg aattggagac aacgccttga aaatcaactg   2100
gtacaagaag gggagctcga ttgggaagat gttcgaggcc actgaaaggg gtgcaaggcg   2160
catggccatc ttgggagaca cagcttggga ctttggatca gtgggtggtg ttctgaactc   2220
attaggcaaa atggtgcacc aaatatttgg aagtgcttat acagccctgt tcagtggagt   2280
ctcttgggtg atgaaaattg gaataggtgt cctcttgact tggatagggt tgaattcaaa   2340
aaacacatcc atgtcatttt catgcattgc gataggaatc attacactct atctgggagc   2400
tgtggtacaa gctgacatgg ggtgtgtcat aaactggaag ggcaaagaac tcaaatgtgg   2460
aagcggaatt ttcgtcacca atgaggtcca tacctggaca gagcaataca aattccaagc   2520
agactcccca aaaagattgg caacagccat tgcaggcgcc tgggagaatg gagtgtgtgg   2580
aattaggtca acaaccagaa tggagaatct cttgtggaag caaatagcca atgaactgaa   2640
ctacatatta tgggaaaaca atatcaaatt aacggtagtt gtgggcgata cacttgggt    2700
cttagagcaa gggaaaagaa cactaacacc acaacccatg gagctaaaat actcatggaa   2760
aacgtgggga aaggcaaaaa tagtgacagc tgaaacacaa aattcctctt tcataataga   2820
cgggccaaac acaccggagt gtccaagtgc ctcaagagca tggaatgtgt gggaggtgga   2880
agattacggg ttcggagtct tcacaaccaa catatggctg aaactccgag aggtctacac   2940
ccaactatgt gaccataggc taatgtcggc agctgtcaag gatgagaggg ccgtgcatgc   3000
cgacatgggc tactggatag aaagccaaaa gaatggaagt tggaagctag aaaaagcatc   3060
cctcatagag gtaaaaacct gcacatggcc aaaatcacac actctctgga ctaatggtgt   3120
gctagagagt gacatgatca tcccaaagag tctagctggt cctatctcac aacacaacta   3180
caggcccggg taccacaccc aaacggcagg accctggcac ttaggaaaat tggagctgga   3240
```

```
cttcaactac tgtgaaggaa caacagttgt catcacagaa agctgtggga caagaggccc   3300
atcattgaga acaacaacag tgtcagggaa gttgatacac gaatggtgtt gccgctcgtg   3360
cacacttccc ccctgcgat acatgggaga agacggctgc tggtatggca tggaaatcag    3420
acccatcagt gagaaagaag agaacatggt aaagtcttta gtctcagcgg aagtggaaa    3480 ggtggacaac ttcacaatgg gtgtcttgtg tttggcaatc ctctttgaag aggtgttgag   3540
aggaaaattt gggaagaaac acatgattgc aggggttttc tttacgtttg tgctccttct   3600
ctcagggcaa ataacatgga gagacatggc gcacacacta ataatgatcg gtccaacgc    3660 ctctgacagg atgggaatgg gcgtcaccta cctagctcta attgcaacat ttaaaatcca   3720
gccattcttg gctttgggat ttttcctaag aaagctgaca tctagagaaa atttattgtt   3780
aggagttggg ttggccatgg caacaacgtt acaactgcca gaggacattg aacaaatggc   3840
aaatggagtc gctctggggc tcatggctct taaactgata acacaatttg aaacatacca   3900
attgtggacg gcattagtct ccttaacgtg ttcaaacaca attttacgt tgactgttgc    3960 ctggagaaca gccactctga ttttggccgg agtttcgctt ttaccagtgt gccagtcttc   4020
aagcatgagg aaaacagatt ggctcccaat gacagtggca gctatgggag ttccaccct    4080 tccactttt attttagct tgaaagacac actcaaaagg agaagctggc cactgaatga    4140 agggtgatg gctgttgggc ttgtgagcat tctggccagt tctctcctta gaaatgatgt    4200
gcccatggct ggaccattag tggccggggg cttgctgata gcgtgctacg tcataactgg    4260
cacgtcagcg gacctcactg tagaaaaagc cccagatgta acatgggagg aagaggctga   4320
gcagacagga gtgtcccaca acttaatgat cacagttgat gatgatggaa caatgagaat   4380
aaaagatgat gagactgaga acatcctaac agtgctttta aaaacagcat tactaatagt   4440
atcaggcatt tttccatact ccatacccgc aacattgttg gtctggcaca cttggcaaaa   4500
acaaacccaa agatccggcg ttttatggga cgtacccagc cccccagaga cacagaaagc   4560
agaactggaa gaaggggttt ataggatcaa acagcaagga atttttggga aacccaagt    4620 aggggttgga gtacagaaag aaggagtctt ccacaccatg tggcacgtca caagagggc    4680 agtgttgaca cataatggga aaagactgga accaaactgg gctagtgtga aaaagatct    4740 gatttcatat ggaggaggat ggagactgag cgcacaatgg caaaagggg aggaggtgca    4800 ggttattgcc gtagagccag ggaagaaccc aaagaacttt caaccacgc caggcactt     4860 ccagactact acaggggaaa taggagcaat tgcactggat ttcaagcctg aacttcagg    4920 atctcctatc ataaatagag agggaaaggt agtgggactg tatggcaatg gagtggttac   4980
aaagaatggt ggctatgtca gcggaatagc gcaaacaaat gcagaaccag atggaccgac   5040
accagagttg gaagaagaga tgttcaaaaa gcgaaacctg accataatgg atcttcatcc   5100
tgggtcagga aagacacgga aataccttcc agctattgtc agagaggcaa tcaagagacg   5160
tttaagaacc ttaattttgg caccgacaag ggtggttgca gctgagatgg aagaagcatt   5220
gaaagggctc ccaataaggt accaaacaac agcaacaaaa tctgaacaca caggaagaga   5280
gattgttgat ctaatgtgcc acgcaacgtt cacaatgcgt ttgctgtcac cagttagggt   5340
tccaaattac aacttgataa taatggatga ggcccatttc acagaccag ccagtatagc    5400 ggctagaggg tacatatcaa ctcgtgttgg aatgggagag gcagccgcaa tcttcatgac   5460
agcaacaccc cctggaacag ctgatgcctt tcctcagagc aacgctccaa ttcaagatga   5520
agaaagggac ataccagaac gctcatggaa ttcaggcaat gaatggatta ccgacttcgc   5580
```

```
tgggaaaacg gtgtggtttg tccctagcat taaagccgga aatgacatag caaactgctt    5640
gcgaaaaaac gggaaaaaag tcattcaact tagtaggaag acttttgaca cagaatatca    5700
gaagactaaa ctgaatgatt gggactttgt ggtgacaact gacatttcag aaatgggggc    5760
caatttcaaa gcagatagag tgatcgaccc aagaagatgt ctcaaaccag tgatcttgac    5820
agatggacca gagcgggtga tcctggccgg accaatgcca gtcaccgcgg cgagtgctgc    5880
gcaaaggaga gggagagttg gcaggaaccc acaaaaagag aatgaccagt acatattcac    5940
gggccagcct ctcaacaatg atgaagacca tgctcactgg acagaagcaa aaatgctgct    6000
ggacaacatc aacacaccag aagggattat accagctctc tttgaaccag aaagggagaa    6060
gtcagccgcc atagacggtg agtatcgcct gaagggtgag tccaggaaga ctttcgtgga    6120
actcatgagg aggggtgacc ttccagtttg gttagcccat aaagtagcat cagaaggaat    6180
caaatacaca gatagaaaat ggtgcttttga tgggcaacgc aataatcaaa ttttagagga    6240
gaacatggat gtggaaattt ggacaaagga aggagaaaag aaaaaattga gacctaggtg    6300
gcttgatgcc cgcacttatt cagatccatt ggcactcaag gaattcaagg actttgcggc    6360
tggcagaaag tcaatcgccc ttgatcttgt gacagaaata ggaagagtgc cttcacatct    6420
agcccacaga acaagaaacg ctctggacaa tctggtgatg ctgcatacgt cagaagatgg    6480
cggtagggct tacaggcatg cggtggagga actaccagaa acaatggaaa cactcctact    6540
cttgggacta atgatcttgt tgacaggtgg agcaatgctt ttcttgatat caggtaaagg    6600
gattggaaag acttcaatag gactcatttg tgtaatcgct tccagcggca tgttgtggat    6660
ggccgaagtt ccactccaat ggatcgcgtc ggctatagtc ctggagtttt ttatgatggt    6720
gttgctcata ccagaaccag aaaagcagag aaccccccaa gacaaccaac tcgcatatgt    6780
cgtgatagge atacttacat tggctgcaac aatagcagcc aatgaaatgg gactgctgga    6840
aaccacaaag agagacttag gaatgtctaa ggagccaggt gttgtttctc aaccagcta    6900
tttggatgtg gacttgcacc cagcatcagc ctggacattg tacgccgtgg ccactacagt    6960
aataacacca atgttaagac ataccataga gaattctaca gcaaatgtgt ccctggcagc    7020
tatagccaac caggcagtgg tcctgatggg tttggacaaa ggatggccaa tatcaaaaat    7080
ggacttaggc gtgccactac tggcactggg ttgctattca caagtgaacc cactgactct    7140
aactgcggca gtacttttgc taatcacaca ttatgctatc ataggtccag attgcaagc    7200
aaaagccacc cgtgaagctc agaaaaggac agctgctgga ataatgaaga atccaacagt    7260
ggatgggata atgacaatag acctagattc tgtaatattt gattcaaaat ttgaaaaaca    7320
actgggacag gttatgctcc tggttttgtg cgcagtccaa ctcttgctaa tgagaacatc    7380
atgggccttg tgtgaagctt taactctagc tacaggacca ataacaacac tctgggaagg    7440
atcacctggt aagttctgga acaccacgat agctgtttcc atggcgaaca ttttttagagg    7500
gagctattta gcaggagctg gcttgctttt ctctattatg aaatcagttg gaacaggaaa    7560
aagaggaaca ggctcacaag gtgaaacttt aggagaaaaa tggaaaaaga aattaaatca    7620
attatcccgg aaagagtttg accttacaa gaaatctgga atcactgaag tggatagaac    7680
agaagccaaa gaagggttga aagaggaga caacacat catgccgtgt cccgaggtag    7740
cgcaaaactt caatggtttg tggaaagaaa catggtcgtt cccgaaggaa gagtcataga    7800
cttgggctgt ggaagaggag ctggtcata ttactgtgca ggactgaaaa agtcacaga    7860
agtgcgagga tacacaaaag gcggtccagg acacgaagaa ccagtaccta tgtctacata    7920
tgggatggaac atagttaagt taatgagcgg aaaggatgtg ttctatctcc cacctgaaaa    7980
```

```
gtgtgatacc ctgttgtgtg acattggaga atcttcacca agcccaacag tggaagagag    8040
cagaactata agagttttga agatggttga accatggcta aaaaacaacc agttttgcat    8100
taaagttttg aacccttaca tgccaactgt gattgagcac ctagaaagac tacaaaggaa    8160
acatggagga atgcttgtga gaaatccact ttcacgaaac tccacgcacg aaatgtactg    8220
gatatctaat ggcacaggta acattgtctc ttcagtcaac atggtgtcta gattgctact    8280
gaacaggttc acgatgacac acaggagacc caccatagag aaagatgtgg atttaggagc    8340
aggaactcga catgttaatg cggaaccaga acacccaac atggatgtca ttggggaaag    8400
aataaaaagg atcaaggagg agcataattc aacatggcac tatgatgacg aaaaccccta    8460
caaaacgtgg gcttaccatg gatcctatga agtcaaagcc acaggctcag cctcctccat    8520
gataaatgga gtcgtgaaac tcctcaccaa accatgggat gtggtgccca tggtgacaca    8580
gatggcaatg acagacacaa ctccatttgg ccagcagaga gtctttaaag agaaagtgga    8640
caccaggacg cccaggccca tgccagggac aagaaaggct atggagatca cagcggagtg    8700
gctctggaga accctgggaa ggaacaaaag acccagatta tgcacaaggg aagagtttac    8760
aaaaaaggtc agaactaacg cagccatggg cgccgttttc acagaggaga ccaatggga    8820 cagtgcgaaa gctgctgttg aggatgaaga attttggaaa cttgtggaca gagaacgtga    8880
actccacaaa ttgggcaaat gtggaagctg cgtttataac atgatgggca agagagagaa    8940
aaaacttgga gagtttggca aagcaaaagg cagtagagct atatggtaca tgtggttggg    9000
agccaggtac cttgagttcg aagcccttgg attcttaaat gaagaccact ggttctcgcg    9060
tgaaaactct tacagtggag tagaaggaga aggactgcac aagctaggct acatattaag    9120
ggacatttcc aagatacccg gaggagccat gtatgctgat gacacagctg ttgggacac    9180 aagaataaca gaagatgacc tgcacaatga ggaaaagatc atacagcaaa tggaccctga    9240
acacaggcag ttagcgaacg ctatattcaa gctcacatac caaaacaaag tggtcaaagt    9300
tcaacgaccg actccaacgg gcacggtaat ggatattata tctaggaaag accaaagggg    9360
cagtggacaa ctgggaactt atggcctgaa tacattcacc aacatggaag cccagttagt    9420
cagacaaatg gaaggagaag gtgtgctgac aaaggcagac ctcgagaacc ctcatctgct    9480
agagaagaaa atcacacaat ggttggaaac caaaggagtg gagaggttaa aaagaatggc    9540
cattagcggg gatgattgcg tggtgaaacc aatcgatgac aggttcgcta atgccctgct    9600
tgctttgaac gatatgggaa aggttcggaa agacatacct caatggcagc catcaaaggg    9660
atggcatgat tggcaacagg ttccttttctg ctcccaccac tttcatgaat tgatcatgaa    9720
agatggaaga aagttggtgg ttccctgcag accccaggac gaactaatag gaagagcaag    9780
aatctctcaa ggagcgggat ggagccttag agaaactgca tgtctgggga agcctacgc    9840 ccaaatgtgg agtctcatgt atttccacag aagagatctc agattagcat ccaacgccat    9900
atgttcagca gtaccagtcc actggggtcc cacaagtaga acgacatggt ctattcatgc    9960
tcaccatcag tggatgacta cagaagacat gcttactgtt tggaacaggg tgtggataga   10020
ggaaatccaa tggatggaag acaaaactcc agttacaact tgggaaaatg ttccatatct   10080
aggaaagaga gaagaccaat ggtgtggatc acttattggt ctcacttcca gagcaacctg   10140
ggcccagaac ataccacag caattcaaca ggtgagaagc ttataggca atgaagagtt   10200 cctggactac atgccttcaa tgaagagatt caggaaggaa gaggagtcgg agggagccat   10260
ttggtaaacg taggaagtgg aaaagaggct aactgtcagg ccaccttaag ccacagtacg   10320
```

| | | | | |
|---|---|---|---|---|
| gaagaagctg | tgctgcctgt | gagccccgtc | caaggacgtt | aaaagaagaa gtcaggcccc | 10380 |
| aaagccacgg | tttgagcaaa | ccgtgctgcc | tgtagctccg | tcgtggggac gtaaaacctg | 10440 |
| ggaggctgca | aactgtggaa | gctgtacgca | cggtgtagca | gactagcggt tagaggagac | 10500 |
| ccctcccatg | acacaacgca | gcagcggggc | ccgagcactg | agggaagctg tacctccttg | 10560 |
| caaaggacta | gaggttagag | gagaccccccc | gcaaataaaa | acagcatatt gacgctggga | 10620 |
| gagaccagag | atcctgctgt | ctcctcagca | tcattccagg | cacagaacgc cagaaaatgg | 10680 |
| aatggtgctg | ttgaatcaac | aggttct | | | 10707 |

<210> SEQ ID NO 4
<211> LENGTH: 10649
<212> TYPE: DNA
<213> ORGANISM: Dengue virus type 4
<300> PUBLICATION INFORMATION:
<308> DATABASE ACCESSION NUMBER: NCBI/NC_002640
<309> DATABASE ENTRY DATE: 2011-11-17
<313> RELEVANT RESIDUES IN SEQ ID NO: (1)..(10649)

<400> SEQUENCE: 4

| | | | | |
|---|---|---|---|---|
| agttgttagt | ctgtgtggac | cgacaaggac | agttccaaat | cggaagcttg cttaacacag | 60 |
| ttctaacagt | ttgtttgaat | agagagcaga | tctctgaaa | aatgaaccaa cgaaaaaagg | 120 |
| tggttagacc | acctttcaat | atgctgaaac | gcgagagaaa | ccgcgtatca accccctcaag | 180 |
| ggttggtgaa | gagattctca | accggacttt | tttctgggaa | aggacccctta cggatggtgc | 240 |
| tagcattcat | cacgttttg | cgagtccttt | ccatcccacc | aacagcaggg attctgaaga | 300 |
| gatggggaca | gttgaagaaa | ataaggcca | tcaagatact | gattggattc aggaaggaga | 360 |
| taggccgcat | gctgaacatc | ttgaacggga | gaaaaggtc | aacgataaca ttgctgtgct | 420 |
| tgattcccac | cgtaatggcg | ttttcccctca | gcacaagaga | tggcgaaccc ctcatgatag | 480 |
| tggcaaaaca | tgaaggggg | agacctctct | tgtttaagac | aacagaggg atcaacaaat | 540 |
| gcactctcat | tgccatggac | ttgggtgaaa | tgtgtgagga | cactgtcacg tataaatgcc | 600 |
| ccctactggt | caataccgaa | cctgaagaca | ttgattgctg | gtgcaacctc acgtctacct | 660 |
| gggtcatgta | tgggacatgc | acccagagcg | agaacggag | acgagagaag cgctcagtag | 720 |
| ctttaacacc | acattcagga | atgggattgg | aaacaagagc | tgagacatgg atgtcatcgg | 780 |
| aaggggcttg | gaagcatgct | cagagagtag | agagctggat | actcagaaac ccaggattcg | 840 |
| cgctcttggc | aggatttatg | gcttatatga | ttgggcaaac | aggaatccag cgaactgtct | 900 |
| tctttgtcct | aatgatgctg | gtcgccccat | cctacggaat | gcgatgcgta ggagtaggaa | 960 |
| acagagactt | tgtggaagga | gtctcaggtg | gagcatgggt | cgacctggtg ctagaacatg | 1020 |
| gaggatgcgt | cacaaccatg | gcccagggaa | aaccaaccct | tgattttgaa ctgactaaga | 1080 |
| caacagccaa | ggaagtggct | ctgttaagaa | cctattgcat | tgaagcctca atatcaaaca | 1140 |
| taactacggc | aacaagatgt | ccaacgcaag | gagagcctta | tctgaaagag gaacaggacc | 1200 |
| aacagtacat | ttgccggaga | gatgtggtag | acagagggtg | gggcaatggc tgtggcttgt | 1260 |
| ttggaaaagg | aggagttgtg | acatgtgcga | agttttcatg | ttcggggaag ataacaggca | 1320 |
| atttggtcca | aattgagaac | cttgaataca | cagtggttgt | aacagtccac aatgagacag | 1380 |
| cccatgcagt | aggaaatgac | acatccaatc | atggagttac | agccatgata actcccagt | 1440 |
| caccatcggt | ggaagtcaaa | ttgccggact | atggagaact | aacactcgat tgtgaaccca | 1500 |
| ggtctgaat | tgactttaat | gagatgattc | tgatgaaaat | gaaaagaaa acatggctcg | 1560 |
| tgcataagca | atggttttg | gatctgcctc | ttccatggac | agcaggagca gacacatcag | 1620 |

```
aggttcactg gaattacaaa gagagaatgg tgacatttaa ggttcctcat gccaagagac    1680
aggatgtgac agtgctggga tctcaggaag gagccatgca ttctgccctc gctggagcca    1740
cagaagtgga ctccggtgat ggaaatcaca tgtttgcagg acatcttaag tgcaaagtcc    1800
gtatggagaa attgagaatc aagggaatgt catacacgat gtgttcagga aagttttcaa    1860
ttgacaaaga gatggcagaa acacagcatg gacaacagt ggtgaaagtc aagtatgaag    1920
gtgctggagc tccgtgtaaa gtccccatag agataagaga tgtaaacaag gaaaagtgg    1980 ttgggcgtat catctcatcc acccctttgg ctgagaatac caacagtgta accaacatag    2040
aattagaacc cccctttggg gacagctaca tagtgatagg tgttggaaac agcgcattaa    2100
cactccattg gttcaggaaa gggagttcca ttggcaagat gtttgagtcc acatacagag    2160
gtgcaaaacg aatggccatt ctaggtgaaa cagcttggga ttttggttcc gttggtggac    2220
tgttcacatc attgggaaag gctgtgcacc aggttttgg aagtgtgtat acaaccatgt    2280
ttggaggagt ctcatggatg attagaatcc taattgggtt cttagtgttg tggattggca    2340
cgaactcgag gaacacttca atggctatga cgtgcatagc tgttggagga atcactctgt    2400
ttctgggctt cacagttcaa gcagacatgg gttgtgtggc gtcatggagt gggaaagaat    2460
tgaagtgtgg aagcggaatt tttgtggttg acaacgtgca cacttggaca gaacagtaca    2520
aatttcaacc agagtcccca gcgagactag cgtctgcaat attaaatgcc acaaagatg    2580 gggtctgtgg aattagatca accacgaggc tggaaaatgt catgtggaag caaataacca    2640
acgagctaaa ctatgttctc tgggaaggag gacatgacct cactgtagtg gctgggatg    2700 tgaaggggt gttgaccaaa ggcaagagag cactcacacc cccagtgagt gatctgaaat    2760
attcatggaa gacatgggga aaagcaaaaa tcttcacccc agaagcaaga aatagcacat    2820
ttttaataga cggaccagac acctctgaat gccccaatga acgaagagca tggaactctc    2880
ttgaggtgga agactatgga tttggcatgt tcacgaccaa catatggatg aaattccgag    2940
aaggaagttc agaagtgtgt gaccacaggt taatgtcagc tgcaattaaa gatcagaaag    3000
ctgtgcatgc tgacatgggt tattggatag agagctcaaa aaaccagacc tggcagatag    3060
agaaagcatc tcttattgaa gtgaaaacat gtctgtggcc caagacccac acactgtgga    3120
gcaatggagt gctggaaagc cagatgctca ttccaaaatc atatgcgggc cctttttcac    3180
agcacaatta ccgccaggc tatgccacgc aaaccgtggg cccatggcac ttaggcaaat    3240
tagagataga cttttggagaa tgccccggaa caacagtcac aattcaggag gattgtgacc    3300
atagaggccc atctttgagg accaccactg catctggaaa actagtcacg caatggtgct    3360
gccgctcctg cacgatgcct cccttaaggt tcttgggaga agatgggtgc tggtatggga    3420
tggagattag gcccttgagt gaaaaagaag agaaacatggt caaatcacag gtgacggccg    3480
gacagggcac atcagaaact ttttctatgg gtctgttgtg cctgaccttg tttgtggaag    3540
aatgcttgag gagaagagtc actaggaaac acatgatatt agttgtggtg atcactcttt    3600
gtgctatcat cctgggaggc ctcacatgga tggacttact acgagccctc atcatgttgg    3660
gggacactat gtctggtaga ataggaggac agatccacct agccatcatg gcagtgttca    3720
agatgtcacc aggatacgtg ctgggtgtgt ttttaaggaa actcacttca agagagacag    3780
cactaatggt aataggaatg gccatgacaa cggtgctttc aattccacat gaccttatgg    3840
aactcattga tggaatatca ctgggactaa ttttgctaaa aatagtaaca cagtttgaca    3900
acacccaagt gggaaccttta gctctttcct tgacttcat aagatcaaca atgccattgg    3960
```

```
tcatggcttg gaggaccatt atggctgtgt tgtttgtggt cacactcatt cctttgtgca    4020
ggacaagctg tcttcaaaaa cagtctcatt gggtagaaat aacagcactc atcctaggag    4080
cccaagctct gccagtgtac ctaatgactc ttatgaaagg agcctcaaga agatcttggc    4140
ctcttaacga gggcataatg gctgtgggtt tggttagtct cttaggaagc gctcttttaa    4200
agaatgatgt cccctttagct ggcccaatgg tggcaggagg cttacttctg gcggcttacg    4260
tgatgagtgt tagctcagca gatctgtcac tagagaaggc cgccaacgtg cagtgggatg    4320
aaatggcaga cataacaggc tcaagcccaa tcgtagaagt gaagcaggat gaagatggct    4380
ctttctccat acgggacgtc gaggaaacca atatgataac cctttggtg aaactggcac    4440
tgataacagt gtcaggtctc taccccttgg caattccagt cacaatgacc ttatggtaca    4500
tgtggcaagt gaaaacacaa agatcaggag ccctgtggga cgtcccctca cccgctgcca    4560
ctaaaaaagc cgcactgtct gaaggagtgt acaggatcat gcaaagaggg ttattcggga    4620
aaactcaggt tggagtaggg atacacatgg aaggtgtatt tcacacaatg tggcatgtaa    4680
caagaggatc agtgatctgc cacgagactg ggagattgga gccatcttgg gctgacgtca    4740
ggaatgacat gatatcatac ggtgggggat ggaggcttgg agacaaatgg acaaagaag    4800
aagacgttca ggtcctcgcc atagaaccag gaaaaaatcc taaacatgtc caaacgaaac    4860
ctggcctttt caagaccta actggagaaa ttggagcagt aacattagat ttcaaacccg    4920
gaacgtctgt ttctcccatc atcaacagga aggaaaagt catcggactc tatggaaatg    4980
gagtagttac caaatcaggt gattacgtca gtgccataac gcaagccgaa agaattggag    5040
agccagatta tgaagtggat gaggacattt ttcgaaagaa aagattaact ataatggact    5100
tacaccccgg agctggaaag acaaaaagaa ttcttccatc aatagtgaga gaagccttaa    5160
aaaggaggct acgaactttg attttagctc ccacgagagt ggtggcggcc gagatggaag    5220
aggccctacg tggactgcca atccgttatc agacccccagc tgtgaaatca gaacacacag    5280
gaagagagat tgtagacctc atgtgtcatg caaccttcac aacaagactt ttgtcatcaa    5340
ccagggttcc aaattacaac cttatagtga tggatgaagc acatttcacc gatccttcta    5400
gtgtcgcggc tagaggatac atctcgacca gggtggaaat gggagaggca gcagccatct    5460
tcatgaccgc aacccctccc ggagcgacag atccctttcc ccagagcaac agcccaatag    5520
aagacatcga gagggaaatt ccggaaaggt catggaacac agggttcgac tggataacag    5580
actaccaagg gaaaactgtg tggtttgttc ccagcataaa agctggaaat gacattgcaa    5640
attgtttgag aaagtcggga aagaaagtta tccagttgag taggaaaacc tttgatacag    5700
agtatccaaa aacgaaactc acggactggg actttgtggt cactacagac atatctgaaa    5760
tggggccaa ttttagagcc gggagagtga tagaccctag aagatgcctc aagccagtta    5820
tcctaccaga tggcccagag agagtcattt tagcaggtcc tattccagtg actccagcaa    5880
gcgctgctca gagaagaggg cgaataggaa ggaaccagc acaagaagac gaccaatacg    5940
ttttctccgg agacccacta aaaatgatg aagatcatgc ccactggaca gaagcaaaga    6000
tgctgcttga caatatctac accccagaag ggatcattcc aacattgttt ggtccggaaa    6060
gggaaaaaac ccaagccatt gatgagagt ttcgcctcag agggggaacaa aggaagactt    6120
ttgtggaatt aatgaggaga ggagaccttc cggtgtggct gagctataag gtagcttctg    6180
ctggcatttc ttacgaagat cgggaatggt gcttcacagg ggaaagaaat aaccaaattt    6240
tagaagaaaa catggaggtt gaaatttgga ctagagaggg agaaaagaaa agctaaggc    6300
caagatggtt agatgcacgt gtatacgctg accccatggc tttgaaggat ttcaaggagt    6360
```

```
ttgccagtgg aaggaagagt ataactctcg acatcctaac agagattgcc agtttgccaa   6420
cttacctttc ctctagggcc aagctcgccc ttgataacat agtcatgctc cacacaacag   6480
aaagaggagg gagggcctat caacacgccc tgaacgaact tccggagtca ctggaaacac   6540
tcatgcttgt agctttacta ggtgctatga cagcaggcat cttcctgttt ttcatgcaag   6600
ggaaaggaat agggaaattg tcaatggggtt tgataaccat tgcggtggct agtggcttgc   6660
tctgggtagc agaaattcaa ccccagtgga tagcggcctc aatcatacta gagttttttc   6720
tcatggtact gttgataccg gaaccagaaa acaaaggac cccacaagac aatcaattga   6780
tctacgtcat attgaccatt ctcaccatca ttggtctaat agcagccaac gagatggggc   6840
tgattgaaaa acaaaaacg gattttgggt tttaccaggt aaaaacagaa accaccatcc   6900
tcgatgtgga cttgagacca gcttcagcat ggacgctcta tgcagtagcc accacaattc   6960
tgactcccat gctgagacac accatagaaa acacgtcggc caacctatct ctagcagcca   7020
ttgccaacca ggcagccgtc ctaatggggc ttggaaaagg atggccgctc cacagaatgg   7080
acctcggtgt gccgctgtta gcaatgggat gctattctca agtgaaccca caaccttga   7140 cagcatcctt agtcatgctt ttagtccatt atgcaataat aggcccagga ttgcaggcaa   7200
aagccacaag agaggcccag aaaaggacag ctgctgggat catgaaaaat cccacagtgg   7260
acgggataac agtaatagat ctagaaccaa tatcctatga cccaaaattt gaaaagcaat   7320
tagggcaggt catgctacta gtcttgtgtg ctggacaact actcttgatg agaacaacat   7380
gggctttctg tgaagtcttg actttggcca caggaccaat cttgaccttg tgggagggca   7440
acccgggaag gttttggaac acgaccatag ccgtatccac cgccaacatt ttcagggaa   7500 gttacttggc gggagctgga ctggcttttt cactcataaa gaatgcacaa accccctagga   7560 ggggaactgg gaccacagga gagacactgg gagagaagtg gaagagacag ctaaactcat   7620
tagacagaaa agagtttgaa gagtataaaa aagtggaat actagaagtg gacaggactg   7680
aagccaagtc tgccctgaaa gatgggtcta aaatcaagca tgcagtatca agagggtcca   7740
gtaagatcag atggattgtt gagagaggga tggtaaagcc aaaagggaaa gttgtagatc   7800
ttggctgtgg gagaggagga tggtcttatt acatggcgac actcaagaac gtgactgaag   7860
tgaaagggta tacaaaagga ggtccaggac atgaagaacc gattcccatg gctacttatg   7920
gttggaattt ggtcaaactc cattcagggg ttgacgtgtt ctacaaaccc acagagcaag   7980
tggacaccct gctctgtgat attggggagt catcttctaa tccaacaata gaggaaggaa   8040
gaacattaag agttttgaag atggtggagc catggctctc ttcaaaacct gaattctgca   8100
tcaaagtcct taaccctac atgccaacag tcatagaaga gctggagaaa ctgcagagaa   8160 acatggtgg gaaccttgtc agatgccgc tgtccaggaa ctccaccat gagatgtatt   8220 gggtgtcagg agcgtcggga acattgtga gctctgtgaa cacaacatca agatgttgt   8280 tgaacaggtt cacaacaagg cataggaaac ccacttatga aaggacgta gatcttgggg   8340 caggaacgag aagtgtctcc actgaaacag aaaaaccaga catgacaatc attgggagaa   8400
ggcttcagcg attgcaagaa gagcacaaag aaacctggca ttatgatcag gaaaacccat   8460
acagaacctg ggcgtatcat ggaagctatg aagctccttc gacaggctct gcatcctcca   8520
tggtgaacgg ggtggtaaaa ctgctaacaa accctgggga tgtgattcca atggtgactc   8580
agttagccat gacagataca acccctttg gcaacaaaag agtgttcaaa gagaaggtgg   8640
ataccagaac accacaacca aaacccggta cacgaatggt tatgaccacg acagccaatt   8700
```

```
ggctgtgggc cctccttgga aagaagaaaa atcccagact gtgcacaagg gaagagttca    8760
tctcaaaagt tagatcaaac gcagccatag gcgcagtctt tcaggaagaa cagggatgga    8820
catcagccag tgaagctgtg aatgacagcc ggttttggga actggttgac aaagaaaggg    8880
ccctacacca ggaagggaaa tgtgaatcgt gtgtctataa catgatggga aaacgtgaga    8940
aaaagttagg agagtttggc agagccaagg gaagccgagc aatctggtac atgtggctgg    9000
gagcgcggtt tctggaattt gaagccctgg gttttttgaa tgaagatcac tggtttggca    9060
gagaaaattc atggagtgga gtggaagggg aaggtctgca cagattggga tatatcctgg    9120
aggagataga caagaaggat ggagacctaa tgtatgctga tgacacagca ggctgggaca    9180
caagaatcac tgaggatgac cttcaaaatg aggaactgat cacggaacag atggctcccc    9240
accacaagat cctagccaaa gccatttttca aactaaccta tcaaaacaaa gtggtgaaag    9300
tcctcagacc cacaccgcgg ggagcggtga tggatatcat atccaggaaa gaccaaagag    9360
gtagtggaca gttggaaca tatggtttga acacattcac caacatggaa gttcaactca    9420
tccgccaaat ggaagctgaa ggagtcatca cacaagatga catgcagaac ccaaaagggt    9480
tgaaagaaag agttgagaaa tggctgaaag agtgtggtgt cgacaggtta aagaggatgg    9540
caatcagtgg agacgattgc gtggtgaagc ccctagatga gaggtttggc acttccctcc    9600
tcttcttgaa cgacatggga aaggtgagga agacattcc gcagtgggaa ccatctaagg    9660
gatgaaaaa ctggcaagag gttccttttt gctcccacca ctttcacaag atctttatga    9720
aggatggccg ctcactagtt gttccatgta gaaaccagga tgaactgata gggagagcca    9780
gaatctcgca gggagctgga tggagcttaa gagaaacagc ctgcctgggc aaagcttacg    9840
cccagatgtg gtcgcttatg tacttccaca aagggatct gcgtttagcc tccatggcca    9900
tatgctcagc agttccaacg gaatggtttc caacaagcag aacaacatgg tcaatccacg    9960
ctcatcacca gtggatgacc actgaagata tgctcaaagt gtggaacaga gtgtggatag   10020
aagcaaccc taatatgact gacaagactc cagtccattc gtgggaagat ataccttacc   10080
tagggaaaag agaggatttg tggtgtggat ccctgattgg actttcttcc agagccacct   10140
gggcgaagaa cattcatacg gccataaccc aggtcaggaa cctgatcgga aaagaggaat   10200
acgtggatta catgccagta atgaaaagat acagtgctcc ttcagagagt gaaggagttc   10260
tgtaattacc aacaacaaac accaaaggct attgaagtca ggccacttgt gccacgtttt   10320
gagcaaaccg tgctgcctgt agctccgcca ataatgggag gcgtaataat ccccagggag   10380
gccatgcgcc acggaagctg tacgcgtggc atattggact agcggttaga ggagacccct   10440
cccatcactg ataaaacgca gcaaaagggg gcccgaagcc aggaggaagc tgtactcctg   10500
gtggaaggac tagaggttag aggagacccc cccaacacaa aaacagcata ttgacgctgg   10560
gaaagaccag agatcctgct gtctctgcaa catcaatcca ggcacagagc gccgcaagat   10620
ggattggtgt tgttgatcca acaggttct                                     10649
```

<210> SEQ ID NO 5
<211> LENGTH: 24
<212> TYPE: DNA
<213> ORGANISM: Artificial Sequence
<220> FEATURE:
<223> OTHER INFORMATION: Dengue 1-2-3 forward PCR primer

<400> SEQUENCE: 5

```
cagatctctg atgaacaacc aacg                                            24
```

```
<210> SEQ ID NO 6
<211> LENGTH: 24
<212> TYPE: DNA
<213> ORGANISM: Artificial Sequence
<220> FEATURE:
<223> OTHER INFORMATION: Dengue 2 forward (C to T) PCR primer

<400> SEQUENCE: 6
cagatctctg atgaataacc aacg                                              24

<210> SEQ ID NO 7
<211> LENGTH: 24
<212> TYPE: DNA
<213> ORGANISM: Artificial Sequence
<220> FEATURE:
<223> OTHER INFORMATION: Dengue 3 forward (C to T) PCR primer

<400> SEQUENCE: 7
cagatttctg atgaacaacc aacg                                              24

<210> SEQ ID NO 8
<211> LENGTH: 19
<212> TYPE: DNA
<213> ORGANISM: Artificial Sequence
<220> FEATURE:
<223> OTHER INFORMATION: Dengue 4 forward PCR primer

<400> SEQUENCE: 8
gatctctgga aaaatgaac                                                    19

<210> SEQ ID NO 9
<211> LENGTH: 21
<212> TYPE: DNA
<213> ORGANISM: Artificial Sequence
<220> FEATURE:
<223> OTHER INFORMATION: Dengue 1, 3 reverse PCR primer

<400> SEQUENCE: 9
tttgagaatc tcttcgccaa c                                                 21

<210> SEQ ID NO 10
<211> LENGTH: 20
<212> TYPE: DNA
<213> ORGANISM: Artificial Sequence
<220> FEATURE:
<223> OTHER INFORMATION: Dengue 2 reverse PCR primer

<400> SEQUENCE: 10
agttgacacg cggtttctct                                                   20

<210> SEQ ID NO 11
<211> LENGTH: 20
<212> TYPE: DNA
<213> ORGANISM: Artificial Sequence
<220> FEATURE:
<223> OTHER INFORMATION: Dengue 2 reverse (A to G) PCR primer

<400> SEQUENCE: 11
agtcgacacg cggtttctct                                                   20

<210> SEQ ID NO 12
<211> LENGTH: 18
<212> TYPE: DNA
<213> ORGANISM: Artificial Sequence
<220> FEATURE:
<223> OTHER INFORMATION: Dengue 4 reverse PCR primer
```

-continued

```
<400> SEQUENCE: 12
agaatctctt caccaacc                                                       18

<210> SEQ ID NO 13
<211> LENGTH: 37
<212> TYPE: DNA
<213> ORGANISM: Artificial Sequence
<220> FEATURE:
<223> OTHER INFORMATION: Dengue probe

<400> SEQUENCE: 13
cgcgatcgcg tttcagcata ttgaaagacg gatcgcg                                  37

<210> SEQ ID NO 14
<211> LENGTH: 37
<212> TYPE: DNA
<213> ORGANISM: Artificial Sequence
<220> FEATURE:
<223> OTHER INFORMATION: Dengue probe

<400> SEQUENCE: 14
cgcgatcgcg tttcagcata ttgaaaggcg gatcgcg                                  37

<210> SEQ ID NO 15
<211> LENGTH: 37
<212> TYPE: DNA
<213> ORGANISM: Artificial Sequence
<220> FEATURE:
<223> OTHER INFORMATION: Dengue probe

<400> SEQUENCE: 15
cgcgatccac gcgtttcagc atattgatag gatcgcg                                  37

<210> SEQ ID NO 16
<211> LENGTH: 37
<212> TYPE: DNA
<213> ORGANISM: Artificial Sequence
<220> FEATURE:
<223> OTHER INFORMATION: Dengue probe

<400> SEQUENCE: 16
cgcgatcttt cagcatattg aaaggtggtc gatcgcg                                  37

<210> SEQ ID NO 17
<211> LENGTH: 37
<212> TYPE: DNA
<213> ORGANISM: Artificial Sequence
<220> FEATURE:
<223> OTHER INFORMATION: Dengue probe

<400> SEQUENCE: 17
cgcgatcttc agcatattga aagacggtcg gatcgcg                                  37

<210> SEQ ID NO 18
<211> LENGTH: 19
<212> TYPE: DNA
<213> ORGANISM: Artificial Sequence
<220> FEATURE:
<223> OTHER INFORMATION: Dengue probe

<400> SEQUENCE: 18
ctcgcgcgtt tcagcatat                                                      19

<210> SEQ ID NO 19
<211> LENGTH: 19
```

```
<212> TYPE: DNA
<213> ORGANISM: Artificial Sequence
<220> FEATURE:
<223> OTHER INFORMATION: Dengue probe

<400> SEQUENCE: 19
ctctcgcgtt tcagcatat                                                19

<210> SEQ ID NO 20
<211> LENGTH: 21
<212> TYPE: DNA
<213> ORGANISM: Artificial Sequence
<220> FEATURE:
<223> OTHER INFORMATION: Dengue probe

<400> SEQUENCE: 20
ctctcacgtt tcagcatatt g                                             21

<210> SEQ ID NO 21
<211> LENGTH: 19
<212> TYPE: DNA
<213> ORGANISM: Artificial Sequence
<220> FEATURE:
<223> OTHER INFORMATION: Dengue probe

<400> SEQUENCE: 21
ctcacgcgtt tcagcatat                                                19
```

METHODS AND REAGENTS FOR DETECTION, QUANTITATION, AND SEROTYPING OF DENGUE VIRUSES

CROSS REFERENCE TO RELATED APPLICATION

This application is a divisional of U.S. patent application Ser. No. 14/430,715, filed Mar. 24, 2015, which is a 371 National Phase of PCT/US2013/063238, filed Oct. 3, 2013, which claims priority benefit of U.S. Provisional Patent Application Ser. No. 61/709,687, filed on Oct. 4, 2012, all of which are incorporated by reference in their entirety.

TECHNICAL FIELD

The present invention pertains generally to dengue virus and viral diagnostics. In particular, the invention relates to nucleic acids for use in the detection of dengue viruses, including any of the serotypes 1-4.

BACKGROUND

Dengue fever, dengue hemorrhagic fever, and dengue shock syndrome result from infection with one of four closely related serotypes of dengue virus, the most common vector-borne pathogen worldwide. These serotypes are designated dengue virus 1-4 (DEN 1-4), and they are transmitted by the mosquitoes *Aedes aegypti* and *Aedes albopictus*, which reside in tropical and sub-tropical areas of the world (Special Programme for Research and Training in Tropical Diseases, World Health Organization, (2009) Dengue: guidelines for diagnosis, treatment, prevention, and control. Geneva: TDR: World Health Organization). Infection with one serotype (primary infection) results in immunity to that serotype, but infection can occur with any of the remaining serotypes (secondary infection). Secondary infection has been shown to be a significant risk factor for the development of severe dengue, including dengue hemorrhagic fever (DHF) and dengue shock syndrome (DSS) (Halstead et al. (1970) Yale J. Biol. Med. 42: 311-328). Recent reports estimate that 230 million infections occur annually, including 2 million cases of severe disease and 21,000 deaths. Over 3.6 billion people live in endemic regions and are at risk for infection (Gubler (2012) Am. J. Trop. Med. Hyg. 86: 743-744).

Despite the widespread nature of this disease, available diagnostic tests remain suboptimal (Special Programme for Research and Training in Tropical Diseases, World Health Organization, (2009) Dengue: guidelines for diagnosis, treatment, prevention, and control. Geneva: TDR: World Health Organization). The gold standard for diagnosis remains seroconversion, requiring collection of both acute and convalescent sera, and the gold standard for molecular diagnosis is a hemi-nested reverse transcription polymerase chain reaction (RT-PCR) assay originally developed in 1992 (Lanciotti et al. (1992) J. Clin. Microbiol. 30: 545-551). This assay requires two rounds of PCR followed by gel electrophoresis for amplicon detection. Not only do these numerous steps result in an increased risk of contamination, they also significantly limit the clinical utility of this assay, as the turnaround time is one day or longer. A number of other nucleic acid amplification tests have been developed for the detection and serotyping of dengue, including RT-PCR, real-time RT-PCR (rRT-PCR), and isothermal amplification techniques (Johnson et al. (2005) J. Clin. Microbiol. 43: 4977-4983; Kong (2006) J. Virol. Methods 138: 123-130; Hue et al. (2011) J. Virol. Methods 177: 168-173; and Munoz-Jordan et al. (2009) J. Clin. Microbiol. 47: 927-931). Many designs rely on two duplex reactions (two reactions per sample) or even four separate reactions for serotyping, and single-reaction, multiplex assays for detection and serotyping of dengue viruses lack the analytical sensitivity of the original hemi-nested RT-PCR (Johnson et al., supra; Hue et al., supra). Although these PCR assays are used around the world, an international external quality control assessment, published in 2010 involving 37 laboratories performing 46 tests, showed that 80% of these tests lacked sensitivity, specificity, or both (Domingo et al. (2010) PLoS Negl. Trop. Dis. 4(10) pii: e833).

Rapid and point-of-care assays based on the detection of IgM, IgG, and the non-structural 1 (NS1) protein have also been developed, but these all have significant limitations. IgM does not become detectable until at least the third day of clinical illness, but is not reliably positive until day five and beyond (Blacksell et al. (2006) Clin. Infect. Dis. 42: 1127-1134). These tests can be non-specific as IgM may persist two to three months following infection, and IgM against other flaviviruses cross-reacts with some tests (Blacksell et al. (2008) Diagn. Microbiol. Infect. Dis. 60: 43-49; Blacksell et al. (2011) Clin. Vaccine Immunol. 18: 2095-2101). IgG cannot distinguish current from past infection, an important issue in endemic areas where secondary infection is common. Assays based on detection of NS1 tend to be specific for dengue infection, but the sensitivity of these assays ranges widely in published reports from 24-93% (Guzman et al. (2010) PLoS Negl. Trop. Dis. 4; Tricou et al. (2010) BMC Infect. Dis. 10: 142). The sensitivity varies based on the specific assay used and the infecting serotype (Guzman et al., supra). All of the assays also show a roughly 20% decrease in sensitivity in the setting of secondary infection compared to primary infection (Tricou et al., supra; Chaterji et al. (2011) Am. J. Trop. Med. Hyg. 84: 224-228).

Thus, there remains a need for the development of effective strategies for the diagnosis, treatment, and prevention of dengue viral infection. The availability of nucleic acid diagnostic tests capable of efficiently detecting dengue virus in human specimens such as plasma, serum and respiratory secretions will assist the medical community in better diagnosing and treating dengue viral infections.

SUMMARY

The present invention is based on the development of sensitive, reliable nucleic acid-based diagnostic assays for the detection of dengue viruses in biological samples from potentially infected subjects. The methods allow the rapid detection in a single assay of dengue virus infection caused by one or several dengue viruses, such as caused by one or more dengue virus serotypes 1-4. The methods can also be used to quantitate the amount of virus that is present and to determine which dengue virus serotypes are present in the biological sample. If infection is detected, the individual can be given appropriate therapy, and steps can be taken to prevent or reduce further transmission and spread of dengue virus. If infection is ruled-out, other potential causes of undifferentiated febrile illness can be further investigated.

The methods utilize primers and probes for amplifying and/or detecting target sequences of one or more dengue virus serotypes, to allow detection of a single serotype or multiple serotypes simultaneously in a single assay. In certain embodiments, the dengue virus sequences are detected using reverse transcriptase-polymerase chain reaction (RT-PCR), for example, using real-time RT-PCR and/or multiplex RT-PCR. Other nucleic-acid based detection techniques such as, but not limited to, nucleic acid sequence based amplification (NASBA), a 5' nuclease assay (e.g., TaqMan™), or transcription-mediated amplification (TMA), can also be used.

Exemplary primers (SEQ ID NOS:5-12) and probes (SEQ ID NOS:13-21) are shown in Example 1 (see Tables 1 and 2). Changes to the nucleotide sequences of these primers and probes may be introduced corresponding to genetic variations in particular Dengue strains. For example up to three nucleotide changes, including 1 nucleotide change, 2 nucleotide changes, or three nucleotide changes, may be made in a sequence selected from the group consisting of SEQ ID NOS:5-21, wherein the oligonucleotide primer or probe is capable of hybridizing to and amplifying or detecting a particular dengue virus target nucleic acid.

In one aspect, the invention includes a composition for detecting dengue virus in a biological sample using a nucleic acid amplification assay, wherein the composition comprises at least one set of oligonucleotide primers comprising a forward primer and a reverse primer capable of amplifying at least a portion of a dengue virus genome, the portion comprising a 5' UTR sequence or a dengue virus capsid coding sequence, wherein the primers are not more than 40 nucleotides in length, wherein said set of primers is selected from the group consisting of:

a) a forward primer comprising the sequence of SEQ ID NO:5 and a reverse primer comprising the sequence of SEQ ID NO:9;
b) a forward primer comprising the sequence of SEQ ID NO:5 and a reverse primer comprising the sequence of SEQ ID NO:10;
c) a forward primer comprising the sequence of SEQ ID NO:5 and a reverse primer comprising the sequence of SEQ ID NO:11;
d) a forward primer comprising the sequence of SEQ ID NO:6 and a reverse primer comprising the sequence of SEQ ID NO:10;
e) a forward primer comprising the sequence of SEQ ID NO:6 and a reverse primer comprising the sequence of SEQ ID NO:11;
f) a forward primer comprising the sequence of SEQ ID NO:7 and a reverse primer comprising the sequence of SEQ ID NO:9;
g) a forward primer comprising the sequence of SEQ ID NO:8 and a reverse primer comprising the sequence of SEQ ID NO:12;
h) a forward primer and a reverse primer each comprising at least 10 contiguous nucleotides from the corresponding nucleotide sequences of the forward primer and reverse primer of a primer set selected from the group consisting of (a)-(g);
i) a forward primer and a reverse primer comprising at least one nucleotide sequence that differs from the corresponding nucleotide sequence of the forward primer or reverse primer of a primer set selected from the group consisting of (a)-(g) in that the primer has up to three nucleotide changes compared to the corresponding sequence, wherein the primer is capable of hybridizing to and amplifying dengue virus nucleic acids in the nucleic acid amplification assay; and
j) a forward primer and a reverse primer comprising nucleotide sequences that are complements of the corresponding nucleotide sequences of the forward primer and reverse primer of a primer set selected from the group consisting of (a)-(i).

In certain embodiments, the composition may further comprise at least one detectably labeled oligonucleotide probe sufficiently complementary to and capable of hybridizing with dengue virus RNA or an amplicon thereof. Exemplary probes include a probe comprising the sequence of SEQ ID NO:13, a probe comprising the sequence of SEQ ID NO:14, a probe comprising the sequence of SEQ ID NO:15, a probe comprising the sequence of SEQ ID NO:16, a probe comprising the sequence of SEQ ID NO:17, a probe comprising the sequence of SEQ ID NO:18, a probe comprising the sequence of SEQ ID NO:19, a probe comprising the sequence of SEQ ID NO:20, and a probe comprising the sequence of SEQ ID NO:21. The composition may include a set of probes capable of detecting multiple serotypes of dengue virus, including two or more, three or more, or all four serotypes of dengue virus. In one embodiment, the set of probes comprises a probe comprising the sequence of SEQ ID NO:13, a probe comprising the sequence of SEQ ID NO:14, a probe comprising the sequence of SEQ ID NO:15, and a probe comprising the sequence of SEQ ID NO:16.

The probe may be detectably labeled with a fluorophore such as, but not limited to carboxyfluorescein (FAM), CAL Fluor Orange 560, CAL Fluor Red 610, Quasar Blue 670, 6-carboxyfluorescein (6-FAM), tetramethyl rhodamine (TAMRA), and 2',4',5',7'-tetrachloro-4-7-dichlorofluorescein (TET). In one embodiment, the probe comprises a 5'-fluorophore and a 3'-quencher. For example, the probe may comprises a 5'-fluorophore selected from the group consisting of carboxyfluorescein (FAM), CAL Fluor Orange 560, CAL Fluor Red 610, Quasar Blue 670, and 2',4',5',7'-tetrachloro-4-7-dichlorofluorescein (TET) and a 3'-quencher selected from the group consisting of a black hole quencher (BHQ), tetramethyl rhodamine (TAMRA), dabcyl, and dihydrocyclopyrroloindole tripeptide minor groove binder (MGB). In one embodiment, the probe is a molecular beacon.

In one embodiment, the composition comprises a primer comprising the sequence of SEQ ID NO:5, a primer comprising the sequence of SEQ ID NO:6, a primer comprising the sequence of SEQ ID NO:7, a primer comprising the sequence of SEQ ID NO:8, a primer comprising the sequence of SEQ ID NO:9, a primer comprising the sequence of SEQ ID NO:10, a primer comprising the sequence of SEQ ID NO:11, a primer comprising the sequence of SEQ ID NO:12, a probe comprising the sequence of SEQ ID NO:13, a probe comprising the sequence of SEQ ID NO:14, a probe comprising the sequence of SEQ ID NO:15, and a probe comprising the sequence of SEQ ID NO:16.

In one embodiment, the probe comprising the sequence of SEQ ID NO:13 further comprises a 5' FAM fluorophore and a 3' BHQ-1 quencher, the probe comprising the sequence of SEQ ID NO:14 further comprises a 5' CAL Fluor Orange 560 fluorophore and a 3' BHQ-1 quencher, the probe comprising the sequence of SEQ ID NO:15 further comprises a 5' CAL Fluor Red 610 fluorophore and a 3' BHQ-2 quencher, and the probe comprising the sequence of SEQ ID NO:16 further comprises a 5' Quasar Blue 670 fluorophore and a 3' BHQ-2 quencher.

In another aspect, the invention includes a method for detecting dengue virus in a biological sample, the method comprising:

a) contacting a biological sample suspected of containing dengue virus with a composition, as described herein, for detecting dengue virus by nucleic acid amplification of viral RNA, b) amplifying dengue virus nucleic acids if present, wherein the nucleic acids comprise at least one target sequence selected from the group consisting of a dengue-1 target sequence, a dengue-2 target sequence, a dengue-3 target sequence, and a dengue-4 target sequence; and c) detecting the presence of the amplified nucleic acids using at least one detectably labeled oligonucleotide probe sufficiently complementary to and capable of hybridizing with the dengue virus RNA or amplicon thereof, if present, as an indication of the presence or absence of dengue virus in the sample.

In one embodiment, at least one probe is selected from the group consisting of a probe comprising the sequence of SEQ ID NO:13, a probe comprising the sequence of SEQ ID NO:14, a probe comprising the sequence of SEQ ID NO:15, a probe comprising the sequence of SEQ ID NO:16, a probe comprising the sequence of SEQ ID NO:17, a probe comprising the sequence of SEQ ID NO:18, a probe comprising the sequence of SEQ ID NO:19, a probe comprising the sequence of SEQ ID NO:20, and a probe comprising the sequence of SEQ ID NO:21.

In another embodiment, a set of probes is used for detecting dengue virus in a biological sample, wherein the set of probes comprises a probe comprising the sequence of SEQ ID NO:13, a probe comprising the sequence of SEQ ID NO:14, a probe comprising the sequence of SEQ ID NO:15, and a probe comprising the sequence of SEQ ID NO:16.

In certain embodiments, the probe used in the method of detecting dengue virus comprises a fluorophore, such as, but not limited to carboxyfluorescein (FAM), CAL Fluor Orange 560, CAL Fluor Red 610, Quasar Blue 670, 6-carboxyfluorescein (6-FAM), tetramethyl rhodamine (TAMRA), and 2',4',5',7'-tetrachloro-4-7-dichlorofluorescein (TET). The detectably labeled probe may comprise a 5'-fluorophore and a 3'-quencher. For example, the probe may comprises a 5'-fluorophore selected from the group consisting of carboxyfluorescein (FAM), CAL Fluor Orange 560, CAL Fluor Red 610, Quasar Blue 670, and 2',4',5',7'-tetrachloro-4-7-dichlorofluorescein (TET) and a 3'-quencher selected from the group consisting of a black hole quencher (BHQ), tetramethyl rhodamine (TAMRA), dabcyl, and dihydrocyclopyrroloindole tripeptide minor groove binder (MGB). In one embodiment, the probe used for detection of dengue virus is a molecular beacon.

In one embodiment, the primers used for detecting dengue virus in the biological sample comprise a primer comprising the sequence of SEQ ID NO:5, a primer comprising the sequence of SEQ ID NO:6, a primer comprising the sequence of SEQ ID NO:7, a primer comprising the sequence of SEQ ID NO:8, a primer comprising the sequence of SEQ ID NO:9, a primer comprising the sequence of SEQ ID NO:10, a primer comprising the sequence of SEQ ID NO:11, and a primer comprising the sequence of SEQ ID NO:12.

In another embodiment, the primers used for detecting dengue virus in the biological sample comprise a primer comprising the sequence of SEQ ID NO:5, a primer comprising the sequence of SEQ ID NO:8, a primer comprising the sequence of SEQ ID NO:9, a primer comprising the sequence of SEQ ID NO:10, and a primer comprising the sequence of SEQ ID NO:12.

In another embodiment, the primers used for detecting dengue virus in the biological sample comprise a primer comprising the sequence of SEQ ID NO:5, a primer comprising the sequence of SEQ ID NO:8, a primer comprising the sequence of SEQ ID NO:9, a primer comprising the sequence of SEQ ID NO:11, and a primer comprising the sequence of SEQ ID NO:12.

In another embodiment, the primers used for detecting dengue virus in the biological sample comprise a primer comprising the sequence of SEQ ID NO:5, a primer comprising the sequence of SEQ ID NO:8, a primer comprising the sequence of SEQ ID NO:9, a primer comprising the sequence of SEQ ID NO:10, a primer comprising the sequence of SEQ ID NO:11, and a primer comprising the sequence of SEQ ID NO:12.

In another embodiment, the primers used for detecting dengue virus in the biological sample comprise a primer comprising the sequence of SEQ ID NO:5, a primer comprising the sequence of SEQ ID NO:6, a primer comprising the sequence of SEQ ID NO:8, a primer comprising the sequence of SEQ ID NO:9, a primer comprising the sequence of SEQ ID NO:10, and a primer comprising the sequence of SEQ ID NO:12.

In another embodiment, the primers used for detecting dengue virus in the biological sample comprise a primer comprising the sequence of SEQ ID NO:5, a primer comprising the sequence of SEQ ID NO:6, a primer comprising the sequence of SEQ ID NO:8, a primer comprising the sequence of SEQ ID NO:9, a primer comprising the sequence of SEQ ID NO:11, and a primer comprising the sequence of SEQ ID NO:12.

In another embodiment, the primers used for detecting dengue virus in the biological sample comprise a primer comprising the sequence of SEQ ID NO:5, primer comprising the sequence of SEQ ID NO:7, a primer comprising the sequence of SEQ ID NO:8, a primer comprising the sequence of SEQ ID NO:9, a primer comprising the sequence of SEQ ID NO:10, and a primer comprising the sequence of SEQ ID NO:12.

In another embodiment, the primers used for detecting dengue virus in the biological sample comprise a primer comprising the sequence of SEQ ID NO:5, primer comprising the sequence of SEQ ID NO:7, a primer comprising the sequence of SEQ ID NO:8, a primer comprising the sequence of SEQ ID NO:9, a primer comprising the sequence of SEQ ID NO:11, and a primer comprising the sequence of SEQ ID NO:12.

In another embodiment, the primers and probes that are used for detecting dengue virus in a biological sample comprise a primer comprising the sequence of SEQ ID NO:5, a primer comprising the sequence of SEQ ID NO:6, a primer comprising the sequence of SEQ ID NO:7, a primer comprising the sequence of SEQ ID NO:8, a primer comprising the sequence of SEQ ID NO:9, a primer comprising the sequence of SEQ ID NO:10, a primer comprising the sequence of SEQ ID NO:11, a primer comprising the sequence of SEQ ID NO:12, a probe comprising the sequence of SEQ ID NO:13, a probe comprising the sequence of SEQ ID NO:14, a probe comprising the sequence of SEQ ID NO:15, and a probe comprising the sequence of SEQ ID NO:16. In one embodiment, the probe comprising the sequence of SEQ ID NO:13 further comprises a 5' FAM fluorophore and a 3' BHQ-1 quencher, the probe comprising the sequence of SEQ ID NO:14 further comprises a 5' CAL Fluor Orange 560 fluorophore and a 3' BHQ-1 quencher, the probe comprising the sequence of SEQ ID NO:15 further comprises a 5' CAL Fluor Red 610 fluorophore and a 3' BHQ-2 quencher, and the probe comprising the sequence of SEQ ID NO:16 further comprises a 5' Quasar Blue 670 fluorophore and a 3' BHQ-2 quencher.

In another aspect, the invention includes an isolated oligonucleotide not more than 40 nucleotides in length comprising a nucleotide sequence comprising at least 10 contiguous nucleotides from a nucleotide sequence selected from the group consisting of SEQ ID NOS:5-21; or variants thereof comprising a nucleotide sequence that differs from a nucleotide sequence selected from the group consisting of SEQ ID NOS:5-21 by up to three nucleotide changes, wherein the oligonucleotide is capable of hybridizing to and amplifying and/or detecting dengue virus nucleic acids; or complements thereof. Oligonucleotides may further comprise a detectable label. For example, the detectable label may be a fluorophore such as, but not limited to carboxyfluorescein (FAM), CAL Fluor Orange 560, CAL Fluor Red 610, Quasar Blue 670, 6-carboxyfluorescein (6-FAM), tetramethyl rhodamine (TAMRA), and 2',4',5',7'-tetrachloro-4-7-dichlorofluorescein (TET). The oligonucleotide may further comprise a quencher such as, but not limited to a black hole quencher (BHQ), tetramethyl rhodamine (TAMRA), dabcyl, and a minor groove binder (MGB). In certain embodiments, the oligonucleotide is selected from the group consisting of: an oligonucleotide consisting of a nucleotide sequence selected from the group consisting of SEQ ID NOS:5-21 or a complement thereof.

In another aspect, the invention includes a kit for detecting dengue virus in a biological sample by nucleic acid amplification of viral RNA. The kit may comprise a composition, as described herein, comprising at least one set of primers including a forward primer and a reverse primer capable of amplifying at least a portion of a dengue virus genome, including a 5' UTR sequence or a dengue capsid coding sequence. The kit may further comprise written instructions for identifying the presence of the dengue virus, quantitating the virus, and/or serotyping dengue virus. The kit may also comprise reagents for performing reverse transcriptase polymerase chain reaction (RT-PCR), nucleic acid sequence based amplification (NASBA), transcription-mediated amplification (TMA), or a fluorogenic 5' nuclease assay.

The methods of the invention can be used to detect dengue virus in biological samples such as, but not limited to, blood, plasma, serum, peripheral blood mononuclear cells, liver, lung, spleen, thymus, kidneys, lymph nodes, and bone marrow. Using the methods of the invention, individuals infected with dengue virus can be identified. The, dengue virus can be specifically detected even in samples containing other viruses, such as West Nile virus, Japanese encephalitis virus, tick-born encephalitis virus, HIV and/or HCV. Moreover, the assays can be used to screen mosquitoes, primates, and other hosts for dengue virus in order to determine if a particular insect or animal population is infected with the virus, thereby preventing further transmission and spread of dengue virus infection. Additionally, infected blood samples can be detected and excluded from transfusion, as well as from the preparation of blood derivatives.

These and other embodiments of the subject invention will readily occur to those of skill in the art in view of the disclosure herein.

DETAILED DESCRIPTION OF THE INVENTION

Figure 1A:
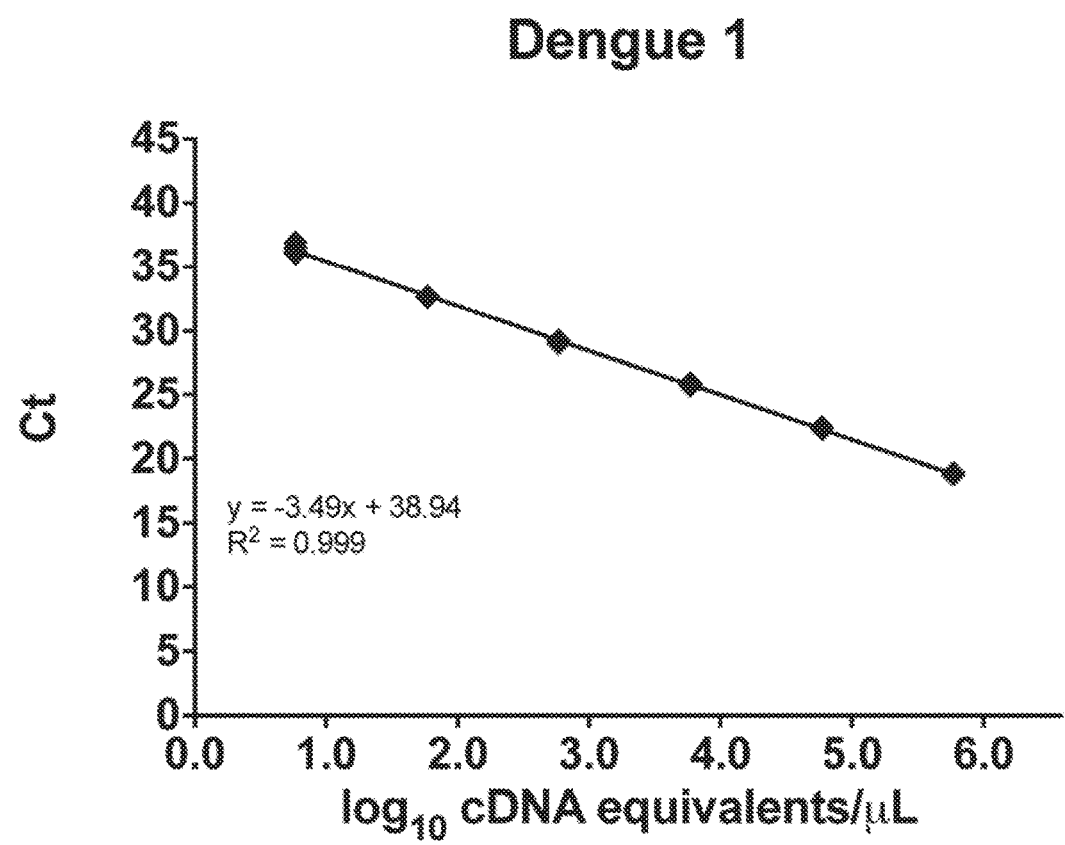
FIGS. 1A-1D show the linear ranges for multiplex rRT-PCR assays for the four dengue serotypes: dengue 1 (FIG. 1A), dengue 2 (FIG. 1B), dengue 3 (FIG. 1C), and dengue 4 (FIG. 1D).

The practice of the present invention will employ, unless otherwise indicated, conventional methods of virology, chemistry, biochemistry, recombinant DNA techniques and immunology, within the skill of the art. Such techniques are explained fully in the literature. See, e.g., *Fundamental Virology* (D. M. Knipe, P. M. Howley, D. E. Griffin, R. A. Lamb, M. A. Martin, B. Roizman, S. E. Straus, eds.), Lippincott Williams & Wilkins; Fourth edition, 2001; *Dengue Virus* (Current Topics in Microbiology and Immunology, A. L. Rothman, ed.), Springer; $1^{st}$ edition, 2009; *Frontiers in Dengue Virus Research* (K. A. Hanley and S. C. Weaver eds.), Caister Academic Press, $1^{st}$ edition, 2010; *Handbook of Experimental Immunology*, Vols. I-IV (D. M. Weir and C. C. Blackwell eds., Blackwell Scientific Publications); T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* ($3^{rd}$ Edition, 2001); *Methods In Enzymology* (S. Colowick and N. Kaplan eds., Academic Press, Inc.).

All publications, patents and patent applications cited herein, whether supra or infra, are hereby incorporated by reference in their entireties.

1. Definitions

In describing the present invention, the following terms will be employed, and are intended to be defined as indicated below.

It must be noted that, as used in this specification and the appended claims, the singular forms "a", "an" and "the" include plural referents unless the content clearly dictates otherwise. Thus, for example, reference to "a Dengue virus oligonucleotide" includes a mixture of two or more such oligonucleotides, and the like.

As used herein, the term "dengue virus" refers to members of the Flaviviridae family of enveloped viruses with a single-stranded positive-sense RNA genome (see, e.g., *Frontiers in Dengue Virus Research*, Hanley and Weaver (editors), Caister Academic Press, 2010). The term dengue virus may include any serotype of dengue virus, such as serotypes 1-4, which is capable of causing disease in an animal or human subject. In particular, the term encompasses any subtype of dengue virus that causes disease in humans, including strains DEN 1 Hawaii 1944, Den 2 New Guinea C strain, DEN 3 strain H87, and DEN 4 strain H241. A large number of dengue isolates have been partially or completely sequenced. See, e.g., the Broad Institute Dengue Virus Portal (website at broadinstitute.org/annotation/viral/Dengue/); the Dengue Virus Database (website at denguedb.org); the Virus Pathogen Resource (website at viprbrc.org/brc/home.do?decorator=flavi_dengue) and the GenBank database, which contain complete sequences for dengue viruses, including serotypes 1-4.

"Substantially purified" generally refers to isolation of a substance (compound, polynucleotide, oligonucleotide, protein, or polypeptide) such that the substance comprises the majority percent of the sample in which it resides. Typically in a sample, a substantially purified component comprises 50%, preferably 80%-85%, more preferably 90-95% of the sample. Techniques for purifying polynucleotides oligonucleotides and polypeptides of interest are well-known in the art and include, for example, ion-exchange chromatography, affinity chromatography and sedimentation according to density.

By "isolated" is meant, when referring to a polypeptide, that the indicated molecule is separate and discrete from the whole organism with which the molecule is found in nature or is present in the substantial absence of other biological macro-molecules of the same type. The term "isolated" with respect to a polynucleotide or oligonucleotide is a nucleic acid molecule devoid, in whole or part, of sequences normally associated with it in nature; or a sequence, as it exists in nature, but having heterologous sequences in association therewith; or a molecule disassociated from the chromosome.

"Homology" refers to the percent identity between two polynucleotide or two polypeptide moieties. Two nucleic acid, or two polypeptide sequences are "substantially homologous" to each other when the sequences exhibit at least about 50% sequence identity, preferably at least about 75% sequence identity, more preferably at least about 80%-85% sequence identity, more preferably at least about 90% sequence identity, and most preferably at least about 95%-98% sequence identity over a defined length of the molecules. As used herein, substantially homologous also refers to sequences showing complete identity to the specified sequence.

In general, "identity" refers to an exact nucleotide-to-nucleotide or amino acid-to-amino acid correspondence of two polynucleotides or polypeptide sequences, respectively. Percent identity can be determined by a direct comparison of the sequence information between two molecules by aligning the sequences, counting the exact number of matches between the two aligned sequences, dividing by the length of the shorter sequence, and multiplying the result by 100. Readily available computer programs can be used to aid in the analysis, such as ALIGN, Dayhoff, M. O. in *Atlas of Protein Sequence and Structure* M. O. Dayhoff ed., 5 Suppl. 3:353-358, National biomedical Research Foundation, Washington, D.C., which adapts the local homology algorithm of Smith and Waterman *Advances in Appl. Math.* 2:482-489, 1981 for peptide analysis. Programs for determining nucleotide sequence identity are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent identity of a particular nucleotide sequence to a reference sequence can be determined using the homology algorithm of Smith and Waterman with a default scoring table and a gap penalty of six nucleotide positions.

Another method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs are readily available.

Alternatively, homology can be determined by hybridization of polynucleotides under conditions which form stable duplexes between homologous regions, followed by digestion with single-stranded-specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *DNA Cloning,* supra; *Nucleic Acid Hybridization,* supra.

The terms "polynucleotide," "oligonucleotide," "nucleic acid" and "nucleic acid molecule" are used herein to include a polymeric form of nucleotides of any length, either ribonucleotides or deoxyribonucleotides. This term refers only to the primary structure of the molecule. Thus, the term includes triple-, double- and single-stranded DNA, as well as triple-, double- and single-stranded RNA. It also includes modifications, such as by methylation and/or by capping, and unmodified forms of the polynucleotide. More particularly, the terms "polynucleotide," "oligonucleotide," "nucleic acid" and "nucleic acid molecule" include polydeoxyribonucleotides (containing 2-deoxy-D-ribose), polyribonucleotides (containing D-ribose), any other type of polynucleotide which is an N- or C-glycoside of a purine or pyrimidine base, and other polymers containing nonnucleotidic backbones, for example, polyamide (e.g., peptide nucleic acids (PNAs)) and polymorpholino (commercially available from the Anti-Virals, Inc., Corvallis, Oreg., as Neugene) polymers, and other synthetic sequence-specific nucleic acid polymers providing that the polymers contain nucleobases in a configuration which allows for base pairing and base stacking, such as is found in DNA and RNA. There is no intended distinction in length between the terms "polynucleotide," "oligonucleotide," "nucleic acid" and "nucleic acid molecule," and these terms will be used interchangeably. Thus, these terms include, for example, 3'-deoxy-2',5'-DNA, oligodeoxyribonucleotide N3' P5' phosphoramidates, 2'-O-alkyl-substituted RNA, double- and single-stranded DNA, as well as double- and single-stranded RNA, DNA:RNA hybrids, and hybrids between PNAs and DNA or RNA, and also include known types of modifications, for example, labels which are known in the art, methylation, "caps," substitution of one or more of the naturally occurring nucleotides with an analog, internucleotide modifications such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalklyphosphoramidates, aminoalkylphosphotriesters), those containing pendant moieties, such as, for example, proteins (including nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide.

A dengue virus polynucleotide, oligonucleotide, nucleic acid and nucleic acid molecule, as defined above, is a nucleic acid molecule derived from a dengue virus, including, without limitation, any of the various dengue virus serotypes 1-4. The molecule need not be physically derived from the particular isolate in question, but may be synthetically or recombinantly produced.

Nucleic acid sequences for a number of dengue virus isolates are known. Representative dengue virus sequences are presented in SEQ ID NOS:1-4 of the Sequence Listing. Additional representative sequences, including sequences of the 5'-untranslated region (UTR) and coding region for the capsid protein C from dengue virus isolates are listed in the National Center for Biotechnology Information (NCBI) database. See, for example, NCBI entries: Accession No. NC_001477, Accession No. NC_001474, Accession No. NC_001475, Accession No. NC_002640, Accession No. AB609588, Accession No. EU848545, Accession No. AB609589, Accession No. AF038403, Accession No. AF038402, Accession No. M29095, Accession No. M93130, Accession No. AB609590, Accession No. AB609591, Accession No. S66064, Accession No. AY947539, Accession No. JN559741, Accession No. JN559740, Accession No. JF357906, Accession No. HQ634199, Accession No. HQ541794, Accession No. EU076567, Accession No. EU076565, Accession No. EU076563, Accession No. EU076561, Accession No. JQ950328, Accession No. JN796245, Accession No. JN819424, Accession No. JN819422, Accession No. JN819414, Accession No. JN819412, Accession No. JN819406, Accession No. JN819417, Accession No. JN819415, Accession No. JN819409, Accession No. JN093514, Accession No. JF730055, Accession No. JN000937, Accession No. JF937647, Accession No. JN819406, Accession No. GQ868543; all of which sequences (as entered by the date of filing of this application) are herein incorporated by reference. See also Weaver et al. (2009) Infect. Genet. Evol. 9(4):523-540 and Rico-Hesse (2003) Adv. Virus Res. 59:315-341 for sequence comparisons and a discussion of genetic diversity and phylogenetic analysis of dengue viruses.

A polynucleotide "derived from" a designated sequence refers to a polynucleotide sequence which comprises a contiguous sequence of approximately at least about 6 nucleotides, preferably at least about 8 nucleotides, more preferably at least about 10-12 nucleotides, and even more preferably at least about 15-20 nucleotides corresponding, i.e., identical or complementary to, a region of the designated nucleotide sequence. The derived polynucleotide will not necessarily be derived physically from the nucleotide sequence of interest, but may be generated in any manner, including, but not limited to, chemical synthesis, replication, reverse transcription or transcription, which is based on the information provided by the sequence of bases in the region(s) from which the polynucleotide is derived. As such, it may represent either a sense or an antisense orientation of the original polynucleotide.

"Recombinant" as used herein to describe a nucleic acid molecule means a polynucleotide of genomic, cDNA, viral, semisynthetic, or synthetic origin which, by virtue of its origin or manipulation is not associated with all or a portion of the polynucleotide with which it is associated in nature. The term "recombinant" as used with respect to a protein or polypeptide means a polypeptide produced by expression of a recombinant polynucleotide. In general, the gene of interest is cloned and then expressed in transformed organisms, as described further below. The host organism expresses the foreign gene to produce the protein under expression conditions.

As used herein, a "solid support" refers to a solid surface such as a magnetic bead, latex bead, microtiter plate well, glass plate, nylon, agarose, acrylamide, and the like.

As used herein, the term "target nucleic acid region" or "target nucleic acid" denotes a nucleic acid molecule with a "target sequence" to be amplified. The target nucleic acid may be either single-stranded or double-stranded and may include other sequences besides the target sequence, which may not be amplified. The term "target sequence" refers to the particular nucleotide sequence of the target nucleic acid which is to be amplified. The target sequence may include a probe-hybridizing region contained within the target molecule with which a probe will form a stable hybrid under desired conditions. The "target sequence" may also include the complexing sequences to which the oligonucleotide primers complex and extended using the target sequence as a template. Where the target nucleic acid is originally single-stranded, the term "target sequence" also refers to the sequence complementary to the "target sequence" as present in the target nucleic acid. If the "target nucleic acid" is originally double-stranded, the term "target sequence" refers to both the plus (+) and minus (−) strands (or sense and anti-sense strands).

The term "primer" or "oligonucleotide primer" as used herein, refers to an oligonucleotide that hybridizes to the template strand of a nucleic acid and initiates synthesis of a nucleic acid strand complementary to the template strand when placed under conditions in which synthesis of a primer extension product is induced, i.e., in the presence of nucleotides and a polymerization-inducing agent such as a DNA or RNA polymerase and at suitable temperature, pH, metal concentration, and salt concentration. The primer is preferably single-stranded for maximum efficiency in amplification, but may alternatively be double-stranded. If double-stranded, the primer can first be treated to separate its strands before being used to prepare extension products. This denaturation step is typically effected by heat, but may alternatively be carried out using alkali, followed by neutralization. Thus, a "primer" is complementary to a template, and complexes by hydrogen bonding or hybridization with the template to give a primer/template complex for initiation of synthesis by a polymerase, which is extended by the addition of covalently bonded bases linked at its 3' end complementary to the template in the process of DNA or RNA synthesis. Typically, dengue virus nucleic acids are amplified using at least one set of oligonucleotide primers comprising at least one forward primer and at least one reverse primer capable of hybridizing to regions of a dengue virus nucleic acid flanking the portion of the dengue virus nucleic acid to be amplified. A forward primer is complementary to the 3' end of the antigenomic dengue virus template produced during replication or amplification of dengue virus nucleic acids. A reverse primer is complementary to the 3' end of the dengue virus positive sense genomic RNA strand.

The term "amplicon" refers to the amplified nucleic acid product of a PCR reaction or other nucleic acid amplification process (e.g., ligase chain reaction (LGR), nucleic acid sequence based amplification (NASBA), transcription-mediated amplification (TMA), Q-beta amplification, strand displacement amplification, or target mediated amplification). Amplicons may comprise RNA or DNA depending on the technique used for amplification. For example, DNA amplicons may be generated by RT-PCR, whereas RNA amplicons may be generated by TMA/NASBA.

As used herein, the term "probe" or "oligonucleotide probe" refers to a polynucleotide, as defined above, that contains a nucleic acid sequence complementary to a nucleic acid sequence present in the target nucleic acid analyte. The polynucleotide regions of probes may be composed of DNA, and/or RNA, and/or synthetic nucleotide analogs. Probes may be labeled in order to detect the target sequence. Such a label may be present at the 5' end, at the 3' end, at both the 5' and 3' ends, and/or internally. The "oligonucleotide probe" may contain at least one fluorescer and at least one quencher. Quenching of fluorophore fluorescence may be eliminated by exonuclease cleavage of the fluorophore from the oligonucleotide (e.g., TaqMan assay) or by hybridization of the oligonucleotide probe to the nucleic acid target sequence (e.g., molecular beacons). Additionally, the oligonucleotide probe will typically be derived from a sequence that lies between the sense and the antisense primers when used in a nucleic acid amplification assay.

As used herein, the term "capture oligonucleotide" refers to an oligonucleotide that contains a nucleic acid sequence complementary to a nucleic acid sequence present in the target nucleic acid analyte such that the capture oligonucleotide can "capture" the target nucleic acid. One or more capture oligonucleotides can be used in order to capture the target analyte. The polynucleotide regions of a capture oligonucleotide may be composed of DNA, and/or RNA, and/or synthetic nucleotide analogs. By "capture" is meant that the analyte can be separated from other components of the sample by virtue of the binding of the capture molecule to the analyte. Typically, the capture molecule is associated with a solid support, either directly or indirectly.

It will be appreciated that the hybridizing sequences need not have perfect complementarity to provide stable hybrids. In many situations, stable hybrids will form where fewer than about 10% of the bases are mismatches, ignoring loops of four or more nucleotides. Accordingly, as used herein the term "complementary" refers to an oligonucleotide that forms a stable duplex with its "complement" under assay conditions, generally where there is about 90% or greater homology.

The terms "hybridize" and "hybridization" refer to the formation of complexes between nucleotide sequences which are sufficiently complementary to form complexes via Watson-Crick base pairing. Where a primer "hybridizes" with target (template), such complexes (or hybrids) are sufficiently stable to serve the priming function required by, e.g., the DNA polymerase to initiate DNA synthesis.

As used herein, the term "binding pair" refers to first and second molecules that specifically bind to each other, such as complementary polynucleotide pairs capable of forming nucleic acid duplexes. "Specific binding" of the first member of the binding pair to the second member of the binding pair in a sample is evidenced by the binding of the first member to the second member, or vice versa, with greater affinity and specificity than to other components in the sample. The binding between the members of the binding pair is typically noncovalent. Unless the context clearly indicates otherwise, the terms "affinity molecule" and "target analyte" are used herein to refer to first and second members of a binding pair, respectively.

The terms "specific-binding molecule" and "affinity molecule" are used interchangeably herein and refer to a molecule that will selectively bind, through chemical or physical means to a detectable substance present in a sample. By "selectively bind" is meant that the molecule binds preferentially to the target of interest or binds with greater affinity to the target than to other molecules. For example, a DNA molecule will bind to a substantially complementary sequence and not to unrelated sequences. An oligonucleotide that "specifically binds" to a particular type of dengue virus, such as a particular serotype of dengue virus (e.g., dengue-1, dengue-2, dengue-3, or dengue-4), denotes an oligonucleotide, e.g., a primer, probe or a capture oligonucleotide, that binds to the particular dengue virus serotype, but does not bind to a sequence from other types of dengue viruses.

The terms "selectively detects" or "selectively detecting" refer to the detection of dengue virus nucleic acids using oligonucleotides, e.g., primers, probes and/or capture oligonucleotides that are capable of detecting a particular dengue virus nucleic acid, for example, by amplifying and/or binding to at least a portion of an RNA segment from a particular type of dengue virus, such as a particular dengue virus serotype (e.g., dengue-1, dengue-2, dengue-3, or dengue-4), but do not amplify and/or bind to sequences from other types of dengue viruses under appropriate hybridization conditions.

The "melting temperature" or "Tm" of double-stranded DNA is defined as the temperature at which half of the helical structure of DNA is lost due to heating or other dissociation of the hydrogen bonding between base pairs, for example, by acid or alkali treatment, or the like. The $T_m$ of a DNA molecule depends on its length and on its base composition. DNA molecules rich in GC base pairs have a higher $T_m$ than those having an abundance of AT base pairs. Separated complementary strands of DNA spontaneously reassociate or anneal to form duplex DNA when the temperature is lowered below the $T_m$. The highest rate of nucleic acid hybridization occurs approximately 25 degrees C. below the $T_m$. The $T_m$ may be estimated using the following relationship: $T_m$=69.3+0.41 (GC) % (Marmur et al. (1962) *J. Mol. Biol.* 5:109-118).

As used herein, a "biological sample" refers to a sample of cells, tissue, or fluid isolated from a subject, including but not limited to, for example, blood, plasma, serum, fecal matter, urine, bone marrow, bile, spinal fluid, lymph fluid, samples of the skin, external secretions of the skin, respiratory, intestinal, and genitourinary tracts, tears, saliva, milk, blood cells (e.g., peripheral blood mononuclear cells), organs (e.g., liver, lung, spleen, thymus, kidney, or lymph node), biopsies and also samples of in vitro cell culture constituents including but not limited to conditioned media resulting from the growth of cells and tissues in culture medium, e.g., recombinant cells, and cell components.

As used herein, the terms "label" and "detectable label" refer to a molecule capable of detection, including, but not limited to, radioactive isotopes, fluorescers, chemiluminescers, chromophores, enzymes, enzyme substrates, enzyme cofactors, enzyme inhibitors, semiconductor nanoparticles, dyes, metal ions, metal sols, ligands (e.g., biotin, strepavidin or haptens) and the like. The term "fluorescer" refers to a substance or a portion thereof which is capable of exhibiting fluorescence in the detectable range. Particular examples of labels which may be used in the practice of the invention include, but are not limited to, horseradish peroxidase (HRP), SYBR® green, SYBR® gold, fluorescein, carboxyfluorescein (FAM), CAL Fluor Orange 560, CAL Fluor Red 610, Quasar Blue 670, tetramethyl rhodamine (TAMRA), 2',4',5',7'-tetrachloro-4-7-dichlorofluorescein (TET), FITC, rhodamine, dansyl, umbelliferone, dimethyl acridinium ester (DMAE), Texas red, luminol, NADPH, and α-β-galactosidase.

A "molecular beacon" probe is a single-stranded oligonucleotide, typically 25 to 40 bases-long, in which the bases on the 3' and 5' ends are complementary forming a "stem,"

typically for 5 to 8 base pairs. A molecular beacon probe forms a hairpin structure at temperatures at and below those used to anneal the primers to the template (typically below about 60° C.). The double-helical stem of the hairpin brings a fluorophore (or other label) attached to the 5' end of the probe in proximity to a quencher attached to the 3' end of the probe. The probe does not fluoresce (or otherwise provide a signal) in this conformation. If a probe is heated above the temperature needed to melt the double stranded stem apart, or the probe hybridizes to a target nucleic acid that is complementary to the sequence within the single-strand loop of the probe, the fluorophore and the quencher are separated, and the fluorophore fluoresces in the resulting conformation. Therefore, in a series of PCR cycles the strength of the fluorescent signal increases in proportion to the amount of the molecular beacon that is hybridized to the amplicon, when the signal is read at the annealing temperature. Molecular beacons of high specificity, having different loop sequences and conjugated to different fluorophores, can be selected in order to monitor increases in amplicons that differ by as little as one base (Tyagi, S. and Kramer, F. R. (1996), Nat. Biotech. 14:303 308; Tyagi, S. et al., (1998), Nat. Biotech. 16: 49 53; Kostrikis, L. G. et al., (1998), Science 279: 1228 1229; all of which are herein incorporated by reference).

By "subject" is meant any member of the subphylum chordata, including, without limitation, humans and other primates, including non-human primates such as chimpanzees and other apes and monkey species; farm animals such as cattle, sheep, pigs, goats and horses; domestic mammals such as dogs and cats; birds; and laboratory animals, including rodents such as mice, rats and guinea pigs, and the like. The term does not denote a particular age. Thus, both adult and newborn individuals are intended to be covered.

2. Modes of Carrying Out the Invention

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of methods and materials similar or equivalent to those described herein can be used in the practice of the present invention, the preferred materials and methods are described herein.

The present invention is based on the discovery of reagents and methods for diagnosing infection caused by dengue viruses, including in particular, the human pathogenic dengue viruses of serotypes 1-4. The methods are useful for detecting dengue virus in biological samples such as blood samples, including without limitation, in whole blood, serum and plasma. Thus, the methods can be used to diagnose dengue virus infection in a subject, as well as to detect dengue virus contamination in donated blood samples. Aliquots from individual donated samples or pooled samples can be screened for the presence of dengue virus and those samples or pooled samples contaminated with dengue virus can be eliminated before they are combined. In this way, a blood supply substantially free of dengue virus contamination can be provided.

Dengue virus can also be detected in cell or tissue samples in which the virus proliferates, including, but not limited to peripheral blood mononuclear cells and tissue samples obtained from the liver, lung, spleen, thymus, kidneys, lymph nodes, or bone marrow. The, dengue virus can be specifically detected even in samples containing other viruses, such as West Nile virus, Japanese encephalitis virus, tick-born encephalitis virus, human immunodeficiency virus (HIV), and/or hepatitis C virus (HCV). Moreover, the methods described herein can be used to screen mosquitoes, primates, and other hosts for dengue virus in order to determine if a particular insect or animal population is infected with the virus, thereby preventing further transmission and spread of dengue virus infection.

The methods use oligonucleotide reagents (e.g., oligonucleotide primers and probes) or a combination of reagents capable of detecting one or more pathogenic dengue viruses in a single assay. In one format, primer pairs and probes capable of detecting one or more pathogenic dengue viruses are used. For example, certain primers and probes are from "conserved" regions and therefore capable of detecting more than one pathogenic dengue virus, such as any combination of two or more dengue viruses pathogenic in humans, for example, two or more serotypes of dengue virus (e.g., both dengue-1 and dengue-3; or dengue-1, dengue-2, and dengue-3).

By way of example, the 5' UTR and capsid coding sequences of dengue virus include conserved regions. Thus, primers and probes comprising sequences from these regions, or the corresponding regions in other pathogenic dengue viruses, may be useful in detecting multiple pathogenic dengue viruses.

Other primers and probes are highly selective for a particular dengue virus, selectively amplifying, detecting and/or binding to a particular RNA segment from one of the dengue virus serotypes 1-4. These highly selective primers and probes can be used alone or in combination to detect one or more dengue viruses in a single assay.

Thus, there are a number of assay designs that can be used to detect human pathogenic serotypes alone or in combination with each other. In one embodiment, "conserved" primers (i.e., those primers that amplify more than one dengue virus) can be used to detect one or more of the dengue virus serotypes, as specified above. For example, conserved primers and probes can be used to amplify and detect multiple serotypes. Alternatively, serotype-specific primers and probe(s) can be used to achieve specificity. For example, a single pathogenic serotype (e.g., dengue-1, dengue-2, dengue-3, or dengue-4) can be amplified with serotype-specific primers and detected with the corresponding serotype-specific probes. One or more serotypes can be amplified and detected simultaneously by using a combination of serotype-specific primers and probes in a multiplex-type assay format.

Thus, the probes and primers may be designed from conserved nucleotide regions of the polynucleotides of interest or from non-conserved nucleotide regions of the polynucleotide of interest. Generally, nucleic acid probes are developed from non-conserved or unique regions when maximum specificity is desired, and nucleic acid probes are developed from conserved regions when assaying for nucleotide regions that are closely related to, for example, different dengue virus isolates.

Oligonucleotides for use in the assays described herein can be derived from the 5' UTR and capsid coding sequences of dengue viruses. Representative sequences from dengue isolates are listed herein. Thus, primers and probes for use in detection of dengue virus include those derived from any one of the four dengue virus serotypes, including any pathogenic dengue virus strain or isolate.

Representative sequences from dengue virus are known and are presented in SEQ ID NOS:1-4 of the Sequence Listing. Additional representative sequences, including sequences of the 5'-untranslated region (UTR) and coding region for the capsid protein C from dengue virus isolates are listed in the National Center for Biotechnology Information (NCBI) database. See, for example, NCBI entries: Accession No. NC_001477, Accession No. NC_001474, Accession No. NC_001475, Accession No. NC_002640, Accession No. AB609588, Accession No. EU848545, Accession No. AB609589, Accession No. AF038403, Accession No. AF038402, Accession No. M29095, Accession No. M93130, Accession No. AB609590, Accession No. AB609591, Accession No. S66064, Accession No. AY947539, Accession No. JN559741, Accession No. JN559740, Accession No. JF357906, Accession No. HQ634199, Accession No. HQ541794, Accession No. EU076567, Accession No. EU076565, Accession No. EU076563, Accession No. EU076561, Accession No. JQ950328, Accession No. JN796245, Accession No. JN819424, Accession No. JN819422, Accession No. JN819414, Accession No. JN819412, Accession No. JN819406, Accession No. JN819417, Accession No. JN819415, Accession No. JN819409, Accession No. JN093514, Accession No. JF730055, Accession No. JN000937, Accession No. JF937647, Accession No. JN819406, Accession No. GQ868543; all of which sequences (as entered by the date of filing of this application) are herein incorporated by reference. See also Weaver et al. (2009) Infect. Genet. Evol. 9(4):523-540 and Rico-Hesse (2003) Adv. Virus Res. 59:315-341 for sequence comparisons and a discussion of genetic diversity and phylogenetic analysis of dengue viruses.

Primers and probes for use in the assays herein are derived from these sequences and are readily synthesized by standard techniques, e.g., solid phase synthesis via phosphoramidite chemistry, as disclosed in U.S. Pat. Nos. 4,458,066 and 4,415,732, incorporated herein by reference; Beaucage et al., *Tetrahedron* (1992) 48:2223-2311; and Applied Biosystems User Bulletin No. 13 (1 Apr. 1987). Other chemical synthesis methods include, for example, the phosphotriester method described by Narang et al., *Meth. Enzymol.* (1979) 68:90 and the phosphodiester method disclosed by Brown et al., *Meth. Enzymol.* (1979) 68:109. Poly(A) or poly(C), or other non-complementary nucleotide extensions may be incorporated into oligonucleotides using these same methods. Hexaethylene oxide extensions may be coupled to the oligonucleotides by methods known in the art. Cload et al., *J. Am. Chem. Soc.* (1991) 113:6324-6326; U.S. Pat. No. 4,914,210 to Levenson et al.; Durand et al., *Nucleic Acids Res.* (1990) 18:6353-6359; and Horn et al., *Tet. Lett.* (1986) 27:4705-4708.

Additionally, nucleic acids can be obtained directly from the dengue virus in question. Several members of the dengue virus family are available from the ATCC as follows: Dengue virus type 2 from a patient diagnosed with Thai hemorrhagic fever, Thailand, 1958 (ATCC Accession No. VR-345); Dengue virus type 1 from pooled serum from 6 patients, strain Hawaii, 1944 (ATCC Accession No. VR-1254); Dengue virus type 4 from clinical specimen, strain H241, Philippines, 1956 (ATCC Accession No. VR-1257); Dengue virus type 4 derived from existing strain ATCC VR-217 (ATCC Accession No. VR-1490); Dengue virus type 2 from serum of a febrile patient, New Guinea, 1944 (ATCC Accession No. VR-1584); and Dengue virus type 1, strain TH-S-man (ATCC Accession No. VR-1586).

Alternatively, dengue virus can be isolated from infected mosquitoes or primates. Once obtained, the virus can be propagated using known techniques (see, e.g., World Health Organization. (2009) Dengue: guidelines for diagnosis, treatment, prevention, and control. Geneva: TDR: World Health Organization). Generally, dengue viruses are grown in cell culture. The mosquito cell line C6/36 (cloned from *Ae. albopictus*) or AP61 (cell line from *Ae. pseudoscutellaris*) are routinely used for isolation of dengue virus (see, e.g., Bona et al. (2012) Rev. Soc. Bras. Med. Trop. 45(3): 297-300; Rocco et al. (2012) Rev. Inst. Med. Trop. Sao Paulo. 54(1):49-51; and Hober et al. (1996) Immunol. Lett. 53(2-3):115-120). Several mammalian cell lines, such as Vero, LLCMK2, and BHK21, may also be used but are less efficient (Alvarez et al. (2005) Dengue Bulletin 29:1-9). Clinical specimens may also be inoculated intracranially in suckling mice or intrathoracically in mosquitoes (see, e.g., Zompi et al. (2012) Viruses 4(1):62-82; Costa et al. (2012) PLoS Negl. Trop. Dis. 6(5):e1663; Weng et al. (2000) J. Med. Entomol. 37(4):641-644).

An amplification method such as PCR or nucleic acid sequence based amplification (NASBA) can be used to amplify polynucleotides from either dengue virus genomic RNA or cDNA derived therefrom. Alternatively, polynucleotides can be synthesized in the laboratory, for example, using an automatic synthesizer.

Typically, the primer oligonucleotides are in the range of between 10-100 nucleotides in length, such as 15-60, 20-40 and so on, more typically in the range of between 20-40 nucleotides long, and any length between the stated ranges. In certain embodiments, a primer oligonucleotide comprises a sequence selected from the group consisting of SEQ ID NOS:5-12; or a fragment thereof comprising at least about 6 contiguous nucleotides, preferably at least about 8 contiguous nucleotides, more preferably at least about 10-12 contiguous nucleotides, and even more preferably at least about 15-20 contiguous nucleotides; or a variant thereof comprising a sequence having at least about 80-100% sequence identity thereto, including any percent identity within this range, such as 81, 82, 83, 84, 85, 86, 87, 88, 89, 90, 91, 92, 93, 94, 95, 96, 97, 98, or 99% sequence identity thereto. Changes to the nucleotide sequences of SEQ ID NOS:5-12 may be introduced corresponding to genetic variations in particular Dengue strains. In certain embodiments, up to three nucleotide changes, including 1 nucleotide change, 2 nucleotide changes, or three nucleotide changes, may be made in a sequence selected from the group consisting of SEQ ID NOS:5-12, wherein the oligonucleotide primer is capable of hybridizing to and amplifying a particular dengue virus target nucleic acid.

The typical probe oligonucleotide is in the range of between 10-100 nucleotides long, such as 10-60, 15-40, 18-30, and so on, and any length between the stated ranges. In certain embodiments, a probe oligonucleotide comprises a sequence selected from the group consisting of SEQ ID NOS:13-21; or a fragment thereof comprising at least about 6 contiguous nucleotides, preferably at least about 8 contiguous nucleotides, more preferably at least about 10-12 contiguous nucleotides, and even more preferably at least about 15-20 contiguous nucleotides; or a variant thereof comprising a sequence having at least about 80-100% sequence identity thereto, including any percent identity within this range, such as 81, 82, 83, 84, 85, 86, 87, 88, 89, 90, 91, 92, 93, 94, 95, 96, 97, 98, or 99% sequence identity thereto. Changes to the nucleotide sequences of SEQ ID NOS:13-21 may be introduced corresponding to genetic variations in particular Dengue strains. In certain embodiments, up to three nucleotide changes, including 1 nucleotide change, 2 nucleotide changes, or three nucleotide changes, may be made in a sequence selected from the group consisting of SEQ ID NOS:13-21, wherein the oligonucleotide probe is capable of hybridizing to and detecting a particular dengue virus target nucleic acid.

Moreover, the oligonucleotides, particularly the probe oligonucleotides, may be coupled to labels for detection. There are several means known for derivatizing oligonucleotides with reactive functionalities which permit the addition of a label. For example, several approaches are available for biotinylating probes so that radioactive, fluorescent, chemiluminescent, enzymatic, or electron dense labels can be attached via avidin. See, e.g., Broken et al., *Nucl. Acids Res.* (1978) 5:363-384 which discloses the use of ferritin-avidin-biotin labels; and Chollet et al., *Nucl. Acids Res.* (1985) 13:1529-1541 which discloses biotinylation of the 5' termini of oligonucleotides via an aminoalkylphosphoramide linker arm. Several methods are also available for synthesizing amino-derivatized oligonucleotides which are readily labeled by fluorescent or other types of compounds derivatized by amino-reactive groups, such as isothiocyanate, N-hydroxysuccinimide, or the like, see, e.g., Connolly, *Nucl. Acids Res.* (1987) 15:3131-3139, Gibson et al. *Nucl. Acids Res.* (1987) 15:6455-6467 and U.S. Pat. No. 4,605,735 to Miyoshi et al. Methods are also available for synthesizing sulfhydryl-derivatized oligonucleotides, which can be reacted with thiol-specific labels, see, e.g., U.S. Pat. No. 4,757,141 to Fung et al., Connolly et al., *Nucl. Acids Res.* (1985) 13:4485-4502 and Spoat et al. *Nucl. Acids Res.* (1987) 15:4837-4848. A comprehensive review of methodologies for labeling DNA fragments is provided in Matthews et al., *Anal. Biochem.* (1988) 169:1-25.

For example, oligonucleotides may be fluorescently labeled by linking a fluorescent molecule to the non-ligating terminus of the molecule. Guidance for selecting appropriate fluorescent labels can be found in Smith et al., *Meth. Enzymol.* (1987) 155:260-301; Karger et al., *Nucl. Acids Res.* (1991) 19:4955-4962; Guo et al. (2012) Anal. Bioanal. Chem. 402(10):3115-3125; and *Molecular Probes Handbook, A Guide to Fluorescent Probes and Labeling Technologies,* 11$^{th}$ edition, Johnson and Spence eds., 2010 (Molecular Probes/Life Technologies). Fluorescent labels include fluorescein and derivatives thereof, such as disclosed in U.S. Pat. No. 4,318,846 and Lee et al., *Cytometry* (1989) 10:151-164. Dyes for use in the present invention include 3-phenyl-7-isocyanatocoumarin, acridines, such as 9-isothiocyanatoacridine and acridine orange, pyrenes, benzoxadiazoles, and stilbenes, such as disclosed in U.S. Pat. No. 4,174,384. Additional dyes include SYBR green, SYBR gold, Yakima Yellow, Texas Red, 3-(ε-carboxypentyl)-3'-ethyl-5,5'-dimethyloxacarbocyanine (CYA); 6-carboxy fluorescein (FAM); CAL Fluor Orange 560, CAL Fluor Red 610, Quasar Blue 670; 5,6-carboxyrhodamine-110 (R110); 6-carboxyrhodamine-6G (R6G); N',N',N',N'-tetramethyl-6-carboxyrhodamine (TAMRA); 6-carboxy-X-rhodamine (ROX); 2',4',5',7'-tetrachloro-4-7-dichlorofluorescein (TET); 2',7'-dimethoxy-4',5'-6 carboxyrhodamine (JOE); 6-carboxy-2',4,4',5',7,7'-hexachlorofluorescein (HEX); Dragonfly orange; ATTO-Tec; Bodipy; ALEXA; VIC, Cy3, and Cy5. These dyes are commercially available from various suppliers such as Life Technologies (Carlsbad, Calif.), Biosearch Technologies (Novato, Calif.), and Integrated DNA Technolgies (Coralville, Iowa). Fluorescent labels include fluorescein and derivatives thereof, such as disclosed in U.S. Pat. No. 4,318,846 and Lee et al., *Cytometry* (1989) 10:151-164, and 6-FAM, JOE, TAMRA, ROX, HEX-1, HEX-2, ZOE, TET-1 or NAN-2, and the like.

Oligonucleotides can also be labeled with a minor groove binding (MGB) molecule, such as disclosed in U.S. Pat. No. 6,884,584, U.S. Pat. No. 5,801,155; Afonina et al. (2002) Biotechniques 32:940-944, 946-949; Lopez-Andreo et al. (2005) Anal. Biochem. 339:73-82; and Belousov et al. (2004) Hum Genomics 1:209-217. Oligonucleotides having a covalently attached MGB are more sequence specific for their complementary targets than unmodified oligonucleotides. In addition, an MGB group increases hybrid stability with complementary DNA target strands compared to unmodified oligonucleotides, allowing hybridization with shorter oligonucleotides.

Additionally, oligonucleotides can be labeled with an acridinium ester (AE) using the techniques described below. Current technologies allow the AE label to be placed at any location within the probe. See, e.g., Nelson et al., (1995) "Detection of Acridinium Esters by Chemiluminescence" in *Nonisotopic Probing, Blotting and Sequencing,* Kricka L. J. (ed) Academic Press, San Diego, Calif.; Nelson et al. (1994) "Application of the Hybridization Protection Assay (HPA) to PCR" in *The Polymerase Chain Reaction,* Mullis et al. (eds.) Birkhauser, Boston, Mass.; Weeks et al., *Clin. Chem.* (1983) 29:1474-1479; Berry et al., *Clin. Chem.* (1988) 34:2087-2090. An AE molecule can be directly attached to the probe using non-nucleotide-based linker arm chemistry that allows placement of the label at any location within the probe. See, e.g., U.S. Pat. Nos. 5,585,481 and 5,185,439.

In certain embodiments, molecular beacon probes may be used for detection of dengue virus target nucleic acids. Molecular beacons are hairpin shaped oligonucleotides with an internally quenched fluorophore. Molecular beacons typically comprise four parts: a loop of about 18-30 nucleotides, which is complementary to the target nucleic acid sequence; a stem formed by two oligonucleotide regions that are complementary to each other, each about 5 to 7 nucleotide residues in length, on either side of the loop; a fluorophore covalently attached to the 5' end of the molecular beacon, and a quencher covalently attached to the 3' end of the molecular beacon. When the beacon is in its closed hairpin conformation, the quencher resides in proximity to the fluorophore, which results in quenching of the fluorescent emission from the fluorophore. In the presence of a target nucleic acid having a region that is complementary to the strand in the molecular beacon loop, hybridization occurs resulting in the formation of a duplex between the target nucleic acid and the molecular beacon. Hybridization disrupts intramolecular interactions in the stem of the molecular beacon and causes the fluorophore and the quencher of the molecular beacon to separate resulting in a fluorescent signal from the fluorophore that indicates the presence of the target nucleic acid sequence. See, e.g., Guo et al. (2012) Anal. Bioanal. Chem. 402(10):3115-3125; Wang et al. (2009) Angew. Chem. Int. Ed. Engl. 48(5):856-870; and Li et al. (2008) Biochem. Biophys. Res. Commun. 373(4):457-461; herein incorporated by reference in their entireties.

Representative dengue virus primers and probes derived from the 5' UTR and capsid coding regions for use in the various assays are shown in Example 1 in Tables 1 and 2, respectively. The oligonucleotides labeled as dengue 1, dengue 2, dengue 3, or dengue 4-specific are oligonucleotides that selectively amplify, detect, and/or hybridize to dengue 1, dengue 2, dengue 3, or dengue 4 nucleic acids, respectively, and can therefore be used to specifically identify these viruses in the assays described herein. Accordingly, for example, dengue 2-specific oligonucleotides could be used in combination with dengue 3-specific oligonucleotides in order to test for the presence of either dengue 2 or dengue 3 in a single assay. Similarly, dengue 1 and dengue 3-specific oligonucleotides could be used in combination with dengue 2-specific oligonucleotides and dengue-4 specific oligonucleotides in order to test for the presence of dengue 1, dengue 2, dengue 3, or dengue 4 in a single assay. Also shown in Table 2 are oligonucleotide probes useful for detecting specific serotypes of dengue virus, including serotypes 1-4. It is to be understood that the primers and probes described herein are merely representative, and other oligonucleotides derived from various pathogenic dengue virus strains will find use in the assays described herein.

When utilizing a hybridization-based detection system, a nucleic acid probe is chosen that is complementary to a target nucleic acid sequence. By selection of appropriate conditions, the probe and the target sequence "selectively hybridize," or bind, to each other to form a hybrid molecule. An oligonucleotide that "selectively hybridizes" to a particular dengue virus sequence from a particular serotype under hybridization conditions described below, denotes an oligonucleotide, e.g., a primer or probe oligonucleotide, that binds to the dengue virus sequence of that particular dengue serotype, but does not bind to a sequence from a dengue virus of a different serotype.

In one embodiment of the present invention, a nucleic acid molecule is capable of hybridizing selectively to a target sequence under moderately stringent hybridization conditions. In the context of the present invention, moderately stringent hybridization conditions allow detection of a target nucleic acid sequence of at least 14 nucleotides in length having at least approximately 70% sequence identity with the sequence of the selected nucleic acid probe. In another embodiment, such selective hybridization is performed under stringent hybridization conditions. Stringent hybridization conditions allow detection of target nucleic acid sequences of at least 14 nucleotides in length having a sequence identity of greater than 90% with the sequence of the selected nucleic acid probe. Hybridization conditions useful for probe/target hybridization where the probe and target have a specific degree of sequence identity, can be determined as is known in the art (see, for example, *Nucleic Acid Hybridization: A Practical Approach*, editors B. D. Hames and S. J. Higgins, (1985) Oxford; Washington, D.C.; IRL Press). Hybrid molecules can be formed, for example, on a solid support, in solution, and in tissue sections. The formation of hybrids can be monitored by inclusion of a reporter molecule, typically, in the probe. Such reporter molecules or detectable labels include, but are not limited to, radioactive elements, fluorescent markers, and molecules to which an enzyme-conjugated ligand can bind.

With respect to stringency conditions for hybridization, it is well known in the art that numerous equivalent conditions can be employed to establish a particular stringency by varying, for example, the following factors: the length and nature of probe and target sequences, base composition of the various sequences, concentrations of salts and other hybridization solution components, the presence or absence of blocking agents in the hybridization solutions (e.g., formamide, dextran sulfate, and polyethylene glycol), hybridization reaction temperature and time parameters, as well as, varying wash conditions. The selection of a particular set of hybridization conditions is well known (see, for example, Sambrook, et al., *Molecular Cloning: A Laboratory Manual*, 3rd Edition, 2001).

As explained above, the primers and probes may be used in polymerase chain reaction (PCR)-based techniques, such as RT-PCR, to detect dengue virus infection in biological samples. PCR is a technique for amplifying a desired target nucleic acid sequence contained in a nucleic acid molecule or mixture of molecules. In PCR, a pair of primers is employed in excess to hybridize to the complementary strands of the target nucleic acid. The primers are each extended by a polymerase using the target nucleic acid as a template. The extension products become target sequences themselves after dissociation from the original target strand. New primers are then hybridized and extended by a polymerase, and the cycle is repeated to geometrically increase the number of target sequence molecules. The PCR method for amplifying target nucleic acid sequences in a sample is well known in the art and has been described in, e.g., Innis et al. (eds.) PCR Protocols (Academic Press, N Y 1990); Taylor (1991) *Polymerase chain reaction: basic principles and automation*, in *PCR: A Practical Approach*, McPherson et al. (eds.) IRL Press, Oxford; Saiki et al. (1986) *Nature* 324:163; as well as in U.S. Pat. Nos. 4,683,195, 4,683,202 and 4,889,818, all incorporated herein by reference in their entireties.

In particular, PCR uses relatively short oligonucleotide primers which flank the target nucleotide sequence to be amplified, oriented such that their 3' ends face each other, each primer extending toward the other. The polynucleotide sample is extracted and denatured, preferably by heat, and hybridized with first and second primers that are present in molar excess. Polymerization is catalyzed in the presence of the four deoxyribonucleotide triphosphates (dNTPs—dATP, dGTP, dCTP and dTTP) using a primer- and template-dependent polynucleotide polymerizing agent, such as any enzyme capable of producing primer extension products, for example, *E. coli* DNA polymerase I, Klenow fragment of DNA polymerase I, T4 DNA polymerase, thermostable DNA polymerases isolated from *Thermus aquaticus* (Taq), available from a variety of sources (for example, Perkin Elmer), *Thermus thermophilus* (United States Biochemicals), *Bacillus stereothermophilus* (Bio-Rad), or *Thermococcus litoralis* ("Vent" polymerase, New England Biolabs). This results in two "long products" which contain the respective primers at their 5' ends covalently linked to the newly synthesized complements of the original strands. The reaction mixture is then returned to polymerizing conditions, e.g., by lowering the temperature, inactivating a denaturing agent, or adding more polymerase, and a second cycle is initiated. The second cycle provides the two original strands, the two long products from the first cycle, two new long products replicated from the original strands, and two "short products" replicated from the long products. The short products have the sequence of the target sequence with a primer at each end. On each additional cycle, an additional two long products are produced, and a number of short products equal to the number of long and short products remaining at the end of the previous cycle. Thus, the number of short products containing the target sequence grows exponentially with each cycle. Preferably, PCR is carried out with a commercially available thermal cycler, e.g., Perkin Elmer.

RNAs may be amplified by reverse transcribing the RNA into cDNA, and then performing PCR (RT-PCR), as described above. Alternatively, a single enzyme may be used for both steps as described in U.S. Pat. No. 5,322,770, incorporated herein by reference in its entirety. RNA may also be reverse transcribed into cDNA, followed by asymmetric gap ligase chain reaction (RT-AGLCR) as described by Marshall et al. (1994) *PCR Meth. App.* 4:80-84.

Nucleic acid sequence based amplification (NASBA) is an isothermal RNA-specific amplification method that does not require thermal cycling instrumentation. RNA is initially reverse transcribed such that the single-stranded RNA target is copied into a double-stranded DNA molecule that serves as a template for RNA transcription. Detection of the amplified RNA is typically accomplished either by electrochemiluminescence or in real-time, for example, with fluorescently labeled molecular beacon probes. See, e.g., Lau et al. (2006) Dev. Biol. (Basel) 126:7-15; and Deiman et al. (2002) Mol. Biotechnol. 20(2):163-179.

The Ligase Chain Reaction (LCR) is an alternate method for nucleic acid amplification. In LCR, probe pairs are used which include two primary (first and second) and two secondary (third and fourth) probes, all of which are employed in molar excess to the target. The first probe hybridizes to a first segment of the target strand, and the second probe hybridizes to a second segment of the target strand, the first and second segments being contiguous so that the primary probes abut one another in 5' phosphate-3' hydroxyl relationship, and so that a ligase can covalently fuse or ligate the two probes into a fused product. In addition, a third (secondary) probe can hybridize to a portion of the first probe and a fourth (secondary) probe can hybridize to a portion of the second probe in a similar abutting fashion. If the target is initially double stranded, the secondary probes also will hybridize to the target complement in the first instance. Once the ligated strand of primary probes is separated from the target strand, it will hybridize with the third and fourth probes which can be ligated to form a complementary, secondary ligated product. It is important to realize that the ligated products are functionally equivalent to either the target or its complement. By repeated cycles of hybridization and ligation, amplification of the target sequence is achieved. This technique is described more completely in EPA 320,308 to K. Backman published Jun. 16, 1989 and EPA 439,182 to K. Backman et al., published Jul. 31, 1991, both of which are incorporated herein by reference.

Other known methods for amplification of nucleic acids include, but are not limited to self-sustained sequence replication (3SR) described by Guatelli et al., Proc. Natl. Acad. Sci. USA (1990) 87:1874-1878 and J. Compton, Nature (1991) 350:91-92 (1991); Q-beta amplification; strand displacement amplification (as described in Walker et al., Clin. Chem. (1996) 42:9-13 and EPA 684,315; target mediated amplification, as described in International Publication No. WO 93/22461, and the TaqMan™ assay.

The fluorogenic 5' nuclease assay, known as the TaqMan™ assay (Perkin-Elmer), is a powerful and versatile PCR-based detection system for nucleic acid targets. Primers and probes derived from conserved and/or non-conserved regions of the dengue virus genome in question can be used in TaqMan™ analyses to detect the presence of infection in a biological sample. Analysis is performed in conjunction with thermal cycling by monitoring the generation of fluorescence signals. The assay system dispenses with the need for gel electrophoretic analysis, and is capable of generating quantitative data allowing the determination of target copy numbers. For example, standard curves can be produced using serial dilutions of previously quantified dengue viral suspensions. A standard graph can be produced with copy numbers of each of the panel members against which sample unknowns can be compared.

The fluorogenic 5' nuclease assay is conveniently performed using, for example, AmpliTaq Gold™ DNA polymerase, which has endogenous 5' nuclease activity, to digest an internal oligonucleotide probe labeled with both a fluorescent reporter dye and a quencher (see, Holland et al., Proc. Natl. Acad. Sci. USA (1991) 88:7276-7280; and Lee et al., Nucl. Acids Res. (1993) 21:3761-3766). Assay results are detected by measuring changes in fluorescence that occur during the amplification cycle as the fluorescent probe is digested, uncoupling the dye and quencher labels and causing an increase in the fluorescent signal that is proportional to the amplification of target nucleic acid.

The amplification products can be detected in solution or using solid supports. In this method, the TaqMan™ probe is designed to hybridize to a target sequence within the desired PCR product. The 5' end of the TaqMan™ probe contains a fluorescent reporter dye. The 3' end of the probe is blocked to prevent probe extension and contains a dye that will quench the fluorescence of the 5' fluorophore. During subsequent amplification, the 5' fluorescent label is cleaved off if a polymerase with 5' exonuclease activity is present in the reaction. Excision of the 5' fluorophore results in an increase in fluorescence that can be detected.

For a detailed description of the TaqMan™ assay, reagents and conditions for use therein, see, e.g., Holland et al., Proc. Natl. Acad. Sci, U.S.A. (1991) 88:7276-7280; U.S. Pat. Nos. 5,538,848, 5,723,591, and 5,876,930, all incorporated herein by reference in their entireties.

A class of quenchers, known as "Black Hole Quenchers" such as BHQ1 and BHQ2, can be used in the nucleic acid assays described above. These quenchers reduce background and improve signal to noise in PCR assays. These quenchers are described in, e.g., Johansson et al., J. Chem. Soc. (2002) 124:6950-6956 and are commercially available from Biosearch Technologies (Novato, Calif.).

While the length of the primers and probes can vary, the probe sequences are selected such that they have a higher melt temperature than the primer sequences. Preferably, the probe sequences have an estimated melt temperature that is about 10° C. higher than the melt temperature for the amplification primer sequences. Hence, the primer sequences are generally shorter than the probe sequences. Typically, the primer sequences are in the range of between 10-75 nucleotides long, more typically in the range of 20-45. The typical probe is in the range of between 10-50 nucleotides long, more typically 15-40 nucleotides in length. Representative primers and probes useful in nucleic acid amplification assays are described above.

The dengue virus sequences described herein may also be used as a basis for transcription-mediated amplification (TMA) assays. TMA is an isothermal, autocatalytic nucleic acid target amplification system that can provide more than a billion RNA copies of a target sequence, and thus provides a method of identifying target nucleic acid sequences present in very small amounts in a biological sample. For a detailed description of TMA assay methods, see, e.g., Hill (2001) Expert Rev. Mol. Diagn. 1:445-55; WO 89/1050; WO 88/10315; EPO Publication No. 408,295; EPO Application No. 8811394-8.9; WO91/02818; U.S. Pat. Nos. 5,399,491, 6,686,156, and 5,556,771, all incorporated herein by reference in their entireties.

Suitable DNA polymerases include reverse transcriptases, such as avian myeloblastosis virus (AMV) reverse transcriptase (available from, e.g., Seikagaku America, Inc.) and Moloney murine leukemia virus (MMLV) reverse transcriptase (available from, e.g., Bethesda Research Laboratories).

Promoters or promoter sequences suitable for incorporation in the primers are nucleic acid sequences (either naturally occurring, produced synthetically or a product of a restriction digest) that are specifically recognized by an RNA polymerase that recognizes and binds to that sequence and initiates the process of transcription whereby RNA transcripts are produced. The sequence may optionally include nucleotide bases extending beyond the actual recognition site for the RNA polymerase which may impart added stability or susceptibility to degradation processes or increased transcription efficiency. Examples of useful promoters include those which are recognized by certain bacteriophage polymerases such as those from bacteriophage T3, T7 or SP6, or a promoter from *E. coli*. These RNA polymerases are readily available from commercial sources, such as New England Biolabs and Epicentre.

Some of the reverse transcriptases suitable for use in the methods herein have an RNAse H activity, such as AMV reverse transcriptase. It may, however, be preferable to add exogenous RNAse H, such as *E. coli* RNAse H, even when AMV reverse transcriptase is used. RNAse H is readily available from, e.g., Bethesda Research Laboratories.

The RNA transcripts produced by these methods may serve as templates to produce additional copies of the target sequence through the above-described mechanisms. The system is autocatalytic and amplification occurs autocatalytically without the need for repeatedly modifying or changing reaction conditions such as temperature, pH, ionic strength or the like.

Detection may be done using a wide variety of methods, including direct sequencing, hybridization with sequence-specific oligomers, gel electrophoresis and mass spectrometry. These methods can use heterogeneous or homogeneous formats, isotopic or nonisotopic labels, as well as no labels at all.

One method of detection is the use of target sequence-specific oligonucleotide probes described above. The probes may be used in hybridization protection assays (HPA). In this embodiment, the probes are conveniently labeled with acridinium ester (AE), a highly chemiluminescent molecule. See, e.g., Nelson et al. (1995) "Detection of Acridinium Esters by Chemiluminescence" in *Nonisotopic Probing, Blotting and Sequencing*, Kricka L. J. (ed) Academic Press, San Diego, Calif.; Nelson et al. (1994) "Application of the Hybridization Protection Assay (HPA) to PCR" in *The Polymerase Chain Reaction*, Mullis et al. (eds.) Birkhauser, Boston, Mass.; Weeks et al., *Clin. Chem.* (1983) 29:1474-1479; Berry et al., *Clin. Chem.* (1988) 34:2087-2090. One AE molecule is directly attached to the probe using a non-nucleotide-based linker arm chemistry that allows placement of the label at any location within the probe. See, e.g., U.S. Pat. Nos. 5,585,481 and 5,185,439. Chemiluminescence is triggered by reaction with alkaline hydrogen peroxide which yields an excited N-methyl acridone that subsequently collapses to ground state with the emission of a photon.

When the AE molecule is covalently attached to a nucleic acid probe, hydrolysis is rapid under mildly alkaline conditions. When the AE-labeled probe is exactly complementary to the target nucleic acid, the rate of AE hydrolysis is greatly reduced. Thus, hybridized and unhybridized AE-labeled probe can be detected directly in solution, without the need for physical separation.

HPA generally consists of the following steps: (a) the AE-labeled probe is hybridized with the target nucleic acid in solution for about 15 to about 30 minutes. A mild alkaline solution is then added and AE coupled to the unhybridized probe is hydrolyzed. This reaction takes approximately 5 to 10 minutes. The remaining hybrid-associated AE is detected as a measure of the amount of target present. This step takes approximately 2 to 5 seconds. Preferably, the differential hydrolysis step is conducted at the same temperature as the hybridization step, typically at 50 to 70° C. Alternatively, a second differential hydrolysis step may be conducted at room temperature. This allows elevated pHs to be used, for example in the range of 10-11, which yields larger differences in the rate of hydrolysis between hybridized and unhybridized AE-labeled probe. HPA is described in detail in, e.g., U.S. Pat. Nos. 6,004,745; 5,948,899; and 5,283,174, the disclosures of which are incorporated by reference herein in their entireties.

In one example of a typical TMA assay, an isolated nucleic acid sample, suspected of containing a dengue virus target sequence, is mixed with a buffer concentrate containing the buffer, salts, magnesium, nucleotide triphosphates, primers, dithiothreitol, and spermidine. The reaction is optionally incubated at about 100° C. for approximately two minutes to denature any secondary structure. After cooling to room temperature, reverse transcriptase, RNA polymerase, and RNAse H are added and the mixture is incubated for two to four hours at 37° C. The reaction can then be assayed by denaturing the product, adding a probe solution, incubating 20 minutes at 60° C., adding a solution to selectively hydrolyze the unhybridized probe, incubating the reaction six minutes at 60° C., and measuring the remaining chemiluminescence in a luminometer.

The methods of detection of the invention utilize a biological sample suspected of containing dengue virus nucleic acids. A biological sample may be pre-treated in any number of ways prior to assay for dengue virus nucleic acids. For instance, in certain embodiments, the sample may be treated to disrupt (or lyse) any viral particles (virions), for example by treating the samples with one or more detergents and/or denaturing agents (e.g., guanidinium agents). Nucleic acids may also be extracted from samples, for example, after detergent treatment and/or denaturing as described above. Total nucleic acid extraction may be performed using known techniques, for example by non-specific binding to a solid phase (e.g., silica). See, e.g., U.S. Pat. Nos. 5,234,809, 6,849,431; 6,838,243; 6,815,541; and 6,720,166.

In certain embodiments, the target nucleic acids are separated from non-homologous nucleic acids using capture oligonucleotides immobilized on a solid support. Such capture oligonucleotides contain nucleic acid sequences that are complementary to a nucleic acid sequence present in the target dengue virus nucleic acid analyte such that the capture oligonucleotide can "capture" the target nucleic acid. Capture oligonucleotides can be used alone or in combination to capture dengue virus nucleic acids. For example, multiple capture oligonucleotides can be used in combination, e.g., 2, 3, 4, 5, 6, etc. different capture oligonucleotides can be attached to a solid support to capture target dengue virus nucleic acids. In certain embodiments, one or more capture oligonucleotides can be used to bind dengue virus target nucleic acids either prior to or after amplification by primer oligonucleotides and/or detection by probe oligonucleotides.

In one embodiment of the present invention the biological sample potentially carrying target nucleic acids is contacted with a solid support in association with capture oligonucleotides. The capture oligonucleotides, which may be used separately or in combination, may be associated with the solid support, for example, by covalent binding of the capture moiety to the solid support, by affinity association, hydrogen binding, or nonspecific association.

The capture oligonucleotides can include from about 5 to about 500 nucleotides of a conserved region from a dengue virus, preferably about 10 to about 100 nucleotides, or more preferably about 10 to about 60 nucleotides of the conserved region, or any integer within these ranges, such as a sequence including 18, 19, 20, 21, 22, 23, 24, 25, 26 . . . 35 . . . 40, etc. nucleotides from the conserved region of interest. In certain embodiments, the capture oligonucleotide comprises a sequence selected from the group consisting of SEQ ID NOS:5-21 or a complement thereof. The capture oligonucleotide may also be phosphorylated at the 3' end in order to prevent extension of the capture oligonucleotide.

The capture oligonucleotide may be attached to the solid support in a variety of manners. For example, the oligonucleotide may be attached to the solid support by attachment of the 3' or 5' terminal nucleotide of the probe to the solid support. More preferably, the capture oligonucleotide is attached to the solid support by a linker which serves to distance the probe from the solid support. The linker is usually at least 10-50 atoms in length, more preferably at least 15-30 atoms in length. The required length of the linker will depend on the particular solid support used. For example, a six atom linker is generally sufficient when high cross-linked polystyrene is used as the solid support.

A wide variety of linkers are known in the art which may be used to attach the oligonucleotide probe to the solid support. The linker may be formed of any compound which does not significantly interfere with the hybridization of the target sequence to the probe attached to the solid support. The linker may be formed of a homopolymeric oligonucleotide which can be readily added on to the linker by automated synthesis. The homopolymeric sequence can be either 5' or 3' to the virus-specific sequence. In one aspect of the invention, the capture oligonucleotides include a homopolymer chain, such as, for example poly A, poly T, poly G, poly C, poly U, poly dA, poly dT, poly dG, poly dC, or poly dU in order to facilitate attachment to a solid support. The homopolymer chain can be from about 10 to about 40 nucleotides in length, or preferably about 12 to about 25 nucleotides in length, or any integer within these ranges, such as for example, 10 . . . 12 . . . 16, 17, 18, 19, 20, 21, 22, 23, or 24 nucleotides. The homopolymer, if present, can be added to the 3' or 5' terminus of the capture oligonucleotides by enzymatic or chemical methods. This addition can be made by stepwise addition of nucleotides or by ligation of a preformed homopolymer. Capture oligonucleotides comprising such a homopolymer chain can be bound to a solid support comprising a complementary homopolymer. Alternatively, biotinylated capture oligonucleotides can be bound to avidin- or streptavidin-coated beads. See, e.g., Chollet et al., supra.

Alternatively, polymers such as functionalized polyethylene glycol can be used as the linker. Such polymers do not significantly interfere with the hybridization of probe to the target oligonucleotide. Examples of linkages include polyethylene glycol, carbamate and amide linkages. The linkages between the solid support, the linker and the probe are preferably not cleaved during removal of base protecting groups under basic conditions at high temperature.

The solid support may take many forms including, for example, nitrocellulose reduced to particulate form and retrievable upon passing the sample medium containing the support through a sieve; nitrocellulose or the materials impregnated with magnetic particles or the like, allowing the nitrocellulose to migrate within the sample medium upon the application of a magnetic field; beads or particles which may be filtered or exhibit electromagnetic properties; and polystyrene beads which partition to the surface of an aqueous medium. Examples of types of solid supports for immobilization of the oligonucleotide probe include controlled pore glass, glass plates, polystyrene, avidin-coated polystyrene beads, cellulose, nylon, acrylamide gel and activated dextran.

In one embodiment, the solid support comprises magnetic beads. The magnetic beads may contain primary amine functional groups, which facilitate covalent binding or association of the capture oligonucleotides to the magnetic support particles. Alternatively, the magnetic beads have immobilized thereon homopolymers, such as poly T or poly A sequences. The homopolymers on the solid support will generally be complementary to any homopolymer on the capture oligonucleotide to allow attachment of the capture oligonucleotide to the solid support by hybridization. The use of a solid support with magnetic beads allows for a one-pot method of isolation, amplification and detection as the solid support can be separated from the biological sample by magnetic means.

The magnetic beads or particles can be produced using standard techniques or obtained from commercial sources. In general, the particles or beads may be comprised of magnetic particles, although they can also include other magnetic metal or metal oxides, whether in impure, alloy, or composite form, as long as they have a reactive surface and exhibit an ability to react to a magnetic field. Other materials that may be used individually or in combination with iron include, but are not limited to, cobalt, nickel, and silicon. A magnetic bead suitable for use with the present invention includes magnetic beads containing poly dT groups marketed under the trade name Sera-Mag magnetic oligonucleotide beads by Seradyn, Indianapolis, Ind.

Next, the association of the capture oligonucleotides with the solid support is initiated by contacting the solid support with the medium containing the capture oligonucleotides. In the preferred embodiment, the magnetic beads containing poly dT groups are hybridized with the capture oligonucleotides that comprise poly dA contiguous with the capture sequence (i.e., the sequence substantially complementary to a dengue virus nucleic acid sequence) selected from the conserved single stranded region of the dengue genome. The poly dA on the capture oligonucleotide and the poly dT on the solid support hybridize thereby immobilizing or associating the capture oligonucleotides with the solid support.

In certain embodiments, the capture oligonucleotides are combined with a biological sample under conditions suitable for hybridization with target dengue virus nucleic acids prior to immobilization of the capture oligonucleotides on a solid support. The capture oligonucleotide-target nucleic acid complexes formed are then bound to the solid support. In other embodiments, a solid support with associated capture oligonucleotides is brought into contact with a biological sample under hybridizing conditions. The immobilized capture oligonucleotides hybridize to the target nucleic acids present in the biological sample. Typically, hybridization of capture oligonucleotides to the targets can be accomplished in approximately 15 minutes, but may take as long as 3 to 48 hours.

The solid support is then separated from the biological sample, for example, by filtering, centrifugation, passing through a column, or by magnetic means. The solid support may be washed to remove unbound contaminants and transferred to a suitable container (e.g., a microtiter plate). As will be appreciated by one of skill in the art, the method of separation will depend on the type of solid support selected. Since the targets are hybridized to the capture oligonucleotides immobilized on the solid support, the target strands are thereby separated from the impurities in the sample. In some cases, extraneous nucleic acids, proteins, carbohydrates, lipids, cellular debris, and other impurities may still be bound to the support, although at much lower concentrations than initially found in the biological sample. Those skilled in the art will recognize that some undesirable materials can be removed by washing the support with a washing medium. The separation of the solid support from the biological sample preferably removes at least about 70%, more preferably about 90% and, most preferably, at least about 95% or more of the non-target nucleic acids present in the sample.

As is readily apparent, design of the assays described herein is subject to a great deal of variation, and many formats are known in the art. The above descriptions are merely provided as guidance and one of skill in the art can readily modify the described protocols, using techniques well known in the art.

The above-described assay reagents, including the primers and probes, and optionally capture oligonucleotides, a solid support with bound probes, and/or reagents for performing nucleic acid amplification, such as by RT-PCR or NASBA, can be provided in kits, with suitable instructions and other necessary reagents, in order to conduct the assays as described above. The kit will normally contain in separate containers the primers and probes, control formulations (positive and/or negative), and other reagents that the assay format requires. Instructions (e.g., written, CD-ROM, DVD, etc.) for carrying out the assay usually will be included in the kit. The kit can also contain, depending on the particular assay used, other packaged reagents and materials (i.e., wash buffers, and the like). Standard assays, such as those described above, can be conducted using these kits.

In certain embodiments, the kit comprises written instructions for identifying the presence of dengue virus and at least one set of primers comprising a forward primer and a reverse primer capable of amplifying at least a portion of a dengue virus genome, said portion comprising a 5' UTR sequence or a dengue capsid coding sequence, wherein said primers are not more than about 40 nucleotides in length, wherein said set of primers is selected from the group consisting of:
  a) a forward primer comprising the sequence of SEQ ID NO:5 and a reverse primer comprising the sequence of SEQ ID NO:9;
  b) a forward primer comprising the sequence of SEQ ID NO:5 and a reverse primer comprising the sequence of SEQ ID NO:10;
  c) a forward primer comprising the sequence of SEQ ID NO:5 and a reverse primer comprising the sequence of SEQ ID NO:11;
  d) a forward primer comprising the sequence of SEQ ID NO:6 and a reverse primer comprising the sequence of SEQ ID NO:10;
  e) a forward primer comprising the sequence of SEQ ID NO:6 and a reverse primer comprising the sequence of SEQ ID NO:11;
  f) a forward primer comprising the sequence of SEQ ID NO:7 and a reverse primer comprising the sequence of SEQ ID NO:9;
  g) a forward primer comprising the sequence of SEQ ID NO:8 and a reverse primer comprising the sequence of SEQ ID NO:12;
  h) a forward primer and a reverse primer each comprising at least 10 contiguous nucleotides from the corresponding nucleotide sequences of the forward primer and reverse primer of a primer set selected from the group consisting of (a)-(g);
  i) a forward primer and a reverse primer comprising at least one nucleotide sequence that differs from the corresponding nucleotide sequence of the forward primer or reverse primer of a primer set selected from the group consisting of (a)-(g) in that the primer has up to three nucleotide changes compared to the corresponding sequence, wherein the primer is capable of hybridizing to and amplifying dengue virus nucleic acids in the nucleic acid amplification assay; and
  j) a forward primer and a reverse primer comprising nucleotide sequences that are complements of the corresponding nucleotide sequences of the forward primer and reverse primer of a primer set selected from the group consisting of (a)-(i).

In one embodiment, the kit comprises a primer comprising the sequence of SEQ ID NO:5, a primer comprising the sequence of SEQ ID NO:6, a primer comprising the sequence of SEQ ID NO:7, a primer comprising the sequence of SEQ ID NO:8, a primer comprising the sequence of SEQ ID NO:9, a primer comprising the sequence of SEQ ID NO:10, a primer comprising the sequence of SEQ ID NO:11, a primer comprising the sequence of SEQ ID NO:12, a probe comprising the sequence of SEQ ID NO:13, a probe comprising the sequence of SEQ ID NO:14, a probe comprising the sequence of SEQ ID NO:15, and a probe comprising the sequence of SEQ ID NO:16.

In one embodiment, the probe comprising the sequence of SEQ ID NO:13 further comprises a 5' FAM fluorophore and a 3' BHQ-1 quencher, the probe comprising the sequence of SEQ ID NO:14 further comprises a 5' CAL Fluor Orange 560 fluorophore and a 3' BHQ-1 quencher, the probe comprising the sequence of SEQ ID NO:15 further comprises a 5' CAL Fluor Red 610 fluorophore and a 3' BHQ-2 quencher, and the probe comprising the sequence of SEQ ID NO:16 further comprises a 5' Quasar Blue 670 fluorophore and a 3' BHQ-2 quencher.

3. Experimental

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Example 1

Single-Reaction, Multiplex, Real-Time RT-PCR for the Detection, Quantitation, and Serotyping of Dengue Viruses This study describes the design and validation of a new, single-reaction, multiplex, quantitative real-time RT-PCR assay (hereinafter referred to as the dengue multiplex rRT-PCR) for the detection and serotyping of dengue viruses from patient samples (e.g., plasma or serum). This assay targets the 5' untranslated region (UTR) and capsid gene of dengue virus and utilizes four molecular beacons for detection and serotyping. Beacons were chosen for their high sensitivity and ability to differentiate sequences differing by as little as one or two bases (Tyagi et al. (1998) *Nat. Biotechnol.* 16: 49-53). In this paper, this assay is shown to be more sensitive (both analytically and clinically) than the hemi-nested RT-PCR used for comparison (hereinafter referred to as the reference assay). It is also specific for dengue viruses, demonstrating no amplification when tested against samples containing other flaviviruses. This assay represents a significant step forward in dengue diagnostics as it maintains the sensitivity and serotyping capability of the reference molecular diagnostic test while also providing viral load monitoring and improved workflow in a simple, single-reaction format.

Methods

Objectives

To design and validate a new multiplex rRT-PCR for dengue virus and compare this assay directly to the reference assay, a hemi-nested RT-PCR. The primary hypothesis was that this dengue multiplex rRT-PCR would demonstrate performance characteristics equivalent to the reference assay with the workflow and turnaround time advantages of real-time chemistry.

Dengue Sequences and Assay Design

Publicly available dengue sequences were obtained from GenBank, accessed August, 2011. For DEN 1-3, sequences deposited since 1990 were selected and included up to 2 sequences per country per year (143 DEN 1 sequences, 181 DEN 2 sequences, 191 DEN 3 sequences). Due to the decreased number of deposited sequences for DEN 4, all complete genome sequences available for this serotype (75 DEN 4 sequences) were included. Sequences listed as sylvatic strains were rejected. Segments of these genomes were aligned using MegAlign software (DNAStar, Madison, Wis.). A consensus sequence was generated that showed bases conserved across at least 95% of isolates. This identified a region of the 5' UTR and capsid gene that was highly conserved within each dengue serotype and also moderately conserved across all serotypes.

Using the 95% consensus sequence, Beacon Designer software (Premier Biosoft, Palo Alto, Calif.) was used to generate primer and probe sets directed against segments of the 5' UTR and capsid gene for all four serotypes. These were tested using control genomic RNA for DEN 1-4, and primer and probe sets patterned on those for DEN 1 were generated for DEN 2-4 using Primer3. An alternate molecular beacon for DEN 1, containing more mismatches between serotypes, was also designed using Primer3. TaqMan probes were designed using RealTimeDesign Software (Biosearch Technologies, Novato, Calif.). The primer and probe sequences are listed in Table 1 and Table 2.

TABLE 1

Primer sequences for the dengue multiplex rRT-PCR.

| Name | Primer Sequence (5'→3') |
| --- | --- |
| Dengue 1-2-3 Forward | CAGATCTCTGATGAACAACCAACG (SEQ ID NO: 5) |
| Dengue 2 Forward C→T | CAGATCTCTGATGAATAACCAACG (SEQ ID NO: 6) |
| Dengue 3 Forward C→T | CAGATTTCTGATGAACAACCAACG (SEQ ID NO: 7) |
| Dengue 4 Forward | GATCTCTGGAAAAATGAAC (SEQ ID NO: 8) |
| Dengue 1,3 Reverse | TTTGAGAATCTCTTCGCCAAC (SEQ ID NO: 9) |
| Dengue 2 Reverse | AGTTGACACGCGGTTTCTCT (SEQ ID NO: 10) |
| Dengue 2 Reverse A→G | AGTCGACACGCGGTTTCTCT (SEQ ID NO: 11) |
| Dengue 4 Reverse | AGAATCTCTTCACCAACC (SEQ ID NO: 12) |

TABLE 2

Probe sequences for the dengue multiplex rRT-PCR.

| Channel | 5' Fluor | Probe Sequence (5'→3') | 3' Quencher |
| --- | --- | --- | --- |
| Green | FAM | CGCGATC<u>GCGTTTCAGCATATTGAAAGACGG</u>ATCGCG (SEQ ID NO: 13) | BHQ-1 |
| Yellow | CAL Fluor Orange 560 | CGCGATC<u>GCGTTTCAGCATATTGAAAGGCGG</u>ATCGCG (SEQ ID NO: 14) | BHQ-1 |
| Orange | CAL Fluor Red 610 | CGCGATC<u>CACGCGTTTCAGCATATTGATAGG</u>ATCGCG (SEQ ID NO: 15) | BHQ-2 |
| Red | Quasar Blue 670 | CGCGATC<u>TTTCAGCATATTGAAAGGTGGTC</u>GATCGCG (SEQ ID NO: 16) | BHQ-2 |

Probes are listed by the channel in which signal is detected on the Rotor-Gene Q instrument. Underlined probe segments designate sequences complimentary to the dengue consensus; segments on the 5' and 3' ends of the probe comprise the beacon stem.

| Beacon Name | 5' Fluor | Sequence | 3' Quencher |
| --- | --- | --- | --- |
| Den1 Alternate | FAM | CGCGATCTTCAGCATATTGAAAGACGGTCGGATCGCG (SEQ ID NO: 17) | BHQ-1 |

| Taqman Name | 5' Fluor | Sequence | 3' Quencher |
| --- | --- | --- | --- |
| DENV1 BHQ+ | FAM | CTCGCGCGTTTCAGCATAT (SEQ ID NO: 18) | BHQ-1+ |
| DENV2 BHQ+ | FAM | CTCTCGCGTTTCAGCATAT (SEQ ID NO: 19) | BHQ-1+ |

TABLE 2-continued

Probe sequences for the dengue multiplex rRT-PCR.

| DENV2 Alt BHQ+ | FAM | CTCTCACGTTTCAGCATATTG (SEQ ID NO: 20) | BHQ-1+ |
| DENV3 BHQ+ | FAM | CTCACGCGTTTCAGCATAT (SEQ ID NO: 21) | BHQ-1+ |

RT-PCR and Internal Control Assays

The dengue multiplex rRT-PCR was performed using the SuperScript III Platinum One-Step qRT-PCR (Invitrogen, Carlsbad, Calif.). Reaction mixtures were scaled from the manufacturer recommended volume of 50 μL to 25 μL per reaction. Each reaction contained 300 nM primers for DEN 1-3 and 450 nM primers for DEN 4. Each probe was added to 600 nM in the final PCR reaction. RT-PCR reactions were performed using the Rotor-Gene Q instrument (Qiagen, Valencia, Calif.). Cycling conditions were the following: 52° C. for 15 minutes (RT step); 94° C. for 2 minutes; 45 cycles of 94° C. for 15 seconds, 55° C. for 20 seconds, 60° C. for 20 seconds, and 68° C. for 20 seconds. Detection was performed in the green, yellow, orange, and red channels at 55° C.; the gain was set at 10 for green, yellow, and orange, and 5.33 for red. Four-step cycling was initially used to detect signal at different temperatures, but it was maintained as it showed improved sensitivity and curve generation compared to standard, three-step cycling (data not shown). During analysis, slope-correction was performed for each channel. Additionally, the first five cycles were cropped from the orange and red channel to improve baseline normalization. The threshold was set at 0.05 for green and yellow and 0.025 for orange and red. A positive result was considered any curve crossing this threshold prior to cycle 40. All results after cycle 40 were evaluated individually. The crossing threshold (Ct) value for each sample was recorded and the concentration of RNA calculated from a standard curve generated using quantified plasmid DNA (see below). Serotype was determined based on the pattern of signals obtained from the four dengue probes (Table 3).

TABLE 3

Probe signals for each dengue serotype.

| | | Channel | | | |
| --- | --- | --- | --- | --- | --- |
| | | Green | Yellow | Orange | Red |
| Serotype | Dengue 1 | +++ | − | − | ++ |
| | Dengue 2 | + | ++ | − | − |
| | Dengue 3 | + | − | ++ | − |
| | Dengue 4 | − | − | − | ++ |

Any positive signal above the threshold is shown (+).
Dengue 1 has the strongest and earliest signal in green of any serotype (+++).
Other positive signals are designated (++).

Reaction mixtures using TaqMan probes were identical to those for the dengue multiplex assay, except that the concentration of each probe in the reaction was 200 nM. Cycling conditions for this assay were the following: 52° C. for 15 minutes (RT step); 94° C. for 2 minutes; 45 cycles of 94° C. for 15 seconds, 55° C. for 20 seconds, and 68° C. for 20 seconds. Signal was acquired in the green channel. The gain was optimized before the first acquisition, and a crossing threshold of 0.025 was set.

For the reference assay, a modified hemi-nested RT-PCR assay was used (Chien et al. (2006) J. Clin. Microbiol. 44: 1295-1304). This assay was performed as previously described, except that reactions were scaled to 25 μL. All reactions were carried out in a DNA Engine Thermocycler (Bio-Rad, Hercules, Calif.). Briefly, One Step RT-PCR Kit (Qiagen, Valencia, Calif.) was used for the RT-PCR reactions. 12.5 pmoles of primers mD1 and D2 were added to the reaction, and 2.5 μL of RNA was added. RT-PCR conditions included the following: an initial hold at 50° C. for 30 minutes; one cycle at 95° C. for 15 minutes, 55° C. for 15 seconds, and 72° C. for 30 seconds; 34 cycles of 95° C. for 15 seconds, 55° C. for 15 seconds, and 72° C. for 30 seconds; and a final 72° C. extension for 10 minutes. For the nested PCR step, Hotstart Taq Kit (Qiagen, Valencia, Calif.) was used and again the reaction mix was proportionally adjusted for a 25 μL final reaction volume. 12.5 pmoles of primers mD1, rTS1, mTS2, TS3, and TS4 were used per reaction, and 2.5 μL of RT-PCR reaction product was added. Cycling conditions were the following: 95° C. for 15 minutes, then 25 cycles of 95° C. for 15 seconds, 55° C. for 15 seconds, and 72° C. for 30 seconds. Product was detected by 2.5% agarose gel electrophoresis, and serotypes were determined by product size (DEN 1, 208 bp; DEN 2, 119 bp; DEN 3, 288 bp; and DEN 4, 260 bp).

A separate, internal control reaction for the detection of RNAse P was performed on clinical samples. This assay has been previously described, though the protocol was modified for this study (WHO/CDC (2009) WHO/CDC protocol of realtime RTPCR for influenza A(H1N1)). RT-PCR was carried out with SuperScript III Platinum One-Step qRT-PCR (Invitrogen, Carlsbad, Calif.) and the same cycling conditions as the multiplex dengue rRT-PCR were used. The reaction volume was scaled to 25 μL, and the final reaction mixture contained 200 nM forward and reverse primers and 100 nM probe.

Reference Virus RNA

Genomic RNA extracted from control strains of the four dengue serotypes, DEN 1 Hawaii 1944, Den 2 New Guinea C strain, DEN 3 strain H87, and DEN 4 strain H241 were obtained from Vircell (Grenada, Spain). Extracted genomic RNA of three strains of West Nile Virus WNV (NY 1999; clinical isolate, previously reported as NAL strain (Rossini et al. (2011) Emerg. Infect. Dis. 17: 903-906); and B956), and a single strain each of Japanese Encephalitis Virus (JEV) and Tick-born Encephalitis Virus (TBEV) was obtained from the St. Orsola-Malphighi Hospital, Regional Reference Center for Microbiological Emergencies (Bologna, Italy).

Plasmid Generation, Quantitation, and Sequencing

Sequences for control strains of DEN 1-4 were amplified and cloned using the TOPO TA Cloning Kit with PCR 2.1 TOPO (Invitrogen, Carlsbad, Calif.). Amplicons were generated by RT-PCR as described above, except that reactions were carried out in a DNA Engine Thermocycler (Bio-Rad, Hercules, Calif.) without probe. Amplicons were detected on a 2% agarose gel, and 2 μL of each PCR reaction was used in the cloning reaction. Four clones for each serotype were generated, and the presence of the cloned insert was confirmed by PCR using the Fermentas 2×PCR Master Mix (Fermentas, Glen Burnie, Md.) and the same mix of dengue primers used in the rRT-PCR. 2 µL of culture broth were boiled and cooled, then included in PCR reactions otherwise performed according to the manufacturer's recommendations. Cycling conditions included an initial hold at 94° C. for 2 minutes, followed by 45 cycles of 94° C. for 15 seconds, 55° C. for 30 seconds, and 68° C. for 30 seconds. Amplicons were again detected on a 2% agarose gel. Plasmids from two clones of each serotype were then extracted using the GeneJET Plasmid Miniprep Kit (Fermentas, Glen Burnie, Md.). The concentration of plasmid DNA was quantified using the AccuBlue High Sensitivity dsDNA Quantitation Kit (Biotium Inc., Hayward, Calif.). 25, 50, and 100-fold dilutions were tested in triplicate. A standard curve was generated and the concentration of plasmid in the initial eluate calculated.

Multiplex rRT-PCR Validation

The validation was performed on the dengue multiplex rRT-PCR, consistent with previously published recommendations (Burd (2010) Clin. Microbiol. Rev. 23: 550-576). An identical validation process was performed for the assay utilizing TaqMan probes. For each serotype, linearity studies were performed on serial 10-fold dilutions of both quantified plasmid DNA and reference RNA. For the plasmid DNA, dilutions from 7.0 $\log_{10}$ copies/µL to 1 copy/µL were tested in triplicate on a single run. The concentrations of the reference RNA were originally quantified by the manufacturer in ng/µL of total RNA. 10-fold dilutions from 1 ng/µL to 0.01 µg/µL RNA were therefore tested in triplicate on a single run. Using the standard curve generated with dilutions of plasmid DNA, the concentration in dengue virus genome complimentary DNA (cDNA) equivalents/µL was calculated for the highest concentration of RNA (1 ng/µL) for each serotype. Dilutions were made on a single day for each serotype. The linear range was established by fitting a best-fit line to the data by regression analysis and included the range where the R2 value for this line was ≥0.99.

Following the establishment of the linear range, precision studies were performed using three dilutions of RNA controls (high positive, low positive, and limit of quantitation). These were performed as 5 replicates on 3 separate days. Fresh dilutions were made on the day of each run from aliquots of high concentration stocks (1 ng/µL, high positive). Intra- and inter-run variability was calculated from the log-concentration of the samples. To establish the lower limit of 95% detection (95% LLOD), the lowest concentrations of RNA at which all five replicates were detectable during the linear range study were used as the starting point. 10 replicates each of four, two-fold dilutions were tested on a single run. The 95% LLOD was then calculated using probit analysis.

Analytical sensitivity for the multiplex assay was compared to the reference assay. The dilutions made for the test of linearity using RNA was first added to the RT-PCR step of the hemi-nested PCR. Each 10-fold dilution was run in duplicate in the reference assay. Clinical sensitivity was evaluated by comparing the results of the dengue multiplex rRT-PCR with the reference standard using clinical samples described below. Agreement between the two assays was determined both for detection of dengue and serotype specificity.

Specificity was further evaluated by testing samples positive for West Nile virus (WNV), Japanese encephalitis virus (JEV), tick-borne encephalitis virus (TBEV), yellow fever 17D (YF-17D), and hepatitis C virus (HCV) as well as negative patient samples initially sent to the Stanford Clinical Virology Laboratory for HCV viral load testing. The control strains of JEV, TBEV, and WNV are described above. For YF-17D, extracted, control genomic RNA was obtained (Vircell, Grenada, Spain) and tested at concentrations of at least 12,500 copies/µL and 250 copies/µL. Twenty, de-identified plasma samples from patients with HCV and twenty samples from patients negative for HCV were extracted and tested by the multiplex rRT-PCR assay.

The test characteristics of the TaqMan assay are similar to those documented for the dengue multiplex assay (data not shown). Assay performance using the alternate DEN 1 probe appeared to be identical to that using the original DEN 1 probe based on side-by-side comparisons, though a complete validation is pending.

Participants 40 de-identified plasma samples from children presenting to the Lady Ridgeway Hospital (Colombo, Sri Lanka) with an acute febrile illness were tested. These samples were collected prospectively from Mar. 18 to May 28, 2012. These patients were clinically diagnosed with dengue fever, dengue hemorrhagic fever or dengue shock syndrome according to the WHO 1997 recommendations (World Health Organization. (1997) Dengue haemorrhagic fever: diagnosis, treatment, prevention, and control. Geneva: World Health Organization, viii). Patients were tested with the Hexagon GmbH Dengue assay (HUMAN Diagnostics, Wiesbaden, Germany), which is a rapid assay detecting IgM and IgG antibodies. Patients were diagnosed with primary dengue if they were IgM positive and IgG negative. Patients with detectable IgG were judged to have secondary dengue infection. Patient data included patient age, clinical diagnosis (DF, DHF, or DSS), and whether the patient died as a result of this infection.

15 de-identified, archived plasma samples from the St. Orsola-Malphighi Hospital, Regional Reference Center for Microbiological Emergencies (Bologna, Italy) were also received for testing. These samples were compromised during shipping, but were still tested by both the multiplex dengue rRT-PCR and reference assays.

Nucleic Acid Extraction

Nucleic acid extraction was performed using the QIAamp Viral RNA Mini Kit (Qiagen, Valencia, Calif.). All extractions were performed according to the manufacturer's recommendations. Extractions were performed using 140 µL of patient plasma, eluted into 60 µL of buffer AVE.

The quantitation of clinical specimens in cDNA equivalents/mL serum or plasma took into account these extraction and elution volumes and was calculated using the following formula: (cDNA equivalents/µL*60 µL)/(0.14 mL).

Ethics

The Institutional Review Board at Stanford University waived review of this study as no protected health information was obtained for patient samples.

Statistics

Basic statistical analysis was performed using Excel software (Microsoft, Bellevue, Wash.) and GraphPad software (GraphPad, La Jolla, Calif.). Probit analysis was performed using SPSS (IBM, Armonk, N.Y.).

Results

Linearity and Lower Limit of Detection

Figure 1B:
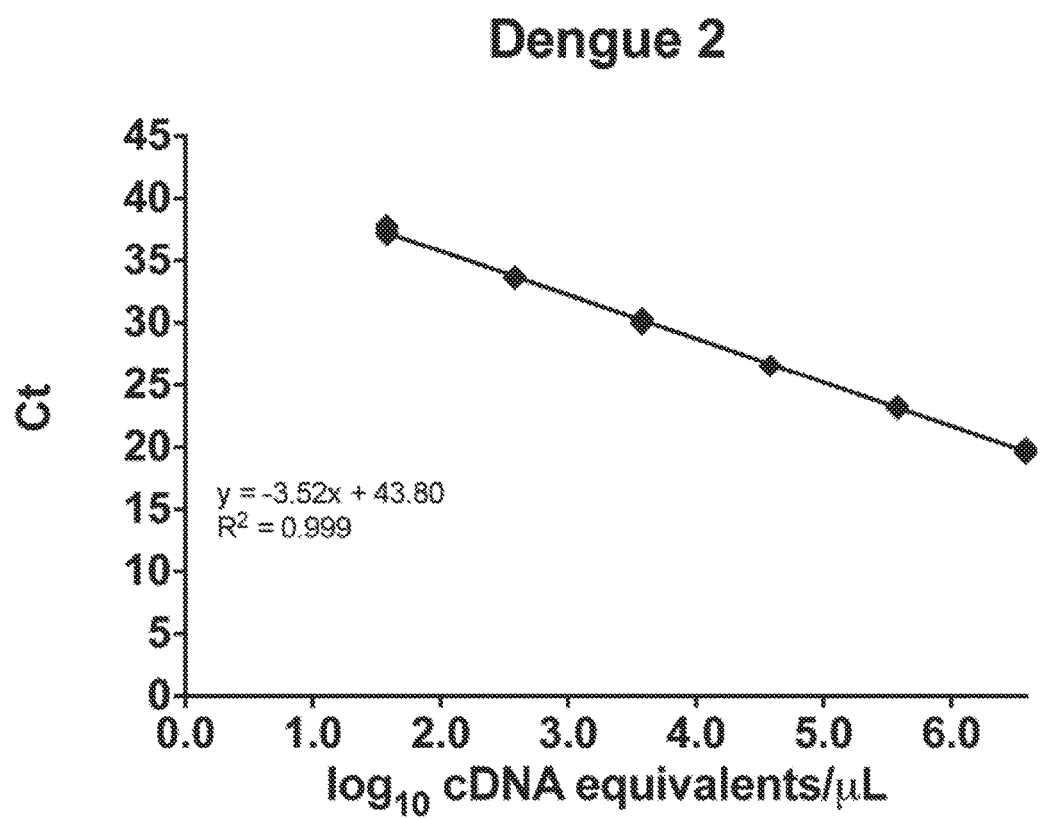
Figure 1C:
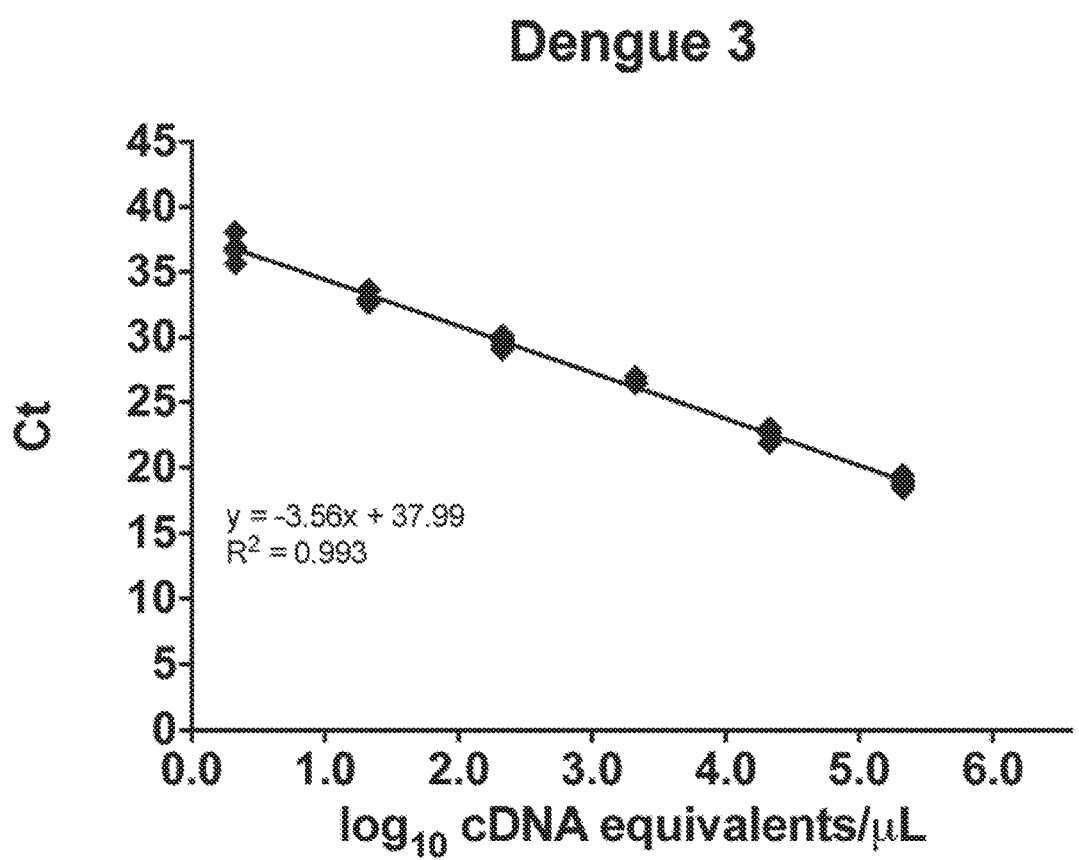
Figure 1D:
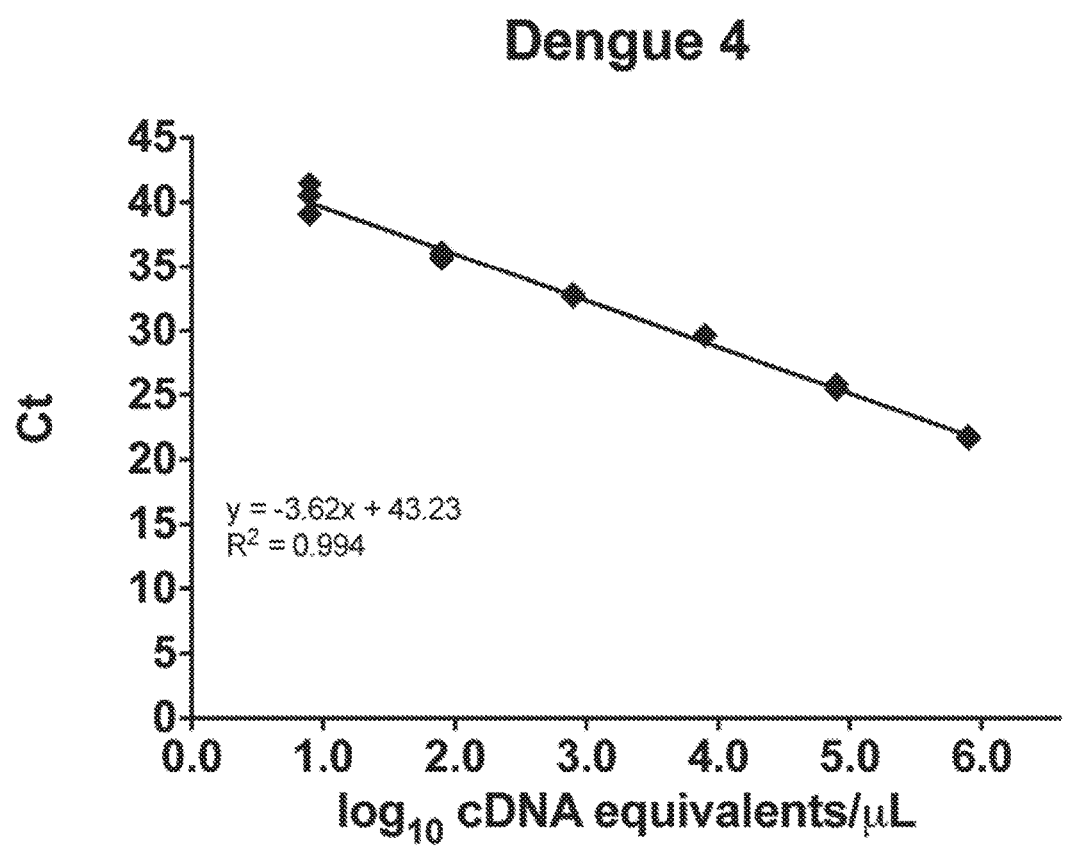

The primers and probe sets used in the multiplex assay are shown in Tables 1 and 2. The probes differ by one to four bases between the different serotypes and are listed by the channel in which they are detected. The pattern of signal obtained from the different probes for each serotype is displayed in Table 3. Using dengue reference RNA dilutions, the linear range for each serotype extended from 1.0 ng RNA/µL to 0.01 pg RNA/µL. Based on standard curves generated with dilutions of plasmid DNA, the concentration in dengue virus cDNA equivalents/µL for the highest concentration of RNA was determined for each serotype. The linear range of the multiplex assay therefore corresponds to the following cDNA equivalents/µL: DEN 1, 5.8 to 0.8 $\log_{10}$; DEN 2, 6.6 to 1.6 $\log_{10}$; DEN 3, 5.3 to 0.3 $\log_{10}$; DEN 4, 5.9 to 0.9 $\log_{10}$ (FIG. 1). Using plasmid DNA, the linear range for each serotype extended from 7.0 to 1.0 $\log_{10}$ copies/µL for DEN 1-3 and from 7.0 to 2.0 $\log_{10}$ copies/µL for DEN 4 (data not shown).

The lower limit of 95% detection (LLOD) was determined for each serotype in the multiplex assay by probit analysis using reference RNA dilutions. The LLOD was calculated to be 0.3 cDNA equivalents/µL for DEN 1, 13.8 for DEN 2, 0.8 for DEN 3, and 12.4 for DEN 4. For comparison, duplicates of the same RNA dilutions were run, on the same day, using the reference assay. The lowest concentrations detected by the reference assay were 6 cDNA equivalents/µL (2 of 2 replicates) for DEN 1, 3800 (2 of 2 replicates) for DEN 2, 21 (1 of 2 replicates) for DEN 3, and 79 (1 of 2 replicates) for DEN 4. The multiplex assay, therefore, was more analytically sensitive for each serotype than the reference assay.

Precision

Both intra- and inter-run precision were calculated for each serotype at three concentrations (high-positive, low-positive, and limit-of-quantitation) using reference RNA. These calculations were performed using the $\log_{10}$ cDNA equivalents/µL for each sample, except for DEN 3 at the limit of quantitation where the mean concentration and precision calculations were expressed on the linear scale. Each mean concentration as well as intra- and inter-run precision are shown in Table 4.

Specificity

Extracted, genomic RNA from one strain each of JEV and TBEV, three strains of WNV, and high and low concentrations of the 17D strain of YF showed no detectable signal in the multiplex rRT-PCR. 40 archived patient samples that had previously been sent for HCV testing (20 positive samples and 20 negative samples) were also tested. The positive samples had a median HCV viral load of 6.52 log 10 copies/mL (range 1.63-7.66 log 10 copies/mL). These samples showed no detectable signal in the multiplex rRT-PCR assay.

Clinical Samples 40 plasma samples were obtained from children in Sri Lanka, collected prospectively during a single dengue season; 36 patients had detectable IgM at diagnosis (90%). These samples were tested using both the multiplex rRT-PCR and reference assays. The multiplex assay was positive in 38 patients (95%, 37 DEN 1 and 1 DEN 3), whereas the reference assay was only positive in 16 (40%, 16 DEN 1). All samples detected by the reference assay were also detected by the multiplex assay. In the 36 patients with detectable IgM, the multiplex rRT-PCR was positive in 35 (97.2%). The samples contained similar levels of RNAse P RNA confirming adequate extraction and the absence of RT-PCR inhibitors (data not shown).

The composition of the group positive by the dengue multiplex rRT-PCR alone and the group positive by both assays are shown in Table 5. These two groups were generally similar. However, patients that tested positive only by the multiplex rRT-PCR were more likely to have secondary dengue (p=0.047), and they had a lower average viral load (p=0.0002). Two of the forty patients tested negative by both assays. One patient was clinically diagnosed with DF and had a positive IgM on day-of-illness five. The second patient was diagnosed with an undifferentiated febrile illness and tested IgM negative on day-of-illness seven. A single patient died; their viral load was 3.2 $\log_{10}$ cDNA equivalents/mL on day of illness seven.

TABLE 4

Precision analysis of the multiplex rRT-PCR.

| | | Inter-Run Variability | | | Intra-Run Variability | | |
|---|---|---|---|---|---|---|---|
| | | Mean $\log_{10}$copies/µL | SD | % CoV | Mean Range · $\log_{10}$ copies/µL | SD Range | % CoV Range |
| Dengue 1 | High-positive | 5.77 | 0.03 | 0.6 | 5.75-5.79 | 0.01-0.04 | 0.3-0.7 |
| | Low-positive | 2.67 | 0.03 | 1.3 | 2.65-2.69 | 0.02-0.04 | 0.7-1.7 |
| | Limit of quantitation | 0.49 | 0.12 | 23.7 | 0.4-0.54 | 0.07-0.12 | 17.6-22.0 |
| Dengue 2 | High-positive | 6.60 | 0.06 | 0.9 | 6.57-6.67 | 0.02-0.05 | 0.3-0.8 |
| | Low-positive | 3.57 | 0.06 | 1.7 | 3.51-3.60 | 0.03-0.07 | 0.7-1.8 |
| | Limit of quantitation | 1.47 | 0.11 | 7.8 | 1.41-1.59 | 0.04-0.09 | 3.0-6.5 |
| Dengue 3 | High-positive | 5.18 | 0.18 | 3.4 | 5.05-5.33 | 0.11-0.18 | 2.1-3.5 |
| | Low-positive | 1.99 | 0.14 | 7.1 | 1.85-2.10 | 0.09-0.12 | 4.3-5.7 |
| | Limit of quantitation* | 0.73 | 0.45 | 61.8 | 0.56-0.99 | 0.35-0.56 | 56.9-61.3 |
| Dengue 4 | High-positive | 5.85 | 0.06 | 1.0 | 5.78-5.90 | 0.03-0.05 | 0.5-0.8 |
| | Low-positive | 2.88 | 0.06 | 2.0 | 2.85-2.93 | 0.02-0.07 | 0.7-2.4 |
| | Limit of quantitation | 1.99 | 0.10 | 5.2 | 1.94-2.04 | 0.06-0.15 | 3.1-7.5 |

*Expressed as copies/µL

SD, standard deviation;

% CoV, percent coefficient of variation

TABLE 5

Comparison of patients from Sri Lanka that tested positive only by the multiplex rRT-PCR and those that tested positive by both the multiplex rRT-PCR and reference assays.

|  | Multiplex rRT-PCR Positive Reference Method Negative | Multiplex rRT-PCR Positive Reference Method Positive | p-value |
|---|---|---|---|
| Patients, n (%) | 22 (55) | 16 (40) | ND |
| Age, mean (SD) | 7.1 (3.6) | 6.1 (4.0) | 0.43 |
| Day of Illness, mean (SD) | 5.8 (1.6) | 6.1 (1.2) | 0.53 |
| IgM Positive, n (%) | 19 (86) | 16 (100) | 0.25 |
| Primary Dengue, n (%) | 7 (32) | 11 (69) | 0.047 |
| Illness Severity, n (%) |  |  |  |
| DF | 15 (68) | 6 (38) | 0.10 |
| DHF/DSS | 7 (32) | 10 (62) |  |
| Any ICU Care, n (%) | 4 (18) | 7 (44) | 0.15 |
| Viral Load, mean (SD) ($Log_{10}$ copies/mL) | 2.98 (0.61) | 4.4 (1.41) | 0.0002 |

ND, not determined;
SD, standard deviation

Fifteen archived patient samples that had been collected in Italy were also tested. Of these, four samples were detectable by both the multiplex rRT-PCR and reference assays (one sample of each serotype), and six more samples were detectable by only the multiplex rRT-PCR (4 DEN 1 and one each of DEN 2 and DEN 3). Five samples were negative by both assays. The Italy samples contained similar levels of RNAse P RNA, though the levels were, on average, about 10-fold lower than those found in the Sri Lanka samples (data not shown).

Overall, the multiplex rRT-PCR detected 100% (20/20) of the samples detected by the reference assay, with perfect serotype agreement. Furthermore, the multiplex rRT-PCR identified dengue RNA in 28 additional clinical specimens from patients with known recent dengue infection.

Discussion

This study describes a new, multiplex rRT-PCR for the detection, quantitation, and serotyping of dengue virus from patient samples. A laboratory validation of the assay was performed using reference RNA of the four dengue serotypes and clinical specimens from Sri Lanka and Italy.

The dengue multiplex rRT-PCR was compared to a modified version of a hemi-nested RT-PCR that has been in use for at least two decades (Lanciotti et al. (1992) J. Clin. Microbiol. 30: 545-551). The modifications were made previously to improve the sensitivity of the reference assay (Chien et al. (2006) J. Clin. Microbiol. 44: 1295-1304). Using serial dilutions of DEN 1-4 reference RNA, the dengue multiplex rRT-PCR was shown to be more analytically sensitive than the reference assay. Consistent with this finding, dengue virus RNA was detectable in more patient specimens using the multiplex rRT-PCR than the reference assay. The majority of patients included in this study were diagnosed with dengue by IgM detection, which does not reliably appear until day-of-illness five, when viremia has often decreased below the level of detection for the reference assay (Blacksell et al. (2006) Clin. Infect. Dis. 42: 1127-1134; Blacksell et al. (2011) Clin. Vaccine. Immunol. 18: 2095-2101). In previous studies, these samples are often not evaluated, given low rates of RT-PCR positivity (Johnson et al. (2005) J. Clin. Microbiol. 43: 4977-4983). In contrast, the dengue multiplex rRT-PCR remains sensitive for the diagnosis of dengue fever even after the development of IgM antibodies, which should lengthen the period of time during which a patient can receive a virologically confirmed, serotype-specific diagnosis of dengue. Despite this sensitivity, the dengue multiplex rRT-PCR was shown to be specific for dengue viruses and did not amplify related flaviviruses, even at very high viral loads.

Further benefits of the dengue multiplex rRT-PCR include its single-reaction set-up and a reaction set-up to result time that is much shorter than the hemi-nested PCR (3 hours versus 10 hours). A number of multiplex assays have previously been described in the literature, but these often require multiple steps or separate reactions for serotyping (Hue et al. (2011) J. Virol. Methods 177: 168-173; Das et al. (2008) J. Clin. Microbiol. 46: 3276-3284; Shu et al. (2003) J. Clin. Microbiol. 41: 2408-2416). Single-reaction assays, when compared directly to the reference assay used here, have been less analytically sensitive (Johnson et al. (2005) J. Clin. Microbiol. 43: 4977-4983). The real-time design of this assay allows for faster results than the reference assay, though currently it does not provide a result as rapidly as point-of-care diagnostics such as NS1 and IgM lateral flow detection kits. These rapid antigen and antibody assays, however, have significant limitations and do not provide the amount of information available from a serotype-specific multiplex rRT-PCR (Blacksell et al. (2008) Diagn. Microbiol. Infect. Dis. 60: 43-49; Guzman et al. (2010) PLoS Negl. Trop. Dis. 4; Tricou et al. (2010) BMC Infect Dis 10: 142).

The assay described herein was designed and validated as a quantitative test for dengue virus. Though the clinical utility of viral load testing in the management of patients with dengue fever remains unclear, previous studies have shown that patients with higher viral loads are at an increased risk for severe disease. Vaughn, et al. showed that peak viremia, when identified, correlated with severe disease in children infected with DEN 1 and DEN 2 (Vaughn et al. (2000) J. Infect. Dis. 181: 2-9). It has also been shown that detectable viremia on the day of defervescence identifies patients at an increased risk for DHF (Wang et al. (2006) Clin. Infect. Dis. 43: 1023-1030). In addition, studies have shown higher levels of peak viremia in secondary infection but also suggest that there may be differences based on the serotype of the causative dengue strain (Duyen et al. (2011) J. Infect. Dis. 203: 1292-1300; Tricou et al. (2011) PLoS Negl Trop Dis 5: e1309). Identifying clinically meaningful thresholds by quantitative rRT-PCR, may, then, be serotype-specific.

This study involved a rigorous laboratory validation of the dengue multiplex rRT-PCR, which was designed by using sequences from varied locations over the past twenty years. While this design strategy should improve the generalizability of these results, the study is limited by the relatively small sample size included in the clinical evaluation and the predominant representation of DEN 1 in these samples. While the dengue multiplex rRT-PCR compared favorably to the reference molecular assay, particularly in samples expected to have low viral loads, it will need to be tested using a larger number of clinical specimens from patients infected with all four dengue serotypes. Furthermore, the assay was validated as a quantitative test, but further studies using serial samples collected over the course of a patient's illness will need to be performed in order to show that this assay can be used for the monitoring of dengue viral loads.

In summary, this study describes a single-reaction, multiplex rRT-PCR for the detection, quantitation, and serotyping of dengue viruses from patient serum or plasma. This assay is more analytically sensitive than the reference molecular assay, and clinically, was able to detect and serotype virus late in the clinical course of patients with detectable dengue IgM. This assay makes an important contribution to available dengue diagnostics and warrants further study in larger cohorts of dengue patients.

Thus, oligonucleotide reagents, including primers and probes, as well as methods of using the reagents for detection, quantitation, and serotyping dengue virus are described. Although preferred embodiments of the subject invention have been described in some detail, it is understood that obvious variations can be made without departing from the spirit and the scope of the invention as defined herein.

What is claimed is:

1. A composition for detecting dengue virus in a biological sample using a nucleic acid amplification assay, the composition comprising at least one set of oligonucleotide primers comprising a forward primer and a reverse primer capable of amplifying at least a portion of a dengue virus genome, said portion comprising a 5' UTR sequence or a dengue virus capsid coding sequence, wherein said primers are not more than 40 nucleotides in length, wherein said set of primers is selected from the group consisting essentially of:
   (a) a forward primer comprising the sequence of SEQ ID NO:5 and a reverse primer comprising the sequence of SEQ ID NO:9;
   (b) a forward primer comprising the sequence of SEQ ID NO:5 and a reverse primer comprising the sequence of SEQ ID NO:10;
   (c) a forward primer comprising the sequence of SEQ ID NO:5 and a reverse primer comprising the sequence of SEQ ID NO:11;
   (d) a forward primer comprising the sequence of SEQ ID NO:6 and a reverse primer comprising the sequence of SEQ ID NO:10;
   (e) a forward primer comprising the sequence of SEQ ID NO:6 and a reverse primer comprising the sequence of SEQ ID NO:11;
   (f) a forward primer comprising the sequence of SEQ ID NO:7 and a reverse primer comprising the sequence of SEQ ID NO:9;
   (g) a forward primer comprising the sequence of SEQ ID NO:8 and a reverse primer comprising the sequence of SEQ ID NO:12;
   (h) a forward primer and a reverse primer each comprising at least 10 contiguous nucleotides from the corresponding nucleotide sequences of the forward primer and reverse primer of a primer set selected from the group consisting essentially of (a)-(g);
   (i) a forward primer and a reverse primer comprising at least one nucleotide sequence that differs from the corresponding nucleotide sequence of the forward primer or reverse primer of a primer set selected from the group consisting essentially of (a)-(g) in that the primer has up to three nucleotide changes compared to the corresponding sequence, wherein the primer is capable of hybridizing to and amplifying dengue virus nucleic acids in the nucleic acid amplification assay;
   (j) a forward primer and a reverse primer comprising nucleotide sequences that are complements of the corresponding nucleotide sequences of the forward primer and reverse primer of a primer set selected from the group consisting essentially of (a)-(i); and
   (k) a combination of a primer set selected from the group comprising (a)-(j).

2. The composition of claim 1, further comprising at least one detectably labeled oligonucleotide probe sufficiently complementary to and capable of hybridizing with dengue virus RNA or an amplicon thereof.

3. The composition of claim 2, wherein the probe is selected from the group consisting essentially of:
   (a) a probe comprising the sequence of SEQ ID NO: 13,
   (b) a probe comprising the sequence of SEQ ID NO: 14,
   (c) a probe comprising the sequence of SEQ ID NO: 15,
   (d) a probe comprising the sequence of SEQ ID NO: 16,
   (e) a probe comprising the sequence of SEQ ID NO: 17,
   (f) a probe comprising the sequence of SEQ ID NO: 18,
   (g) a probe comprising the sequence of SEQ ID NO: 19,
   (h) a probe comprising the sequence of SEQ ID NO: 20,
   (i) a probe comprising the sequence of SEQ ID NO: 21,
   (j) a probe that differs from the corresponding nucleotide sequence of a probe selected from the group consisting essentially of (a)-(i) in that the probe has up to three nucleotide changes compared to the corresponding sequence, wherein the probe is capable of hybridizing to and detecting the dengue virus RNA or an amplicon thereof, and (k) a combination of probes selected from the group comprising (a)-(j).

4. The composition of claim 3, comprising a set of probes, wherein the set of probes comprises a probe comprising the sequence of SEQ ID NO:13, a probe comprising the sequence of SEQ ID NO:14, a probe comprising the sequence of SEQ ID NO:15, and a probe comprising the sequence of SEQ ID NO:16.

5. The composition of claim 4, wherein the set of primers comprises a primer comprising the sequence of SEQ ID NO:5, a primer comprising the sequence of SEQ ID NO:6, a primer comprising the sequence of SEQ ID NO:7, a primer comprising the sequence of SEQ ID NO:8, a primer comprising the sequence of SEQ ID NO:9, a primer comprising the sequence of SEQ ID NO:10, a primer comprising the sequence of SEQ ID NO:11, and a primer comprising the sequence of SEQ ID NO:12.

6. An isolated oligonucleotide not more than 40 nucleotides in length comprising:
  (a) a nucleotide sequence comprising at least 10 contiguous nucleotides from a nucleotide sequence selected from the group consisting essentially of SEQ ID NOS: 5-21;
  (b) a nucleotide sequence that differs from a nucleotide sequence selected from the group consisting essentially of SEQ ID NOS:5-21 by up to three nucleotide changes, wherein the oligonucleotide is capable of hybridizing to and amplifying dengue virus nucleic acids; or
  (c) complements of (a) and (b).

7. An isolated oligonucleotide selected from the group consisting essentially of:
  (d) an oligonucleotide consisting essentially of a nucleotide sequence selected from the group consisting essentially of SEQ ID NOS:5-21;
  (e) an oligonucleotide complementary to an oligonucleotide of (a); and
  (f) a combination of an oligonucleotide selected from (a) and (b).

8. A kit for detecting dengue virus in a biological sample, the kit comprising:
  written instructions for identifying the presence of dengue virus; and
  at least one set of primers comprising a forward primer and a reverse primer capable of amplifying at least a portion of a dengue virus genome, said portion comprising a 5' UTR sequence or a dengue capsid coding sequence, wherein said primers are not more than about 40 nucleotides in length, wherein said set of primers is selected from the group consisting essentially of:
  (g) a forward primer comprising the sequence of SEQ ID NO:5 and a reverse primer comprising the sequence of SEQ ID NO:9;
  (h) a forward primer comprising the sequence of SEQ ID NO:5 and a reverse primer comprising the sequence of SEQ ID NO:10;
  (i) a forward primer comprising the sequence of SEQ ID NO:5 and a reverse primer comprising the sequence of SEQ ID NO:11;
  (j) a forward primer comprising the sequence of SEQ ID NO:6 and a reverse primer comprising the sequence of SEQ ID NO:10;
  (k) a forward primer comprising the sequence of SEQ ID NO:6 and a reverse primer comprising the sequence of SEQ ID NO:11;
  (l) a forward primer comprising the sequence of SEQ ID NO:7 and a reverse primer comprising the sequence of SEQ ID NO:9;
  (m) a forward primer comprising the sequence of SEQ ID NO:8 and a reverse primer comprising the sequence of SEQ ID NO:12;
  (n) a forward primer and a reverse primer each comprising at least 10 contiguous nucleotides from the corresponding nucleotide sequences of the forward primer and reverse primer of a primer set selected from the group consisting essentially of (a)-(g);
  (o) a forward primer and a reverse primer comprising at least one nucleotide sequence that differs from the corresponding nucleotide sequence of the forward primer or reverse primer of a primer set selected from the group consisting essentially of (a)-(g) in that the primer has up to three nucleotide changes compared to the corresponding sequence, wherein the primer is capable of hybridizing to and amplifying dengue virus nucleic acids in the nucleic acid amplification assay;
  (p) a forward primer and a reverse primer comprising nucleotide sequences that are complements of the corresponding nucleotide sequences of the forward primer and reverse primer of a primer set selected from the group consisting essentially of (a)-(i); and
  (q) a combination of primers selected from the group comprising (a)-(j).

9. The kit of claim 8, further comprising at least one probe for detecting dengue virus in a biological sample, wherein the at least one probe is selected from the group consisting essentially of a probe comprising the sequence of SEQ ID NO:13, a probe comprising the sequence of SEQ ID NO:14, a probe comprising the sequence of SEQ ID NO:15, a probe comprising the sequence of SEQ ID NO:16, a probe comprising the sequence of SEQ ID NO:17, a probe comprising the sequence of SEQ ID NO:18, a probe comprising the sequence of SEQ ID NO:19, a probe comprising the sequence of SEQ ID NO:20, and a probe comprising the sequence of SEQ ID NO:21.

10. The kit of claim 9, comprising a set of probes for detecting dengue virus in a biological sample, wherein the set of probes comprises a probe comprising the sequence of SEQ ID NO:13, a probe comprising the sequence of SEQ ID NO:14, a probe comprising the sequence of SEQ ID NO:15, and a probe comprising the sequence of SEQ ID NO:16.

11. The kit of claim 8, comprising a primer comprising the sequence of SEQ ID NO:5, a primer comprising the sequence of SEQ ID NO:6, a primer comprising the sequence of SEQ ID NO:7, a primer comprising the sequence of SEQ ID NO:8, a primer comprising the sequence of SEQ ID NO:9, a primer comprising the sequence of SEQ ID NO:10, a primer comprising the sequence of SEQ ID NO:11, and a primer comprising the sequence of SEQ ID NO:12.

* * * * *

UNITED STATES PATENT AND TRADEMARK OFFICE
CERTIFICATE OF CORRECTION

| | |
|---|---|
| PATENT NO. | : 10,093,994 B2 |
| APPLICATION NO. | : 15/639930 |
| DATED | : October 9, 2018 |
| INVENTOR(S) | : Benjamin Pinsky et al. |

Page 1 of 1

It is certified that error appears in the above-identified patent and that said Letters Patent is hereby corrected as shown below:

In the Specification

In Column 1, after Line 13: Please insert the following header and paragraph:
--STATEMENT REGARDING FEDERALLY SPONSORED RESEARCH
This invention was made with Government support under contract TW008781 awarded by the National Institutes of Health. The Government has certain rights in the invention.--

Signed and Sealed this
Seventh Day of October, 2025

John A. Squires
*Director of the United States Patent and Trademark Office*